United States Patent
Honda et al.

(10) Patent No.: US 9,062,061 B2
(45) Date of Patent: Jun. 23, 2015

(54) COMPOUND HAVING PARP INHIBITORY ACTIVITY

(75) Inventors: Takahiro Honda, Ikoma (JP); Hiroshi Enomoto, Ikoma (JP); Kenji Kawashima, Ikoma (JP); Shinji Takaoka, Ikoma (JP); Yasutaka Fujioka, Ikoma (JP); Mamoru Matsuda, Ikoma (JP); Koji Ohashi, Ikoma (JP); Yukie Fujita, Ikoma (JP); Shin-ichiro Hirai, Ikoma (JP); Hiroaki Kurashima, Osaka (JP)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/232,160

(22) PCT Filed: Jul. 12, 2012

(86) PCT No.: PCT/JP2012/067775
§ 371 (c)(1),
(2), (4) Date: Apr. 7, 2014

(87) PCT Pub. No.: WO2013/008872
PCT Pub. Date: Jan. 17, 2013

(65) Prior Publication Data
US 2014/0243320 A1 Aug. 28, 2014

(30) Foreign Application Priority Data
Jul. 13, 2011 (JP) ................. 2011-154636

(51) Int. Cl.
*A61K 31/55* (2006.01)
*A61K 31/535* (2006.01)
*A61K 31/501* (2006.01)
*C07D 413/00* (2006.01)
*C07D 491/00* (2006.01)
*C07D 239/70* (2006.01)
*C07D 487/06* (2006.01)
*C07D 487/04* (2006.01)
*C07D 495/14* (2006.01)
*C07D 519/00* (2006.01)
*A61K 9/00* (2006.01)
*A61K 9/06* (2006.01)
*A61K 47/38* (2006.01)
*A61K 9/20* (2006.01)
*A61K 9/48* (2006.01)

(52) U.S. Cl.
CPC ............ *C07D 487/06* (2013.01); *C07D 487/04* (2013.01); *C07D 495/14* (2013.01); *C07D 519/00* (2013.01); *A61K 9/0048* (2013.01); *A61K 9/0095* (2013.01); *A61K 9/06* (2013.01); *A61K 47/38* (2013.01); *A61K 9/2018* (2013.01); *A61K 9/2054* (2013.01); *A61K 9/2059* (2013.01); *A61K 9/4858* (2013.01); *A61K 9/4866* (2013.01)

(58) Field of Classification Search
USPC ............... 544/115, 250, 252; 514/218, 233.2, 514/252.17
See application file for complete search history.

(56) References Cited

U.S. PATENT DOCUMENTS

| 4,105,766 A | 8/1978 | Alexander |
| 5,061,613 A | 10/1991 | Kaneko |

(Continued)

FOREIGN PATENT DOCUMENTS

| CN | 1441803 A | 9/2003 |
| CN | 101506214 A | 8/2009 |

(Continued)

OTHER PUBLICATIONS

Edited by C. G. Wermuth, translated under the supervision of Hiroshi Nagase, Saishin Soyaku Kagaku first volume, issued by Technomics, Inc., 1998 Nen, 1st edition, pp. 243-248.
Miki, K. et al., "Poly (ADP-ribose) Polymerase Inhibitor 3-Aminobenzamide Rescues N-Methyl-N-Nitrosourea-Induced Photoreceptor Cell Apoptosis in Sprague-Dawley Rats Through Preservation of Nuclear Factor-κb Activity", Experimental Eye Research, 84, pp. 285-292 (2007).
Office Action issued in corresponding Chinese Patent Application No. 201280034304.9 on Nov. 3, 2014 (11 pages).
YOU: "Pharmaceutical Chemistry", Chemical Industry Press, Jan. 31, 2004 (5 pages).

(Continued)

*Primary Examiner* — James O Wilson
*Assistant Examiner* — Oluwafemi Masha
(74) *Attorney, Agent, or Firm* — Buchanan, Ingersoll & Rooney PC

(57) ABSTRACT

A compound represented by the following general formula (1) or a salt thereof. $R^1$ represents a halogen atom and so on; $R^2$ and $R^3$ each represent a hydrogen atom and so on; $R^4$ and $R^5$ each represent a hydrogen atom and so on, or $R^4$ and $R^5$ may form an oxo group; $R^a$ and $R^b$ each represent a lower alkyl group optionally having a substituent and so on, or they may bind to each other to form a nitrogen-containing heterocyclic ring which may be substituted by one or plural $R^c$; $R^c$ represents an aryl group optionally having a substituent and so on; ring A represents a benzene ring and so on; and m represents 0, 1 or 2.

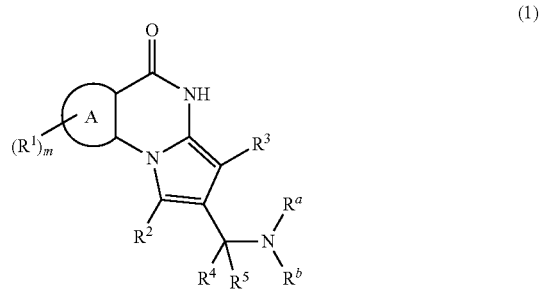

(1)

18 Claims, No Drawings

(56) References Cited

U.S. PATENT DOCUMENTS

| | | |
|---|---|---|
| 2003/0199502 A1 | 10/2003 | Zimmermann et al. |
| 2004/0077667 A1 | 4/2004 | Matsuoka et al. |
| 2005/0043333 A1 | 2/2005 | Ishida et al. |
| 2005/0080096 A1 | 4/2005 | Ishida et al. |
| 2008/0015182 A1 | 1/2008 | Penning et al. |

FOREIGN PATENT DOCUMENTS

| | | |
|---|---|---|
| WO | WO 02/06284 A1 | 1/2002 |
| WO | WO 02/48117 A1 | 6/2002 |
| WO | WO 03/055865 A1 | 7/2003 |
| WO | WO 03/063874 A1 | 8/2003 |
| WO | WO 2007/149907 A2 | 12/2007 |
| WO | WO 2009/041565 A1 | 4/2009 |
| WO | WO 2009/041566 A1 | 4/2009 |

OTHER PUBLICATIONS

International Search Report (PCT/ISA/210) mailed on Sep. 11, 2012, by the Japanese Patent Office as the International Searching Authority for International Application No. PCT/JP2012/067775.

C. Underhill et al., "A Review of PARP inhibitors: from bench to bedside", Annals of Oncology, 2011, pp. 268-279, vol. 22.

COMPOUND HAVING PARP INHIBITORY ACTIVITY

TECHNICAL FIELD

The present invention relates to a novel compound having PARP inhibitory activity.

BACKGROUND ART

PARP (Poly ADP Ribose Polymerase) is an enzyme existing in nuclei of cells of various organs, and is believed to be involved in repair of DNA strand break. As a compound having PARP inhibitory activity (hereinafter, also referred to as "PARP inhibitor"), various compounds have been reported heretofore, and for example, in WO 02/48117 A (Patent Document 1), WO 03/055865 A (Patent Document 2), and WO 03/063874 A (Patent Document 3), plural compounds are disclosed, and these compounds are suggested to have the potential to become therapeutic agents for many diseases.

In recent years, PARP inhibitors attract attention as novel anticancer drugs, and Annals of Oncology, 22, 268-279 (2011) (Non-Patent Document 1) describes that plural PARP inhibitors are under development as anticancer drugs.

Further, WO 2009/041565 A (Patent Document 4) and WO 2009/041566 A (Patent Document 5) respectively describe prophylaxis or therapy of keratoconjunctive disorder and posterior ocular disease by a PARP inhibitor.

CITATION LIST

Patent Document

PTD 1: WO 02/48117 A
PTD 2: WO 03/055865 A
PTD 3: WO 03/063874 A
PTD 4: WO 2009/041565 A
PTD 5: WO 2009/041566 A

Non Patent Document

NPD 1: Annals of Oncology, 22, 268-279 (2011)

SUMMARY OF INVENTION

Technical Problem

As described above, since PARP inhibitors are expected to have the potential to become therapeutic agents for various diseases, discovery of a novel compound having PARP inhibitory activity is an interesting issue.

Solution to Problem

In light of the above, the present inventors synthesized a variety of compounds for discovering a novel PARP inhibitor, and compared and examined their PARP inhibitory activities, to find that a compound represented by the following general formula (1) or a salt thereof has strong PARP inhibitory activity, and accomplished the present invention. Specifically, the present invention provides a compound represented by the following general formula (1) or a salt thereof (hereinafter, these are also collectively referred to as "present compound").

[Chemical Formula 1]

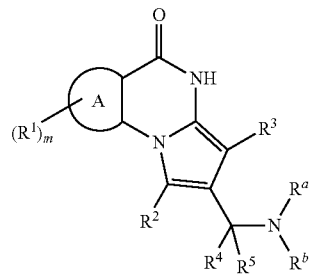

(1)

In the above general formula (1), $R^1$ represents a halogen atom, a lower alkyl group, a hydroxy group, a lower alkoxy group, an amino group, a nitro group or a cyano group; $R^2$ and $R^3$ may be the same or different and each represent a hydrogen atom, a halogen atom or a lower alkyl group; $R^4$ and $R^5$ may be the same or different and each represent a hydrogen atom, a deuterium atom or a lower alkyl group, or $R^4$ and $R^5$ may form an oxo group; $R^a$ and $R^b$ may be the same or different and each represent a hydrogen atom, a lower alkyl group optionally having a substituent or an aryl group optionally having a substituent; $R^a$ and $R^b$ may bind to each other to form a nitrogen-containing heterocyclic ring which may be substituted by one or plural $R^c$, $R^c$ represents a lower alkyl group optionally having a substituent, a lower cycloalkyl group optionally having a substituent, an aryl group optionally having a substituent, a heterocyclic group optionally having a substituent, a hydroxy group, a lower alkoxy group optionally having a substituent, a lower alkylcarbonyl group optionally having a substituent, a lower cycloalkylcarbonyl group optionally having a substituent, a lower alkylaminocarbonyl group optionally having a substituent, a lower cycloalkylaminocarbonyl group optionally having a substituent, a lower alkoxycarbonyl group optionally having a substituent, an amino group, a lower alkylamino group or a carboxyl group; ring A represents a benzene ring or an unsaturated heteromonocyclic ring; and m represents 0, 1 or 2.

Preferably, in the present compound, in the above general formula (1), $R^1$ represents a halogen atom or a lower alkyl group; $R^2$ and $R^3$ may be the same or different and each represent a hydrogen atom, a halogen atom or a lower alkyl group; $R^4$ and $R^5$ may be the same or different and each represent a hydrogen atom, a deuterium atom or a lower alkyl group, or $R^4$ and $R^5$ may form an oxo group; $R^a$ and $R^b$ may be the same or different and each represent a hydrogen atom, a lower alkyl group or an aryl group, and the lower alkyl group or the aryl group may be substituted by a deuterium atom, an aryl group, a heterocyclic group, an amino group or a lower alkylamino group; $R^a$ and $R^b$ may bind to each other to form a nitrogen-containing heterocyclic ring which may be substituted by one or plural $R^c$; $R^c$ represents a lower alkyl group, a lower cycloalkyl group, an aryl group, a heterocyclic group, a hydroxy group, a lower alkoxy group, a lower alkylcarbonyl group, a lower cycloalkylcarbonyl group, a lower alkylaminocarbonyl group, a lower cycloalkylaminocarbonyl group, a lower alkoxycarbonyl group, an amino group, a lower alkylamino group or a carboxyl group, and the lower alkyl group, the lower cycloalkyl group, the aryl group, the heterocyclic group, the lower alkoxy group, the lower alkylcarbonyl group, the lower cycloalkylcarbonyl group, the lower alkylaminocarbonyl group, the lower cycloalkylaminocarbonyl group, the lower alkoxycarbonyl group or the lower alkylamino group may be substituted by one or plural groups selected from the group consisting of a deuterium atom, a halogen atom, a lower alkyl group, a lower alkyl group substituted by a halogen atom, a lower cycloalkyl group, an aryl group, an aryl group substituted by a halogen atom, a heterocyclic group, a hydroxy group, a lower alkoxy group and a lower alkoxy group substituted by a lower alkylamino group; ring A represents a benzene ring or a 5-membered unsaturated heteromonocyclic ring; and m represents 0 or 1.

Preferably, in the present compound, in the above general formula (1), $R^1$ represents a halogen atom or a lower alkyl group; $R^2$ and $R^3$ each represent a hydrogen atom; $R^4$ and $R^5$ may be the same or different and each represent a hydrogen atom, a deuterium atom or a lower alkyl group, or $R^4$ and $R^5$ may form an oxo group; $R^a$ and $R^b$ may be the same or different and each represent a hydrogen atom, a lower alkyl group or an aryl group, and the lower alkyl group or the aryl group may be substituted by an aryl group, a heterocyclic group, an amino group or a lower alkylamino group; $R^a$ and $R^b$ may bind to each other to form a nitrogen-containing heteromonocyclic ring or a nitrogen-containing heterobicyclic ring which may be substituted by one or plural $R^c$; $R^c$ represents a lower alkyl group, a lower cycloalkyl group, an aryl group, a heterocyclic group, a hydroxy group, a lower alkoxy group, a lower alkylcarbonyl group, a lower cycloalkylcarbonyl group, a lower alkylaminocarbonyl group, a lower cycloalkylaminocarbonyl group, a lower alkoxycarbonyl group, an amino group, a lower alkylamino group or a carboxyl group, and the lower alkyl group, the lower cycloalkyl group, the aryl group, the heterocyclic group, the lower alkoxy group, the lower alkylcarbonyl group, the lower cycloalkylcarbonyl group, the lower alkylaminocarbonyl group, the lower cycloalkylaminocarbonyl group, the lower alkoxycarbonyl group or the lower alkylamino group may be substituted by one or plural groups selected from the group consisting of a halogen atom, a lower alkyl group, a lower alkyl group substituted by a halogen atom, a lower cycloalkyl group, an aryl group, an aryl group substituted by a halogen atom, a hydroxy group, a lower alkoxy group and a lower alkoxy group substituted by a lower alkylamino group, ring A represents a benzene ring or a 5-membered unsaturated heteromonocyclic ring; and m represents 0 or 1.

Preferably, in the present compound, in the above general formula (1), $R^a$ and $R^b$ may be the same or different and each represent a hydrogen atom, a lower alkyl group or a phenyl group, and the lower alkyl group may be substituted by a phenyl group, a pyridyl group, a morphonyl group, an amino group or a dimethylamino group.

Preferably, in the present compound, in the above general formula (1), $R^a$ and $R^b$ bind to each other to form a nitrogen-containing heterocyclic ring represented by the following formula (2a) or (3a);

[Chemical Formula 2]

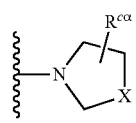

(2a)

[Chemical Formula 3]

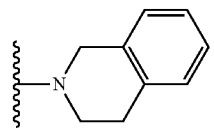

(3a)

in the above formula (2a), X represents $CH_2$, $CH_2CHR^{c\beta}$, $CH=CR^{c\beta}$, $CH_2NR^{c\beta}$ or $CH_2CH_2NR^{c\beta}$; $R^{c\alpha}$ represents a hydrogen atom, a halogen atom, a lower alkyl group or a phenyl group; $R^{c\beta}$ represents a hydrogen atom, a lower alkyl group, a lower cycloalkyl group, an aryl group, a heteromonocyclic group, a heterobicyclic group, a lower alkoxycarbonyl group, a lower cycloalkylcarbonyl group or a lower alkylamino group, the lower alkyl group, the lower cycloalkyl group, the aryl group, the heteromonocyclic group, the heterobicyclic group, the lower alkoxycarbonyl group or the lower cycloalkylcarbonyl group may be substituted by one or plural groups selected from the group consisting of a halogen atom, a lower alkyl group, a lower alkyl group substituted by a halogen atom, a lower cycloalkyl group, an aryl group, an aryl group substituted by a halogen atom, a hydroxy group, a lower alkoxy group and a lower alkoxy group substituted by a lower alkylamino group.

Preferably, in the present compound, in the above general formula (1), $R^a$ and $R^b$ bind to each other to form a nitrogen-containing heterocyclic ring represented by the following formula (2a);

[Chemical Formula 4]

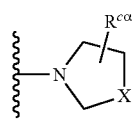

(2a)

in the above formula (2a), $R^{c\alpha}$ represents a hydrogen atom, a halogen atom, a lower alkyl group or a phenyl group; X represents $CH_2CHR^{c\beta}$, $CH=CR^{c\beta}$ or $CH_2NR^{c\beta}$; $R^{c\beta}$ represents a hydrogen atom, a lower alkyl group, a lower cycloalkyl group, an aryl group, a heteromonocyclic group, a heterobicyclic group, a lower alkoxycarbonyl group, a lower cycloalkylcarbonyl group or a lower alkylamino group, and the lower alkyl group, the lower cycloalkyl group, the aryl group, the heteromonocyclic group, the heterobicyclic group, the lower alkoxycarbonyl group or the lower cycloalkylcarbonyl group may be substituted by one or plural groups selected from the group consisting of a halogen atom, a lower alkyl group, a lower alkyl group substituted by a halogen atom, a lower cycloalkyl group, an aryl group, an aryl group substituted by a halogen atom, a hydroxy group, a lower alkoxy group and a lower alkoxy group substituted by a lower alkylamino group.

Preferably, in the present compound, in the above formula (2a), $R^{c\alpha}$ represents a hydrogen atom, a halogen atom, a methyl group or a phenyl group; $R^{c\beta}$ represents a hydrogen atom, a methyl group, a cyclohexyl group, a phenyl group, a pyridyl group, a piperidyl group, a thiazole group, a morphonyl group, an indolyl group, a furo[3,2-c]pyridin-4-yl group, a 1,3-benzodioxol-5-yl group, an ethoxycarbonyl group, a cyclopropylcarbonyl group or a dimethylamino group, and the methyl group, the cyclohexyl group, the phenyl group, the pyridyl group, the piperidyl group, the thiazole group, the morphonyl group, the indolyl group, the furo[3,2-c]pyridin- 4-yl group or the 1,3-benzodioxol-5-yl group may be substituted by one or plural groups selected from the group consisting of a halogen atom, a lower alkyl group, a lower alkyl group substituted by a halogen atom, a lower cycloalkyl group, a phenyl group, a phenyl group substituted by a halogen atom, a hydroxy group, a lower alkoxy group and a lower alkoxy group substituted by a dimethylamino group.

Preferably, in the present compound, in the above formula (2a), $R^{c\alpha}$ represents a hydrogen atom, X represents $CH_2NR^{c\beta}$, and $R^{c\beta}$ represents a phenyl group which may be substituted by one or plural groups selected from the group consisting of a halogen atom, a lower alkyl group, a hydroxy group and a lower alkoxy group.

Preferably, in the present compound, in the above general formula (1), $R^1$ represents a halogen atom.

Preferably, in the present compound, in the above general formula (1), $R^2$ and $R^3$ each represent a hydrogen atom.

Preferably, in the present compound, in the above general formula (1), $R^4$ and $R^5$ each represent a hydrogen atom.

Preferably, in the present compound, in the above general formula (1), ring A represents a benzene ring or an unsaturated heteromonocyclic ring represented by the following formula (4a).

[Chemical Formula 5]

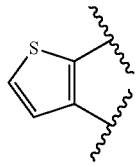

(4a)

The present invention also provides a compound selected from the following compounds or a salt thereof.

2-[4-(4-Fluorophenyl)piperazine-1-carbonyl]pyrrolo quinazolin-5(4H)-one,
2-[4-(4-Chlorobenzyl)piperazine-1-carbonyl]pyrrolo[1,2-a]quinazolin-5(4H)-one,
2-[4-(Thiazol-2-yl)piperazine-1-carbonyl]pyrrolo[1,2-a]quinazolin-5(4H)-one,
2-(4-Phenylpiperazine-1-carbonyl)pyrrolo quinazolin-5(4H)-one,
2-(4-Phenylpiperidine-1-carbonyl)pyrrolo[1,2-a]quinazolin-5(4H)-one,
2-(4-Phenyl-1,2,3,6-tetrahydropyridine-1-carbonyl)pyrrolo[1,2-a]quinazolin-5(4H)-one,
2-[4-(4-Chlorophenyl)-1,2,3,6-tetrahydropyridine-1-carbonyl]pyrrolo[1,2-a]quinazolin-5(4H)-one,
2-[4-(4-Fluorophenyl)-1,2,3,6-tetrahydropyridine-1-carbonyl]pyrrolo[1,2-a]quinazolin-5(4H)-one,
2-[4-(2-Fluorophenyl)piperazine-1-carbonyl]pyrrolo[1,2-a]quinazolin-5(4H)-one,
2-(4-Methylpiperazine-1-carbonyl)pyrrolo[1,2-a]quinazolin-5(4H)-one,
2-(4-Benzylpiperazine-1-carbonyl)pyrrolo[1,2-a]quinazolin-5(4H)-one,
2-[4-(4-Chlorophenyl)piperazine-1-carbonyl]pyrrolo[1,2-a]quinazolin-5(4H)-one,
2-[4-(4-Fluorobenzyl)piperazine-1-carbonyl]pyrrolo[1,2-a]quinazolin-5(4H)-one,
2-[4-(4-Fluorophenyl)piperidine-1-carbonyl]pyrrolo[1,2-a]quinazolin-5(4H)-one,
2-[4-(3-Fluorophenyl)piperazine-1-carbonyl]pyrrolo[1,2-a]quinazolin-5(4H)-one,
2-[4-(4-Methoxyphenyl)piperazine-1-carbonyl]pyrrolo[1,2-a]quinazolin-5(4H)-one,
2-[4-(Pyridin-2-yl)piperazine-1-carbonyl]pyrrolo[1,2-a]quinazolin-5(4H)-one,
2-[4-(Pyridin-3-yl)piperazine-1-carbonyl]pyrrolo[1,2-a]quinazolin-5(4H)-one,
2-[N-Methyl-N-(3-phenylpropyl)aminocarbonyl]pyrrolo[1,2-a]quinazolin-5(4H)-one,
2-[4-(4-Bromophenyl)piperazine-1-carbonyl]pyrrolo[1,2-a]quinazolin-5(4H)-one,
2-(3,4-Dihydroisoquinoline-2(1H)-carbonyl)pyrrolo[1,2-a]quinazolin-5(4H)-one,
2-(4-Dimethylaminopiperidine-1-carbonyl)pyrrolo[1,2-a]quinazolin-5(4H)-one,
2-[4-(Pyridin-4-yl)piperazine-1-carbonyl]pyrrolo[1,2-a]quinazolin-5(4H)-one,
2-[4-(4-Fluorophenyl)-2-methylpiperazine-1-carbonyl]pyrrolo[1,2-a]quinazolin-5(4H)-one,
2-[4-(2-Methoxyphenyl)piperazine-1-carbonyl]pyrrolo[1,2-a]quinazolin-5(4H)-one,
2-[4-(3-Methoxyphenyl)piperazine-1-carbonyl]pyrrolo[1,2-a]quinazolin-5(4H)-one,
2-(4-Cyclohexylpiperazine-1-carbonyl)pyrrolo[1,2-a]quinazolin-5(4H)-one,
2-[4-Cyclopropylmethylpiperazine-1-carbonyl]pyrrolo[1,2-a]quinazolin-5(4H)-one,
2-[4-(4-Trifluoromethylphenyl)piperazine-1-carbonyl]pyrrolo[1,2-a]quinazolin-5(4H)-one,
2-[4-(5-Chloropyridin-2-yl)piperazine-1-carbonyl]pyrrolo[1,2-a]quinazolin-5(4H)-one,
2-(3-Phenylpiperidine-1-carbonyl)pyrrolo[1,2-a]quinazolin-5(4H)-one,
2-[4-(3-Methylphenyl)piperazine-1-carbonyl]pyrrolo[1,2-a]quinazolin-5(4H)-one,
2-[4-(Piperidin-1-yl)piperidine-1-carbonyl]pyrrolo[1,2-a]quinazolin-5(4H)-one,
2-(Pyrrolidine-1-carbonyl)pyrrolo[1,2-a]quinazolin-5(4H)-one,
2-[4-(2,4-Difluorophenyl)piperazine-1-carbonyl]pyrrolo[1,2-a]quinazolin-5(4H)-one,
2-[4-(Furo[3,2-c]pyridin-4-yl)piperazine-1-carbonyl]pyrrolo[1,2-a]quinazolin-5(4H)-one,
2-[4-(1H-Indole-4-yl)piperazine-1-carbonyl]pyrrolo[1,2-a]quinazolin-5(4H)-one,
2-[4-(4-Isopropoxyphenyl)piperazine-1-carbonyl]pyrrolo[1,2-a]quinazolin-5(4H)-one,
2-[4-(4-Fluoro-2-methoxyphenyl)piperazine-1-carbonyl]pyrrolo[1,2-a]quinazolin-5(4H)-one,
2-[4-(1,3-Benzodioxol-5-yl)piperazine-1-carbonyl]pyrrolo[1,2-a]quinazolin-5(4H)-one,
7-[4-(4-Fluorophenyl)piperazine-1-carbonyl]pyrrolo[1,2-a]thieno[2,3-e]pyrimidin-4(5H)-one,
7-[4-(4-Chlorophenyl)piperazine-1-carbonyl]pyrrolo[1,2-a]thieno[2,3-e]pyrimidin-4(5H)-one,
7-(Pyrrolidine-1-carbonyl)pyrrolo[1,2-a]thieno[2,3-e]pyrimidin-4(5H)-one,
7-Fluoro-2-[4-(pyridin-2-yl)piperazine-1-carbonyl]pyrrolo[1,2-a]quinazolin-5(4H)-one,
7-Fluoro-2-[4-(4-fluorophenyl)piperazine-1-carbonyl]pyrrolo[1,2-a]quinazolin-5(4H)-one,
2-[4-(4-Fluorophenyl)homopiperazine-1-carbonyl]pyrrolo[1,2-a]quinazolin-5(4H)-one,
2-[4-(tert-Butoxycarbonyl)homopiperazine-1-carbonyl]pyrrolo[1,2-a]quinazolin-5(4H)-one,
2-[4-(tert-Butoxycarbonyl)piperazine-1-carbonyl]pyrrolo[1,2-a]quinazolin-5(4H)-one, 2-(Phenylaminocarbonyl)pyrrolo[1,2-a]quinazolin-5(4H)-one,
2-(4-Methylhomopiperazine-1-carbonyl)pyrrolo[1,2-a]quinazolin-5(4H)-one,
2-[(2-Dimethylaminoethyl)aminocarbonyl]pyrrolo[1,2-a]quinazolin-5(4H)-one,
2-[(Pyridin-4-ylmethyl)aminocarbonyl]pyrrolo[1,2-a]quinazolin-5(4H)-one,
2-[2-(Morpholin-4-ylethyl)aminocarbonyl]pyrrolo[1,2-a]quinazolin-5(4H)-one,
2-(Benzylaminocarbonyl)pyrrolo[1,2-a]quinazolin-5(4H)-one,
2-(2-Phenylethylaminocarbonyl)pyrrolo[1,2-a]quinazolin-5(4H)-one,
2-(3-Phenylpropylaminocarbonyl)pyrrolo[1,2-a]quinazolin-5(4H)-one,
2-[4-[2-(2-Dimethylaminoethoxy)-4-fluorophenyl]piperazine-1-carbonyl]pyrrolo[1,2-a]quinazolin-5(4H)-one,
2-[4-(Morpholin-4-yl)piperidine-1-carbonyl]pyrrolo[1,2-a]quinazolin-5(4H)-one,
2-[4-(4-Fluorophenyl)piperazin-1-ylmethyl]pyrrolo[1,2-a]quinazolin-5(4H)-one,
2-[4-(4-Chlorobenzyl)piperazin-1-ylmethyl]pyrrolo[1,2-a]quinazolin-5(4H)-one,
2-[4-(Thiazol-2-yl)piperazin-1-ylmethyl]pyrrolo[1,2-a]quinazolin-5(4H)-one,
2-(4-Phenylpiperazin-1-ylmethyl)pyrrolo[1,2-a]quinazolin-5(4H)-one,
2-(4-Phenylpiperidin-1-ylmethyl)pyrrolo[1,2-a]quinazolin-5(4H)-one,
2-(4-Phenyl-1,2,3,6-tetrahydropyridin-1-ylmethyl)pyrrolo[1,2-a]quinazolin-5(4H)-one,
2-[4-(4-Chlorophenyl)-1,2,3,6-tetrahydropyridin-1-ylmethyl]pyrrolo[1,2-a]quinazolin-5(4H)-one,
2-[4-(4-Fluorophenyl)-1,2,3,6-tetrahydropyridin-1-ylmethyl]pyrrolo[1,2-a]quinazolin-5(4H)-one,
2-[4-(2-Fluorophenyl)piperazin-1-ylmethyl]pyrrolo[1,2-a]quinazolin-5(4H)-one,
2-(4-Methylpiperazin-1-ylmethyl)pyrrolo[1,2-a]quinazolin-5(4H)-one,
2-(4-Benzylpiperazin-1-ylmethyl)pyrrolo[1,2-a]quinazolin-5(4H)-one,
2-[4-(4-Chlorophenyl)piperazin-1-ylmethyl]pyrrolo[1,2-a]quinazolin-5(4H)-one,
2-[4-(4-Fluorobenzyl)piperazin-1-ylmethyl]pyrrolo[1,2-a]quinazolin-5(4H)-one,
2-[4-(4-Fluorophenyl)piperidin-1-ylmethyl]pyrrolo[1,2-a]quinazolin-5(4H)-one,
2-[4-(3-Fluorophenyl)piperazin-1-ylmethyl]pyrrolo[1,2-a]quinazolin-5(4H)-one,
2-[4-(4-Methoxyphenyl)piperazin-1-ylmethyl]pyrrolo[1,2-a]quinazolin-5(4H)-one,
2-[4-(Pyridin-2-yl)piperazin-1-ylmethyl]pyrrolo[1,2-a]quinazolin-5(4H)-one,
2-[4-(Pyridin-3-yl)piperazin-1-ylmethyl]pyrrolo[1,2-a]quinazolin-5(4H)-one,
2-[N-Methyl-N-(3-phenylpropyl)aminomethyl]pyrrolo[1,2-a]quinazolin-5(4H)-one,
2-[4-(4-Bromophenyl)piperazin-1-ylmethyl]pyrrolo[1,2-a]quinazolin-5(4H)-one,
2-(1,2,3,4-Tetrahydroisoquinolin-2(1H)-ylmethyl)pyrrolo[1,2-a]quinazolin-5(4H)-one,
2-(4-Dimethylaminopiperidin-1-ylmethyl)pyrrolo[1,2-a]quinazolin-5(4H)-one,
2-[4-(Pyridin-4-yl)piperazin-1-yl methyl]pyrrolo[1,2-a]quinazolin-5(4H)-one,
2-[4-(4-Fluorophenyl)-2-methylpiperazin-1-ylmethyl]pyrrolo[1,2-a]quinazolin-5(4H)-one,
2-[4-(2-Methoxyphenyl)piperazin-1-ylmethyl]pyrrolo[1,2-a]quinazolin-5(4H)-one,
2-[4-(3-Methoxyphenyl)piperazin-1-ylmethyl]pyrrolo[1,2-a]quinazolin-5(4H)-one,
2-(4-Cyclohexylpiperazin-1-ylmethyl)pyrrolo[1,2-a]quinazolin-5(4H)-one,
2-(4-Cyclopropylmethylpiperazin-1-ylmethyl)pyrrolo[1,2-a]quinazolin-5(4H)-one,
2-[4-(4-Trifluoromethylphenyl)piperazin-1-ylmethyl]pyrrolo[1,2-a]quinazolin-5(4H)-one,
2-[4-(5-Chloropyridin-2-yl)piperazin-1-ylmethyl]pyrrolo[1,2-a]quinazolin-5(4H)-one,
2-(3-Phenylpiperidin-1-ylmethyl)pyrrolo[1,2-a]quinazolin-5(4H)-one,
2-[4-(3-Methylphenyl)piperazin-1-ylmethyl]pyrrolo[1,2-a]quinazolin-5(4H)-one,
2-[4-(Piperidin-1-yl)piperidin-1-ylmethyl]pyrrolo[1,2-a]quinazolin-5(4H)-one,
2-(Pyrrolidin-1-ylmethyl)pyrrolo[1,2-a]quinazolin-5(4H)-one,
2-[4-(2,4-Difluorophenyl)piperazin-1-ylmethyl]pyrrolo[1,2-a]quinazolin-5(4H)-one,
2-[4-(Furo[3,2-c]pyridin-4-yl)piperazin-1-ylmethyl]pyrrolo[1,2-a]quinazolin-5(4H)-one,
2-[4-(1H-Indol-4-yl)piperazin-1-ylmethyl]pyrrolo[1,2-a]quinazolin-5(4H)-one,
2-[4-(4-Isopropoxyphenyl)piperazin-1-ylmethyl]pyrrolo[1,2-a]quinazolin-5(4H)-one,
2-[4-(4-Fluoro-2-methoxyphenyl)piperazin-1-ylmethyl]pyrrolo[1,2-a]quinazolin-5(4H)-one,
2-[4-(1,3-Benzodioxol-5-yl)piperazin-1-ylmethyl]pyrrolo[1,2-a]quinazolin-5(4H)-one,
7-[4-(4-Fluorophenyl)piperazin-1-ylmethyl]pyrrolo[1,2-a]th1ieno[2,3-e]pyrimidin-4(5H)-one,
7-[4-(4-Chlorophenyl)piperazin-1-ylmethyl]pyrrolo[1,2-a]thieno[2,3-e]pyrimidin-4(5H)-one,
7-(Pyrrolidin-1-ylmethyl)pyrrolo[1,2-a]thieno[2,3-e]pyrimidin-4(5H)-one,
7-Fluoro-2-[4-(pyridin-2-yl)piperazin-1-ylmethyl]pyrrolo[1,2-a]quinazolin-5(4H)-one,
7-Fluoro-2-[4-(4-fluorophenyl)piperazin-1-ylmethyl]pyrrolo[1,2-a]quinazolin-5(4H)-one,
2-[4-[2-(2-Dimethylaminoethoxy)-4-fluorophenyl]piperazin-1-ylmethyl]pyrrolo[1,2-a]quinazolin-5(4H)-one,
2-[4-(Morpholin-4-yl)piperidin-1-ylmethyl]pyrrolo[1,2-a]quinazolin-5(4H)-one,
2-[4-(4-Hydroxyphenyl)piperazin-1-ylmethyl]pyrrolo[1,2-a]quinazolin-5(4H)-one,
2-[1-[4-(4-Fluorophenyl)piperazin-1-yl]-1,1-dideuteriomethyl]pyrrolo[1,2-a]quinazolin-5(4H)-one,
2-(Homopiperazine-1-carbonyl)pyrrolo[1,2-a]quinazolin-5(4H)-one hydrochloride,
2-(piperazine-1-carbonyl)pyrrolo[1,2-a]quinazolin-5(4H)-one, and
2-[4-Cyclopropylcarbonylhomopiperazine-1-carbonyl]pyrrolo[1,2-a]quinazolin-5(4H)-one.

Other aspect of the present invention is a PARP inhibitor consisting of the present compound.

Other aspect of the present invention is a pharmaceutical composition comprising at least one of the present compounds as an active ingredient.

Also, other aspect of the present invention is a prophylactic or therapeutic agent for posterior ocular disease comprising at least one of the present compounds as an active ingredient.

Other aspect of the present invention is a method for inhibiting PARP activity comprising the step of bringing at least one of the present compounds into contact with PARP in vitro or in vivo.

Other aspect of the present invention is a method for prophylaxis or therapy of posterior ocular disease comprising the step of administering a pharmaceutically effective amount of at least one of the present compounds to a patient.

Other aspect of the present invention is the present compound for use in inhibition of PARP activity.

Also, other aspect of the present invention is the present compound for use in prophylaxis or therapy of posterior ocular disease.

Other aspect of the present invention is use of the present compound for manufacturing a PARP inhibitor.

Further, other aspect of the present invention is use of the present compound for manufacturing a prophylactic or therapeutic agent for posterior ocular disease.

Advantageous Effects of Invention

Since the present compound has strong PARP inhibitory activity, it can serve as therapeutic agents for various diseases including posterior ocular disease.

DESCRIPTION OF EMBODIMENTS

Hereinafter, definitions for the wording (atom and group) used in this description will be described in detail. When the following definitions for wording are applied to definition of another wording, a preferred range and a particularly preferred range of the definitions are also applied.

"Halogen atom" represents a fluorine atom, a chlorine atom, a bromine atom or an iodine atom.

"Lower alkyl group" represents a straight or branched alkyl group having 1 to 8, preferably 1 to 6, and particularly preferably 1 to 4 carbon atoms. Specific examples of "lower alkyl group" include a methyl group, an ethyl group, a n-propyl group, a n-butyl group, a n-pentyl group, a n-hexyl group, a n-heptyl group, a n-octyl group, an isopropyl group, an isobutyl group, a sec-butyl group, a tert-butyl group, and an isopentyl group.

"Lower cycloalkyl group" represents a cycloalkyl group having 3 to 10, preferably 3 to 8, and particularly preferably 3 to 6 carbon atoms. Specific examples of "lower cycloalkyl group" include a cyclopropyl group, a cyclobutyl group, a cyclopentyl group, a cyclohexyl group, a cycloheptyl group, a cyclooctyl group, a cyclononanyl group, and a cyclodecanyl group.

"Lower alkoxy group" represents a group formed by replacing a hydrogen atom of a hydroxy group with a lower alkyl group. Specific examples of "lower alkoxy group" include a methoxy group, an ethoxy group, a n-propoxy group, a n-butoxy group, a n-pentoxy group, a n-hexyloxy group, a n-heptyloxy group, a n-octyloxy group, an isopropoxy group, an isobutoxy group, a sec-butoxy group, a tert-butoxy group, and an isopentoxy group.

"Lower alkylcarbonyl group" represents a group formed by replacing a hydrogen atom of a formyl group with a lower alkyl group. Specific examples of "lower alkylcarbonyl group" include a methylcarbonyl group, an ethylcarbonyl group, a n-propylcarbonyl group, a n-butylcarbonyl group, a n-pentylcarbonyl group, a n-hexylcarbonyl group, a n-heptylcarbonyl group, a n-octylcarbonyl group, an isopropylcarbonyl group, an isobutylcarbonyl group, a sec-butylcarbonyl group, a tert-butylcarbonyl group, and an isopentylcarbonyl group.

"Lower cycloalkylcarbonyl group" represents a group formed by replacing a hydrogen atom of a formyl group with a lower cycloalkyl group. Specific examples of "lower cycloalkylcarbonyl group" include a cyclopropylcarbonyl group, a cyclopentylcarbonyl group, a cyclohexylcarbonyl group, a cycloheptylcarbonyl group, a cyclononanylcarbonyl group, and a cyclodecanylcarbonyl group.

"Aryl group" represents a residue formed by removing one hydrogen atom from a monocyclic aromatic hydrocarbon or bicyclic or tricyclic condensed polycyclic aromatic hydrocarbon having 6 to 14 carbon atoms. Specific examples of "aryl group" include a phenyl group, a naphthyl group, an anthryl group, and a phenanthryl group, and among these, a phenyl group is particularly preferred.

"Lower alkylamino group" represents a group formed by replacing one or both of hydrogen atoms of an amino group with a lower alkyl group. Specific examples of "lower alkylamino group" include a methylamino group, an ethylamino group, a propylamino group, a dimethylamino group, and an ethyl(methyl)amino group.

"Lower cycloalkylamino group" represents a group formed by replacing one or both of hydrogen atoms of an amino group with a lower cycloalkyl group. Specific examples of "lower cycloalkylamino group" include a cyclopropylamino group, a cyclobutylamino group, a cyclopentylamino group, a cyclohexylamino group, and a cyclohexyl(methyl)amino group.

"Lower alkylaminocarbonyl group" represents a group formed by replacing a hydrogen atom of a formyl group with a lower alkylamino group. Specific examples of "lower alkylaminocarbonyl group" include a methylaminocarbonyl group, an ethylaminocarbonyl group, a propylaminocarbonyl group, a dimethylaminocarbonyl group, a diethylaminocarbonyl group, and an ethyl(methyl)aminocarbonyl group.

"Lower cycloalkylaminocarbonyl group" represents a group formed by replacing a hydrogen atom of a formyl group with a lower cycloalkylamino group. Specific examples of "lower cycloalkylaminocarbonyl group" include a cyclopropylaminocarbonyl group, a cyclobutylaminocarbonyl group, a cyclopentylaminocarbonyl group, a cyclohexylaminocarbonyl group, a cycloheptylaminocarbonyl group, a cyclooctylaminocarbonyl group, a dicyclohexylaminocarbonyl group, and a cyclohexyl(methyl)aminocarbonyl group.

"Lower alkoxycarbonyl group" represents a group formed by replacing a hydrogen atom of a formyl group with by a lower alkoxy group. Specific examples thereof include a methoxycarbonyl group, an ethoxycarbonyl group, a n-propoxycarbonyl group, a n-butoxycarbonyl group, a n-pentoxycarbonyl group, a n-hexyloxycarbonyl group, a n-heptyloxycarbonyl group, a n-octyloxycarbonyl group, an isopropoxycarbonyl group, an isobutoxycarbonyl group, a sec-butoxycarbonyl group, a tert-butoxycarbonyl group, and an isopentoxycarbonyl group.

"Heterocyclic ring" represents a saturated or unsaturated heteromonocyclic ring, or heterobicyclic or heterotricyclic ring having one or plural heteroatoms selected from a nitrogen atom, an oxygen atom and a sulfur atom in the ring.

As "saturated heteromonocyclic ring" in the present invention, 3 to 8-membered saturated heteromonocyclic ring having 1 to 3 heteroatoms and 2 to 5 carbon atoms in the ring is preferred, and 5 to 7-membered saturated heteromonocyclic ring having 1 to 3 heteroatoms and 3 to 5 carbon atoms in the ring is particularly preferred. Specific examples of "saturated heteromonocyclic ring" include a pyrrolidine ring, a pyrazolidine ring, an imidazolidine ring, a triazolidine ring, a piperidine ring, a hexahydropyridazine ring, a hexahydropyrimidine ring, a piperazine ring, a homopiperidine ring, and a homopiperazine ring having a nitrogen atom in the ring; a tetrahydrofuran ring, and a tetrahydropyran ring having an oxygen atom in the ring; a tetrahydrothiophene ring, and a tetrahydrothiopyran ring having a sulfur atom in the ring; an oxazolidine ring, an isoxazolidine ring, and a morpholine ring having a nitrogen atom and an oxygen atom in the ring; and a thiazolidine ring, an isothiazolidine ring and a thiomorpholine ring having a nitrogen atom and a sulfur atom in the ring.

As "unsaturated heteromonocyclic ring" in the present invention, 3 to 8-membered unsaturated heteromonocyclic ring having 1 to 3 heteroatoms and 2 to 5 carbon atoms in the ring is preferred, and 5 to 7-membered unsaturated heteromonocyclic ring having 1 to 3 heteroatoms and 3 to 5 carbon atoms in the ring is particularly preferred. Specific examples of "unsaturated heteromonocyclic ring" include a pyrrole ring, a dihydropyrrole ring, a pyrazole ring, a dihydropyrazole ring, an imidazole ring, a dihydroimidazole ring, a triazole ring, a dihydrotriazole ring, a pyridine ring, a dihydropyridine ring, a tetrahydropyridine ring, a pyridazine ring, a dihydropyridazine ring, a tetrahydropyridazine ring, a pyrimidine ring, a dihydropyrimidine ring, a tetrahydropyrimidine ring, a pyrazine ring, a dihydropyrazine ring, and a tetrahydropyrazine ring having a nitrogen atom in the ring; a dihydrofuran ring, a furan ring, a dihydropyran ring, and a pyran ring having an oxygen atom in the ring; a dihydrothiophene ring, a thiophene ring, a dihydrothiopyran ring, and a thiopyran ring having a sulfur atom in the ring; an oxazole ring, a dihydrooxazole ring, an isoxazole ring, a dihydroisoxazole ring, an oxazine ring, and a dihydrooxazine ring having a nitrogen atom and an oxygen atom in the ring; and a thiazole ring, a dihydrothiazole ring, an isothiazole ring, a dihydroisothiazole ring, a thiazine ring, and a dihydrothiazine ring having a nitrogen atom and a sulfur atom in the ring.

As "heterobicyclic ring" or "heterotricyclic ring" in the present invention, a bicyclic or tricyclic condensed heteropolycyclic ring having 1 to 3 heteroatoms and 7 to 13 carbon atoms in the ring is preferred. "Heterobicyclic ring" or "heterotricyclic ring" is formed by condensation of the aforementioned saturated or unsaturated heteromonocyclic ring with a benzene ring or the like, and specific examples thereof include an indole ring, a dihydroindole ring, an indazole ring, a dihydroindazole ring, a benzoimidazole ring, a dihydrobenzoimidazole ring, a benzotriazole ring, a quinoline ring, a dihydroquinoline ring, a tetrahydroquinoline ring, an isoquinoline ring, a dihydroisoquinoline ring, a tetrahydroisoquinoline ring, a cinnoline ring, a dihydrocinnoline ring, a tetrahydrocinnoline ring, a phthalazine ring, a dihydrophthalazine ring, a tetrahydrophthalazine ring, a quinazoline ring, a dihydroquinazoline ring, a tetrahydroquinazoline ring, a quinoxaline ring, a dihydroquinoxaline ring, a tetrahydroquinoxaline ring, a phenanthridine ring, a carbazole ring, a β-carboline ring, an acridine ring, a phenanthroline ring, a phenazine ring, and a perimidine ring having a nitrogen atom in the ring; a benzofuran ring, a dihydrobenzofuran ring, an isobenzofuran ring, a dihydroisobenzofuran ring, a chromene ring, an isochromene ring, a chromane ring, an isochromane ring, and a xanthene ring having an oxygen atom in the ring; a benzothiophene ring, a dihydrobenzothiophene ring, an isobenzothiophene ring, a dihydroisobenzothiophene ring, a thiochromane ring, an isothiochromane ring, a thiochromene ring, and an isothiochromene ring having a sulfur atom in the ring; a benzoxazole ring, a dihydrobenzoxazole ring, a benzisoxazole ring, a dihydrobenzisoxazole ring, a benzoxazine ring, a dihydrobenzoxazine ring, a furo[3,2-c]pyridine ring, and a phenoxazine ring having a nitrogen atom and an oxygen atom in the ring; and a benzothiazole ring, a dihydrobenzothiazole ring, a benzisothiazole ring, a dihydrobenzisothiazole ring, a benzothiazine ring, a dihydrobenzothiazine ring, a phenoxanthine ring, and a phenothiazine ring having a nitrogen atom and a sulfur atom in the ring.

"Nitrogen-containing heterocyclic ring" represents those having one or plural nitrogen atoms in the ring among the heterocyclic rings as recited above, and a nitrogen-containing heteromonocyclic ring or a nitrogen-containing heterobicyclic ring is preferred.

"Nitrogen-containing heteromonocyclic ring" represents preferably a 3 to 8-membered nitrogen-containing heteromonocyclic ring having 1 to 3 nitrogen atoms and 2 to 5 carbon atoms in the ring, and particularly preferably a 5 to 7-membered nitrogen-containing heteromonocyclic ring having 1 to 3 nitrogen atoms and 3 to 5 carbon atoms in the ring. Specific examples thereof include those exemplified as the above "unsaturated or saturated heteromonocyclic ring having a nitrogen atom in the ring", the above "unsaturated or saturated heteromonocyclic ring having a nitrogen atom and an oxygen atom in the ring", and the above "unsaturated or saturated heteromonocyclic ring having a nitrogen atom and a sulfur atom in the ring". A preferred specific example of "nitrogen-containing heteromonocyclic ring" in the present invention is a pyrrolidine ring, a piperidine ring, a tetrahydropyridine ring (1,2,3,6-tetrahydropyridine ring or the like), a piperazine ring or a homopiperazine ring.

"Nitrogen-containing heterobicyclic ring" represents a bicyclic condensed heteropolycyclic ring having preferably 1 to 3 heteroatoms and 7 to 9 carbon atoms in the ring, and specific examples thereof include those exemplified as the above "heterobicyclic ring having a nitrogen atom in the ring", the above "heterobicyclic ring having a nitrogen atom and an oxygen atom in the ring", and the above "heterobicyclic ring having a nitrogen atom and a sulfur atom in the ring". A preferred concrete example of "nitrogen-containing heterobicyclic ring" in the present invention is a tetrahydroisoquinoline ring (1,2,3,4-tetrahydroisoquinoline ring).

"Heterocyclic group" represents a residue formed by removing one hydrogen atom from the above heterocyclic ring. As "heterocyclic group" in the present invention, "heteromonocyclic group" which is a residue formed by removing one hydrogen atom from "3 to 8-membered saturated or unsaturated heteromonocyclic ring having 1 to 3 heteroatoms and 2 to 5 carbon atoms in the ring" is preferred, and "heteromonocyclic group" which is a residue formed by removing one hydrogen atom from "5 to 7-membered saturated or unsaturated heteromonocyclic ring having 1 to 3 hetero atoms and 3 to 5 carbon atoms in the ring" is particularly preferred. Also, "heterobicyclic group" which is a residue formed by removing one hydrogen atom from "bicyclic condensed heteropolycyclic ring having 1 to 3 heteroatoms and 7 to 9 carbon atoms in the ring" is removed is also preferred as "heterocyclic group" in the present invention.

Preferred specific examples of "heteromonocyclic group" in the present invention include thiazole groups (e.g., thiazol 2-yl group), pyridyl groups (e.g., 2-pyridyl group, 3-pyridyl group, 4-pyridyl group), piperidyl groups (e.g., 1-piperidyl group), and morphonyl groups (e.g., morpholin-4-yl group (morpholino group)).

Preferred specific examples of "heterobicyclic group" in the present invention include indolyl groups (e.g., 1H-indol-4-yl group), a furo[3,2-c]pyridin-4-yl group, and a 1,3-benzodioxol-5yl group.

"Lower alkyl group optionally having a substituent" represents "lower alkyl group" which may have one or plural substituents selected from the group consisting, for example, of a deuterium atom, a halogen atom, a lower cycloalkyl group, an aryl group, an aryl group substituted by a halogen atom, a heterocyclic group, a hydroxy group, a lower alkoxy group and a lower alkoxy group substituted by a lower alkylamino group, and preferably represents "lower alkyl group" which may have one or plural substituents selected from the group consisting of a lower cycloalkyl group (e.g., cyclopropyl group), an aryl group (e.g., phenyl group), an aryl group substituted by a halogen atom (e.g., chlorophenyl group, fluorophenyl group) and a heterocyclic group (e.g., pyridyl group, morphonyl group).

"Lower cycloalkyl group optionally having a substituent" represents a "lower cycloalkyl group" which may have one or plural substituents selected from the group consisting, for example, of a deuterium atom, a halogen atom, a lower alkyl group, a lower alkyl group substituted by a halogen atom, a lower cycloalkyl group, an aryl group, an aryl group substituted by a halogen atom, a heterocyclic group, a hydroxy group, a lower alkoxy group and a lower alkoxy group substituted by a lower alkylamino group.

"Aryl group optionally having a substituent" represents "aryl group" which may have one or plural substituents selected from the group consisting, for example, of a deuterium atom, a halogen atom, a lower alkyl group, a lower alkyl group substituted by a halogen atom, a lower cycloalkyl group, an aryl group, an aryl group substituted by a halogen atom, a heterocyclic group, a hydroxy group, a lower alkoxy group and a lower alkoxy group substituted by a lower alkylamino group, and preferably represents "aryl group" which may have one or plural substituents selected from the group consisting of a halogen atom (e.g., fluorine atom, chlorine atom, bromine atom), a lower alkyl group (e.g., methyl group), a lower alkyl group substituted by a halogen atom (e.g., trifluoromethyl group), a hydroxy group, a lower alkoxy group (e.g., methoxy group, isopropoxy group) and a lower alkoxy group substituted by a lower alkylamino group (e.g., dimethylaminoethoxy group).

"Heterocyclic group optionally having a substituent" represents "heterocyclic group" which may have one or plural substituents selected from the group consisting, for example, of a deuterium atom, a halogen atom, a lower alkyl group, a lower alkyl group substituted by a halogen atom, a lower cycloalkyl group, an aryl group, an aryl group substituted by a halogen atom, a heterocyclic group, a hydroxy group, a lower alkoxy group and a lower alkoxy group substituted by a lower alkylamino group, and preferably represents "heterocyclic group" which may be substituted by one or plural halogen atoms (e.g., chlorine atom).

"Lower alkoxy group optionally having a substituent", "lower alkylcarbonyl group optionally having a substituent", "lower cycloalkylcarbonyl group optionally having a substituent", "lower alkylaminocarbonyl group optionally having a substituent", "lower cycloalkylaminocarbonyl group optionally having a substituent" and/or "a lower alkoxycarbonyl group optionally having a substituent" each represent "lower alkoxy group", "lower alkylcarbonyl group", "lower cycloalkylcarbonyl group", "lower alkylaminocarbonyl group", "lower cycloalkylaminocarbonyl group" and/or "lower alkoxycarbonyl group" which may have one or plural substituents selected from the group consisting, for example, of a deuterium atom, a halogen atom, a lower alkyl group, a lower alkyl group substituted by a halogen atom, a lower cycloalkyl group, an aryl group, an aryl group substituted by a halogen atom, a heterocyclic group, a hydroxy group, a lower alkoxy group and a lower alkoxy group substituted by a lower alkylamino group.

As to "plural substituents" in the present invention, the substituent groups may be the same or different, and the substitution sites may be the same or different. The above "plural substituents" represent preferably two or three substituent groups, and particularly preferably two substituent groups.

(A) Examples of the present compound include a compound in which respective groups are the groups as shown below or a salt thereof in the compounds represented by the following general formula (1) or salts thereof.

[Chemical Formula 6]

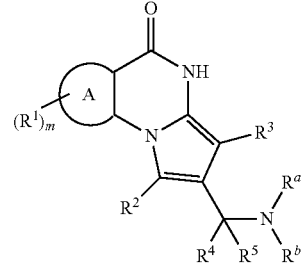

(1)

(A1) $R^1$ represents a halogen atom, a lower alkyl group, a hydroxy group, a lower alkoxy group, an amino group, a nitro group or a cyano group; and/or (A2) $R^2$ and $R^3$ may be the same or different and each represent a hydrogen atom, a halogen atom or a lower alkyl group; and/or (A3) $R^4$ and $R^5$ may be the same or different and each represent a hydrogen atom, a deuterium atom or a lower alkyl group, or $R^4$ and $R^5$ may form an oxo group; and/or (A4) $R^a$ and $R^b$ may be the same or different and each represent a hydrogen atom, a lower alkyl group optionally having a substituent or an aryl group optionally having a substituent; and/or (A5) $R^a$ and $R^b$ may bind to each other to form a nitrogen-containing heterocyclic ring which may be substituted by one or plural $R^c$; and/or (A6) $R^c$ represents a lower alkyl group optionally having a substituent, a lower cycloalkyl group optionally having a substituent, an aryl group optionally having a substituent, a heterocyclic group optionally having a substituent, a hydroxy group, a lower alkoxy group optionally having a substituent, a lower alkylcarbonyl group optionally having a substituent, a lower cycloalkylcarbonyl group optionally having a substituent, a lower alkylaminocarbonyl group optionally having a substituent, a lower cycloalkylaminocarbonyl group optionally having a substituent, a lower alkoxycarbonyl group optionally having a substituent, an amino group, a lower alkylamino group or a carboxyl group;

(A7) ring A represents a benzene ring or an unsaturated heteromonocyclic ring; and/or (A8) m represents 0, 1 or 2.

In other words, the present compound is a compound having one or more than one combinations selected from the group consisting of the above (A1), (A2), (A3), (A4), (A5), (A6), (A7) and (A8) or a salt thereof in the compounds represented by the general formula (1) or salts thereof.

(B) Preferred examples of the present compound include a compound in which respective groups are the groups shown below or a salt thereof in the compounds represented by the general formula (1) or salts thereof.

(B1) $R^1$ represents a halogen atom or a lower alkyl group; and/or (B2) $R^2$ and $R^3$ may be the same or different and each represent a hydrogen atom, a halogen atom or a lower alkyl group; and/or (B3) $R^4$ and $R^5$ may be the same or different and each represent a hydrogen atom, a deuterium atom or a lower alkyl group, or $R^4$ and $R^5$ may form an oxo group; and/or (B4) $R^a$ and $R^b$ may be the same or different and each represent a hydrogen atom, a lower alkyl group or an aryl group, and the lower alkyl group or the aryl group may be substituted by a deuterium atom, an aryl group, a heterocyclic group, an amino group or a lower alkylamino group; and/or (B5) $R^a$ and $R^b$ may bind to each other to form a nitrogen-containing heterocyclic ring which may be substituted by one or plural $R^c$; and/or (B6) $R^c$ represents a lower alkyl group, a lower cycloalkyl group, an aryl group, a heterocyclic group, a hydroxy group, a lower alkoxy group, a lower alkylcarbonyl group, a lower cycloalkylcarbonyl group, a lower alkylaminocarbonyl group, a lower cycloalkylaminocarbonyl group, a lower alkoxycarbonyl group, an amino group, a lower alkylamino group or a carboxyl group, and the lower alkyl group, the lower cycloalkyl group, the aryl group, the heterocyclic group, and the lower alkoxy group, the lower alkylcarbonyl group, the lower cycloalkylcarbonyl group, the lower alkylaminocarbonyl group, the lower cycloalkylaminocarbonyl group, the lower alkoxycarbonyl group or the lower alkylamino group may be substituted by one or plural groups selected from the group consisting of a deuterium atom, a halogen atom, a lower alkyl group, a lower alkyl group substituted by a halogen atom, a lower cycloalkyl group, an aryl group, an aryl group substituted by a halogen atom, a heterocyclic group, a hydroxy group, a lower alkoxy group and a lower alkoxy group substituted by a lower alkylamino group; and/or (B7) ring A represents a benzene ring or a 5-membered unsaturated heteromonocyclic ring; and/or (B8) m represents 0 or 1.

In other words, the present compound is preferably a compound having one or more than one combinations selected from the group consisting of the above (B1), (B2), (B3), (B4), (B5), (B6), (B7) and (B8) or a salt thereof in the compounds represented by the general formula (1) or salts thereof.

(C) Preferred examples of the present compound include a compound in which respective groups are the groups shown below or a salt thereof in the compounds represented by the general formula (1) or salts thereof.

(C1) $R^1$ represents a halogen atom or a lower alkyl group;

(C2) $R^2$ and $R^3$ each represent a hydrogen atom;

(C3) $R^4$ and $R^5$ may be the same or different and each represent a hydrogen atom, a deuterium atom or a lower alkyl group, or $R^4$ and $R^5$ may form an oxo group;

(C4) $R^a$ and $R^b$ may be the same or different and each represent a hydrogen atom, a lower alkyl group or an aryl group, and the lower alkyl group or the aryl group may be substituted by an aryl group, a heterocyclic group, an amino group or a lower alkylamino group;

(C5) $R^a$ and $R^b$ may bind to each other to form a nitrogen-containing heteromonocyclic ring or a nitrogen-containing heterobicyclic ring which may be substituted by one or plural $R^c$;

(C6) $R^c$ represents a lower alkyl group, a lower cycloalkyl group, an aryl group, a heterocyclic group, a hydroxy group, a lower alkoxy group, a lower alkylcarbonyl group, a lower cycloalkylcarbonyl group, a lower alkylaminocarbonyl group, a lower cycloalkylaminocarbonyl group, a lower alkoxycarbonyl group, an amino group, a lower alkylamino group or a carboxyl group, and the lower alkyl group, the lower cycloalkyl group, the aryl group, the heterocyclic group, the lower alkoxy group, the lower alkylcarbonyl group, the lower cycloalkylcarbonyl group, the lower alkylaminocarbonyl group, the lower cycloalkylaminocarbonyl group, the lower alkoxycarbonyl group or the lower alkylamino group may be substituted by one or plural groups selected from the group consisting of a halogen atom, a lower alkyl group, a lower alkyl group substituted by a halogen atom, a lower cycloalkyl group, an aryl group, an aryl group substituted by a halogen atom, a hydroxy group, a lower alkoxy group and a lower alkoxy group substituted by a lower alkylamino group, (C7) ring A represents a benzene ring or a 5-membered unsaturated heteromonocyclic ring; and (C8) m represents 0 or 1.

In other words, the present compound is preferably a compound having one or more than one combinations selected from the group consisting of the above (C1), (C2), (C3), (C4), (C5), (C6), (C7) and (C8) or a salt thereof in the compounds represented by the general formula (1) or salts thereof.

(D) Preferred examples of the present compound include a compound in which $R^a$ and $R^b$ in the general formula (1) may be the same or different and each represent a hydrogen atom, a lower alkyl group or a phenyl group, or salts thereof, and in this case, the lower alkyl group may be substituted by a phenyl group, a pyridyl group, a morphonyl group, an amino group or a dimethylamino group.

Compounds satisfying the condition (D) and the conditions (A), (B) and/or (C) or salts thereof are more preferred as the present compound.

(E) Preferred examples of the present compound include a compound in which $R^a$ and $R^b$ in the general formula (1) bind to each other to form a nitrogen-containing heterocyclic ring represented by the following formula (2a) or (3a), or a salt thereof.

[Chemical Formula 7]

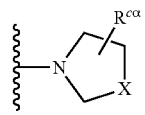

(2a)

[Chemical Formula 8]

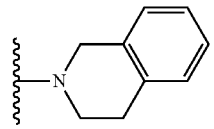

(3a)

In this case, X represents $CH_2$, $CH_2CHR^{c\beta}$, $CH=CR^{c\beta}$, $CH_2NR^{c\beta}$ or $CH_2CH_2NR^{c\beta}$;

$R^{c\alpha}$ represents a hydrogen atom, a halogen atom, a lower alkyl group or a phenyl group; and $R^{c\beta}$ represents a hydrogen atom, a lower alkyl group, a lower cycloalkyl group, an aryl group, a heteromonocyclic group, a heterobicyclic group, a lower alkoxycarbonyl group, a lower cycloalkylcarbonyl group or a lower alkylamino group, and the lower alkyl group, the lower cycloalkyl group, the aryl group, the heteromonocyclic group, the heterobicyclic group, the lower alkoxycarbonyl group or the lower cycloalkylcarbonyl group may be substituted by one or plural groups selected from the group consisting of a halogen atom, a lower alkyl group, a lower alkyl group substituted by a halogen atom, a lower cycloalkyl group, an aryl group, an aryl group substituted by a halogen atom, a hydroxy group, a lower alkoxy group and a lower alkoxy group substituted by a lower alkylamino group.

In this condition (E), the nitrogen-containing heterocyclic ring is more preferably a nitrogen-containing heterocyclic ring represented by the above formula (2a).

In this condition (E), $R^{c\alpha}$ is particularly preferably a hydrogen atom, a halogen atom, a methyl group or a phenyl group.

In this condition (E), X is preferably $CH_2CHR^{c\beta}$, $CH=CR^{c\beta}$ or $CH_2NR^{c\beta}$.

In this condition (E), $R^{c\beta}$ is preferably a hydrogen atom, a lower alkyl group, a lower cycloalkyl group, an aryl group, a heteromonocyclic group, a heterobicyclic group, a lower alkoxycarbonyl group, a lower cycloalkylcarbonyl group or a lower alkylamino group, and in this case, the lower alkyl group, the lower cycloalkyl group, the aryl group, the heteromonocyclic group, the heterobicyclic group, the lower alkoxycarbonyl group or the lower cycloalkylcarbonyl group may be substituted by one or plural groups selected from the group consisting of a halogen atom, a lower alkyl group, a lower alkyl group substituted by a halogen atom, a lower cycloalkyl group, an aryl group, an aryl group substituted by a halogen atom, a hydroxy group, a lower alkoxy group and a lower alkoxy group substituted by a lower alkylamino group.

In this condition (E), $R^{c\beta}$ is particularly preferably a hydrogen atom, a methyl group, a cyclohexyl group, a phenyl group, a pyridyl group, a piperidyl group, a thiazole group, a morphonyl group, an indolyl group, a furo[3,2-c]pyridin-4-yl group, a 1,3-benzodioxol-5-yl group, an ethoxycarbonyl group, a cyclopropylcarbonyl group or a dimethylamino group, and in this case, the methyl group, the cyclohexyl group, the phenyl group, the pyridyl group, the piperidyl group, the thiazole group, the morphonyl group, the indolyl group, the furo[3,2-c]pyridin-4-yl group or the 1,3-benzodioxol-5-yl group may be substituted by one or plural groups selected from the group consisting of a halogen atom, a lower alkyl group, a lower alkyl group substituted by a halogen atom, a lower cycloalkyl group, a phenyl group, a phenyl group substituted by a halogen atom, a hydroxy group, a lower alkoxy group and a lower alkoxy group substituted by a dimethylamino group.

Further, particularly preferably, in this condition (E), in the above formula (2a), $R^{c\alpha}$ represents a hydrogen atom, X represents $CH_2NR^{c\beta}$, and $R^{c\beta}$ represents a phenyl group which may be substituted by one or plural groups selected from the group consisting of a halogen atom, a lower alkyl group, a hydroxy group and a lower alkoxy group.

Compounds satisfying the condition (E) and the conditions (A), (B) and/or (C) or salts thereof are more preferred as the present compound.

(F) Preferred examples of the present compound include a compound in which $R^1$ in the general formula (1) is a halogen atom, or a salt thereof.

Compounds satisfying the condition (F) and the conditions (A), (B) and/or (C) or salts thereof are more preferred as the present compound.

(G) Preferred examples of the present compound include a compound in which $R^2$ and $R^3$ in the general formula (1) is a hydrogen atom, or a salt thereof.

Compounds satisfying the condition (G) and the conditions (A), (B) and/or (C) or salts thereof are more preferred as the present compound.

(H) Preferred examples of the present compound include a compound in which $R^4$ and $R^5$ in the general formula (1) is a hydrogen atom, or a salt thereof.

Compounds satisfying the condition (H) and the conditions (A), (B) and/or (C) or salts thereof are more preferred as the present compound.

(I) Preferred examples of the present compound include a compound in which ring A in the general formula (1) is a benzene ring or an unsaturated heteromonocyclic ring represented by the following formula (4a), or a salt thereof.

[Chemical Formula 9]

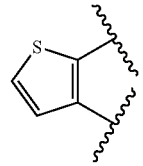

(4a)

Compounds satisfying the condition (I) and the conditions (A), (B) and/or (C) or salts thereof are more preferred as the present compound.

(J) Preferred specific examples of the present compound include the following compounds or salts thereof.
2-[4-(4-Fluorophenyl)piperazine-1-carbonyl]pyrrolo[1,2-a]quinazolin-5(4H)-one (later-described "Compound 1-1"),
2-[4-(4-Chlorobenzyl)piperazine-1-carbonyl]pyrrolo[1,2-a]quinazolin-5(4H)-one (later-described "Compound 1-2"),
2-[4-(Tthiazol-2-yl)piperazine-1-carbonyl]pyrrolo[1,2-a]quinazolin-5(4H)-one (later-described "Compound 1-3"),
2-(4-Phenylpiperazine-1-carbonyl)pyrrolo[1,2-a]quinazolin-5(4H)-one (later-described "Compound 1-4"),
2-(4-Phenylpiperidine-1-carbonyl)pyrrolo[1,2-a]quinazolin-5(4H)-one (later-described "Compound 1-5"),
2-(4-Phenyl-1,2,3,6-tetrahydropyridine-1-carbonyl)pyrrolo[1,2-a]quinazolin-5(4H)-one (later-described "Compound 1-6"),
2-[4-(4-Chlorophenyl)-1,2,3,6-tetrahydropyridine-1-carbonyl]pyrrolo[1,2-a]quinazolin-5(4H)-one (later-described "Compound 1-7"),
2-[4-(4-Fluorophenyl)-1,2,3,6-tetrahydropyridine-1-carbonyl]pyrrolo[1,2-a]quinazolin-5 (4H)-one (later-described "Compound 1-8"),
2-[4-(2-Fluorophenyl)piperazine-1-carbonyl]pyrrolo[1,2-a]quinazolin-5(4H)-one (later-described "Compound 1-9"),
2-(4-Methylpiperazine-1-carbonyl)pyrrolo[1,2-a]quinazolin-5(4H)-one (later-described "Compound 1-10"),
2-(4-Benzylpiperazine-1-carbonyl)pyrrolo[1,2-a]quinazolin-5(4H)-one (later-described "Compound 1-11"),
2-[4-(4-Chlorophenyl)piperazine-1-carbonyl]pyrrolo[1,2-a]quinazolin-5(4H)-one (later-described "Compound 1-12"),
2-[4-(4-Fluorobenzyl)piperazine-1-carbonyl]pyrrolo[1,2-a]quinazolin-5(4H)-one (later-described "Compound 1-13"),
2-[4-(4-Fluorophenyl)piperidine-1-carbonyl]pyrrolo[1,2-a]quinazolin-5(4H)-one (later-described "Compound 1-14"),
2-[4-(3-Fluorophenyl)piperazine-1-carbonyl]pyrrolo[1,2-a]quinazolin-5(4H)-one (later-described "Compound 1-15"),
2-[4-(4-Methoxyphenyl)piperazine-1-carbonyl]pyrrolo[1,2-a]quinazolin-5(4H)-one (later-described "Compound 1-16"),
2-[4-(Pyridin-2-yl)piperazine-1-carbonyl]pyrrolo[1,2-a]quinazolin-5 (4H)-one (later-described "Compound 1-17"), 2-[4-(Pyridin-3-yl)piperazine-1-carbonyl]pyrrolo[1,2-a]quinazolin-5(4H)-one (later-described "Compound 1-18"), 2-[N-Methyl-N-(3-phenylpropyl)aminocarbonyl]pyrrolo[1,2-a]quinazolin-5(4H)-one (later-described "Compound 1-19"), 2-[4-(4-Bromophenyl)piperazine-1-carbonyl]pyrrolo[1,2-a]quinazolin-5(4H)-one (later-described "Compound 1-20"), 2-(3,4-Dihydroisoquinoline-2(1H)-carbonyl)pyrrolo[1,2-a]quinazolin-5(4H)-one (later-described "Compound 1-21"), 2-(4-Dimethylaminopiperidine-1-carbonyl)pyrrolo[1,2-a]quinazolin-5(4H)-one (later-described "Compound 1-22"), 2-[4-(Pyridin-4-yl)piperazine-1-carbonyl]pyrrolo[1,2-a]quinazolin-5(4H)-one (later-described "Compound 1-23"), 2-[4-(4-Fluorophenyl)-2-methylpiperazine-1-carbonyl]pyrrolo[1,2-a]quinazolin-5(4H)-one (later-described "Compound 1-24"), 2-[4-(2-Methoxyphenyl)piperazine-1-carbonyl]pyrrolo[1,2-a]quinazolin-5(4H)-one (later-described "Compound 1-25"), 2-[4-(3-Methoxyphenyl)piperazine-1-carbonyl]pyrrolo[1,2-a]quinazolin-5(4H)-one (later-described "Compound 1-26"), 2-(4-Cyclohexylpiperazine-1-carbonyl)pyrrolo[1,2-a]quinazolin-5(4H)-one (later-described "Compound 1-27"), 2-[4-Cyclopropylmethylpiperazine-1-carbonyl]pyrrolo[1,2-a]quinazolin-5(4H)-one (later-described "Compound 1-28"), 2-[4-(4-Trifluoromethylphenyl)piperazine-1-carbonyl]pyrrolo[1,2-a]quinazolin-5(4H)-one (later-described "Compound 1-29"), 2-[4-(5-Chloropyridin-2-yl)piperazine-1-carbonyl]pyrrolo[1,2-a]quinazolin-5(4H)-one (later-described "Compound 1-30"), 2-(3-Phenylpiperidine-1-carbonyl)pyrrolo[1,2-a]quinazolin-5(4H)-one (later-described "Compound 1-31"), 2-[4-(3-Methylphenyl)piperazine-1-carbonyl]pyrrolo[1,2-a]quinazolin-5(4H)-one (later-described "Compound 1-32"), 2-[4-(Piperidin-1-yl)piperidine-1-carbonyl]pyrrolo[1,2-a]quinazolin-5(4H)-one (later-described "Compound 1-33"), 2-(Pyrrolidine-1-carbonyl)pyrrolo[1,2-a]quinazolin-5(4H)-one (later-described "Compound 1-34"), 2-[4-(2,4-Difluorophenyl)piperazine-1-carbonyl]pyrrolo[1,2-a]quinazolin-5(4H)-one (later-described "Compound 1-35"), 2-[4-(Furo[3,2-c]pyridin-4-yl)piperazine-1-carbonyl]pyrrolo[1,2-a]quinazolin-5(4H)-one (later-described "Compound 1-36"), 2-[4-(1H-Indol-4-yl)piperazine-1-carbonyl]pyrrolo[1,2-a]quinazolin-5(4H)-one (later-described "Compound 1-37"), 2-[4-(4-Isopropoxyphenyl)piperazine-1-carbonyl]pyrrolo[1,2-a]quinazolin-5(4H)-one (later-described "Compound 1-38"), 2-[4-(4-Fluoro-2-methoxyphenyl)piperazine-1-carbonyl]pyrrolo[1,2-a]quinazolin-5(4H)-one (later-described "Compound 1-39"), 2-[4-(1,3-Benzodioxol-5-yl)piperazine-1-carbonyl]pyrrolo[1,2-a]quinazolin-5(4H)-one (later-described "Compound 1-40"), 7-[4-(4-Fluorophenyl)piperazine-1-carbonyl]pyrrolo[1,2-a]thieno[2,3-e]pyrimidin-4(5H)-one (later-described "Compound 1-41"), 7-[4-(4-Chlorophenyl)piperazine-1-carbonyl]pyrrolo[1,2-a]thieno[2,3-e]pyrimidin-4(5H)-one (later-described "Compound 1-42"), 7-(Pyrrolidine-1-carbonyl)pyrrolo[1,2-a]thieno[2,3-e]pyrimidin-4(5H)-one (later-described "Compound 1-43"), 7-Fluoro-2-[4-(pyridin-2-yl)piperazine-1-carbonyl]pyrrolo[1,2-a]quinazolin-5(4H)-one (later-described "Compound 1-44"), 7-Fluoro-2-[4-(4-fluorophenyl)piperazine-1-carbonyl]pyrrolo[1,2-a]quinazolin-5(4H)-one (later-described "Compound 1-45"), 2-[4-(4-Fluorophenyl)homopiperazine-1-carbonyl]pyrrolo[1,2-a]quinazolin-5(4H)-one (later-described "Compound 1-46"), 2-[4-(tert-Butoxycarbonyl)homopiperazine-1-carbonyl]pyrrolo[1,2-a]quinazolin-5(4H)-one (later-described "Compound 1-47"), 2-[4-(tert-Butoxycarbonyl)piperazine-1-carbonyl]pyrrolo[1,2-a]quinazolin-5(4H)-one (later-described "Compound 1-48"), 2-(Phenylaminocarbonyl)pyrrolo[1,2-a]quinazolin-5(4H)-one (later-described "Compound 1-49"), 2-(4-Methylhomopiperazine-1-carbonyl)pyrrolo[1,2-a]quinazolin-5(4H)-one (later-described "Compound 1-50"), 2-[(2-Dimethylaminoethyl)aminocarbonyl]pyrrolo[1,2-a]quinazolin-5(4H)-one (later-described "Compound 1-51"), 2-[(Pyridin-4-ylmethyl)aminocarbonyl]pyrrolo[1,2-a]quinazolin-5(4H)-one (later-described "Compound 1-52"), 2-[2-(Morpholin-4-ylethyl)aminocarbonyl]pyrrolo[1,2-a]quinazolin-5(4H)-one (later-described "Compound 1-53"), 2-(Benzylaminocarbonyl)pyrrolo[1,2-a]quinazolin-5(4H)-one (later-described "Compound 1-54"), 2-(2-Phenylethylaminocarbonyl)pyrrolo[1,2-a]quinazolin-5(4H)-one (later-described "Compound 1-55"), 2-(3-Phenylpropylaminocarbonyl)pyrrolo[1,2-a]quinazolin-5(4H)-one (later-described "Compound 1-56"), 2-[4-[2-(2-Dimethylaminoethoxy)-4-fluorophenyl]piperazine-1-carbonyl]pyrrolo[1,2-a]quinazolin-5(4H)-one (later-described "Compound 1-57"), 2-[4-(Morpholin-4-yl)piperidine-1-carbonyl]pyrrolo[1,2-a]quinazolin-5(4H)-one (later-described "Compound 1-58"), 2-[4-(4-Fluorophenyl)piperazin-1-ylmethyl]pyrrolo[1,2-a]quinazolin-5(4H)-one (later-described "Compound 2-1"), 2-[4-(4-Chlorobenzyl)piperazin-1-ylmethyl]pyrrolo[1,2-a]quinazolin-5(4H)-one (later-described "Compound 2-2"), 2-[4-(Thiazol-2-yl)piperazin-1-ylmethyl]pyrrolo[1,2-a]quinazolin-5(4H)-one (later-described "Compound 2-3"), 2-(4-Phenylpiperazin-1-ylmethyl)pyrrolo[1,2-a]quinazolin-5(4H)-one (later-described "Compound 2-4"), 2-(4-Phenylpiperidin-1-ylmethyl)pyrrolo[1,2-a]quinazolin-5(4H)-one (later-described "Compound 2-5"), 2-(4-Phenyl-1,2,3,6-tetrahydropyridin-1-ylmethyl)pyrrolo[1,2-a]quinazolin-5(4H)-one (later-described "Compound 2-6"), 2-[4-(4-Chlorophenyl)-1,2,3,6-tetrahydropyridine-1-ylmethyl]pyrrolo[1,2-a]quinazolin-5(4H)-one (later-described "Compound 2-7"), 2-[4-(4-Fluorophenyl)-1,2,3,6-tetrahydropyridin-1-ylmethyl]pyrrolo[1,2-a]quinazolin-5(4H)-one (later-described "Compound 2-8"),
2-[4-(2-Fluorophenyl)piperazin-1-ylmethyl]pyrrolo[1,2-a]quinazolin-5(4H)-one (later-described "Compound 2-9"),
2-(4-Methylpiperazin-1-ylmethyl)pyrrolo[1,2-a]quinazolin-5(4H)-one (later-described "Compound 2-10"),
2-(4-Benzylpiperazin-1-ylmethyl)pyrrolo[1,2-a]quinazolin-5(4H)-one (later-described "Compound 2-11"),
2-[4-(4-Chlorophenyl)piperazin-1-ylmethyl]pyrrolo[1,2-a]quinazolin-5(4H)-one (later-described "Compound 2-12"),
2-[4-(4-Fluorobenzyl)piperazin-1-ylmethyl]pyrrolo[1,2-a]quinazolin-5(4H)-one (later-described "Compound 2-13"),
2-[4-(4-Fluorophenyl)piperidin-1-ylmethyl]pyrrolo[1,2-a]quinazolin-5(4H)-one (later-described "Compound 2-14"),
2-[4-(3-Fluorophenyl)piperazin-1-ylmethyl]pyrrolo[1,2-a]quinazolin-5(4H)-one (later-described "Compound 2-15"),
2-[4-(4-Methoxyphenyl)piperazin-1-ylmethyl]pyrrolo[1,2-a]quinazolin-5(4H)-one (later-described "Compound 2-16"),
2-[4-(Pyridin-2-yl)piperazin-1-ylmethyl]pyrrolo[1,2-a]quinazolin-5(4H)-one (later-described "Compound 2-17"),
2-[4-(Pyridine-3-yl)piperazin-1-ylmethyl]pyrrolo[1,2-a]quinazolin-5(4H)-one (later-described "Compound 2-18"),
2-[N-Methyl-N-(3-phenylpropyl)aminomethyl]pyrrolo[1,2-a]quinazolin-5(4H)-one (later-described "Compound 2-19"),
2-[4-(4-Bromophenyl)piperazin-1-ylmethyl]pyrrolo[1,2-a]quinazolin-5(4H)-one (later-described "Compound 2-20"),
2-(1,2,3,4-Tetrahydroisoquinolin-2(1H)-ylmethyl)pyrrolo[1,2-a]quinazolin-5(4H)-one (later-described "Compound 2-21"),
2-(4-Dimethylaminopiperidin-1-ylmethyl)pyrrolo[1,2-a]quinazolin-5(4H)-one (later-described "Compound 2-22"),
2-[4-(Pyridin-4-yl)piperazin-1-ylmethyl]pyrrolo[1,2-a]quinazolin-5(4H)-one (later-described "Compound 2-23"),
2-[4-(4-Fluorophenyl)-2-methylpiperazin-1-ylmethyl]pyrrolo[1,2-a]quinazolin-5(4H)-one (later-described "Compound 2-24"),
2-[4-(2-Methoxyphenyl)piperazin-1-ylmethyl]pyrrolo[1,2-a]quinazolin-5(4H)-one (later-described "Compound 2-25"),
2-[4-(3-Methoxyphenyl)piperazin-1-ylmethyl]pyrrolo[1,2-a]quinazolin-5(4H)-one (later-described "Compound 2-26"),
2-(4-Cyclohexylpiperazin-1-ylmethyl)pyrrolo[1,2-a]quinazolin-5(4H)-one (later-described "Compound 2-27"),
2-(4-Cyclopropylmethylpiperazin-1-ylmethyl)pyrrolo[1,2-a]quinazolin-5(4H)-one (later-described "Compound 2-28"),
2-[4-(4-Trifluoromethylphenyl)piperazin-1-ylmethyl]pyrrolo[1,2-a]quinazolin-5(4H)-one (later-described "Compound 2-29"),
2-[4-(5-Chloropyridin-2-yl)piperazin-1-ylmethyl]pyrrolo[1,2-a]quinazolin-5(4H)-one (later-described "Compound 2-30"),
2-(3-Phenylpiperidin-1-ylmethyl)pyrrolo[1,2-a]quinazolin-5(4H)-one (later-described "Compound 2-31"),
2-[4-(3-Methylphenyl)piperazin-1-ylmethyl]pyrrolo[1,2-a]quinazolin-5(4H)-one (later-described "Compound 2-32"),
2-[4-(Piperidin-1-yl)piperidin-1-ylmethyl]pyrrolo[1,2-a]quinazolin-5(4H)-one (later-described "Compound 2-33"),
2-(Pyrrolidin-1-ylmethyl)pyrrolo[1,2-a]quinazolin-5(4H)-one (later-described "Compound 2-34"),
2-[4-(2,4-Difluorophenyl)piperazin-1-ylmethyl]pyrrolo[1,2-a]quinazolin-5(4H)-one (later-described "Compound 2-35"),
2-[4-(Furo[3,2-c]pyridin-4-yl)piperazin-1-ylmethyl]pyrrolo[1,2-a]quinazolin-5(4H)-one (later-described "Compound 2-36"),
2-[4-(1H-Indole-4-yl)piperazin-1-ylmethyl]pyrrolo[1,2-a]quinazolin-5(4H)-one (later-described "Compound 2-37"),
2-[4-(4-Isopropoxyphenyl)piperazin-1-ylmethyl]pyrrolo[1,2-a]quinazolin-5(4H)-one (later-described "Compound 2-38"),
2-[4-(4-Fluoro-2-methoxyphenyl)piperazin-1-ylmethyl]pyrrolo[1,2-a]quinazolin-5(4H)-one (later-described "Compound 2-39"),
2-[4-(1,3-Benzodioxol-5-yl)piperazin-1-ylmethyl]pyrrolo[1,2-a]quinazolin-5(4H)-one (later-described "Compound 2-40"),
7-[4-(4-Fluorophenyl)piperazin-1-ylmethyl]pyrrolo[1,2-a]thieno[2,3-e]pyrimidin-4(5H)-one (later-described "Compound 2-41"),
7-[4-(4-Chlorophenyl)piperazin-1-ylmethyl]pyrrolo[1,2-a]thieno[2,3-e]pyrimidin-4(5H)-one (later-described "Compound 2-42"),
7-(Pyrrolidin-1-ylmethyl)pyrrolo[1,2-a]thieno[2,3-e]pyrimidin-4(5H)-one (later-described "Compound 2-43"),
7-Fluoro-2-[4-(pyridin-2-yl)piperazin-1-ylmethyl]pyrrolo[1,2-a]quinazolin-5(4H)-one (later-described "Compound 2-44"),
7-Fluoro-2-[4-(4-fluorophenyl)piperazin-1-ylmethyl]pyrrolo[1,2-a]quinazolin-5(4H)-one (later-described "Compound 2-45"),
2-[4-[2-(2-Dimethylaminoethoxy)-4-fluorophenyl]piperazin-1-ylmethyl]pyrrolo[1,2-a]quinazolin-5(4H)-one (later-described "Compound 2-46"),
2-[4-(Morpholin-4-yl)piperidin-1-ylmethyl]pyrrolo[1,2-a]quinazolin-5(4H)-one (later-described "Compound 2-47"),
2-[4-(4-Hydroxyphenyl)piperazin-1-ylmethyl]pyrrolo[1,2-a]quinazolin-5(4H)-one (later-described "Compound 3-1"),
2-[1-[4-(4-Fluorophenyl)piperazin-1-yl]-1,1-dideuteriomethyl]pyrrolo[1,2-a]quinazolin-5(4H)-one (later-described "Compound 4-1"),
2-(Homopiperazine-1-carbonyl)pyrrolo[1,2-a]quinazolin-5(4H)-one hydrochloride (later-described "Compound 5-1"),
2-(piperazine-1-carbonyl)pyrrolo[1,2-a]quinazolin-5(4H)-one (later-described "Compound 5-2"),
2-[4-Cyclopropylcarbonylhomopiperazine-1-carbonyl]pyrrolo[1,2-a]quinazolin-5(4H)-one (later-described "Compound 6-1").

The present compound can be produced by the following method. Individual concrete production methods will be described in detail in the later-described section of Examples [Production Examples]. These exemplifications are given for better understanding of the present invention, and are not intended to limit the scope of the present invention. X in the following synthetic routes represents a halogen atom.

The present compound can be synthesized according to Synthetic route 1. Specifically, by reacting Compound (2) with amine (3) in an organic solvent such as methylene chloride or N,N-dimethylformamide (hereinafter, "DMF") in the presence of a base such as diisopropylethylamine (hereinafter, "DIEA") at room temperature to 100° C. for 1 hour to 24 hours, the present compound can be obtained.

[Chemical Formula 10]

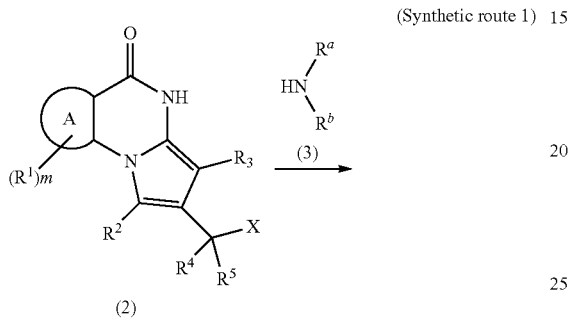

(Synthetic route 1)

(2)

(1)

The present compound (1a) (compound in which $R^4$ and $R^5$ each are a hydrogen atom in the general formula (1)) can be synthesized according to Synthetic route 2. Specifically, the present compound (1a) can be obtained by reacting the present compound (1c) ($R^4$ and $R^5$ represent an oxo group in the general formula (1)) in an organic solvent such as tetrahydrofuran (hereinafter, "THF") in the presence of a reducing agent such as lithium aluminum hydride (hereinafter, "LAH") at room temperature to 70° C. for 1 hour to 24 hours,

[Chemical Formula 11]

(Synthetic route 2)

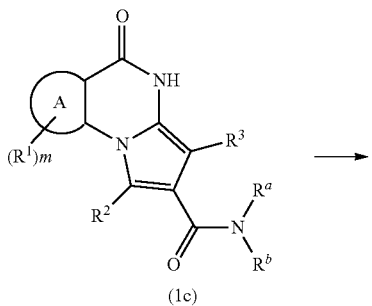

(1c)

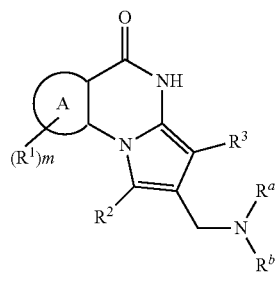

(1a)

The present compound (1b) (compound in which $R^4$ and $R^5$ each are a deuterium atom in the general formula (1)) can be synthesized according to Synthetic route 3. Specifically, the present compound (1b) can be obtained by reacting the present compound (1c) in an organic solvent such as THF in the presence of a reducing agent such as lithium aluminum deuteride at room temperature to 70° C. for 1 hour to 24 hours.

[Chemical Formula 12]

(Synthetic route 3)

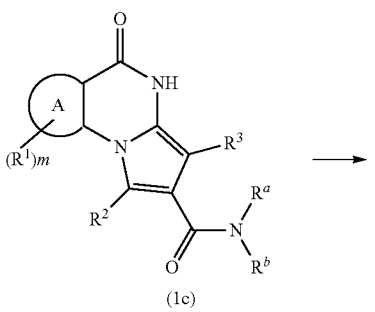

(1c)

(1b)

The present compound (1c) (compound in which $R^4$ and $R^5$ form an oxo group in the general formula (1)) can be synthesized according to Synthetic route 4. Specifically, the present compound (1c) can be obtained by reacting Compound (4) with amine (3) in an organic solvent such as DMF in the presence of a base such as DIEA and a condensing agent such as O-(6-chlorobenzotriazole-1-yl)-N,N,N',N'-tetramethyluronium hexafluorophosphate (hereinafter, "HCTU") at room temperature to 70° C. for 1 hour to 24 hours.

[Chemical Formula 13]

(Synthetic route 4)

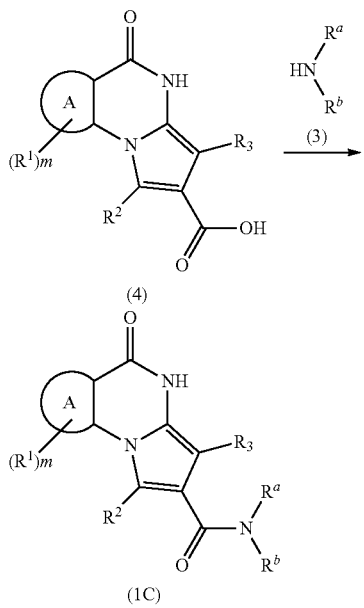

(4)

(1C)

Compound (2) can be synthesized according to Synthetic route 5. Specifically, Compound (2) can be obtained by reacting Compound (5) in an organic solvent such as 1,4-dioxane in the presence of a halogenating agent such as phosphorus tribromide or thionyl chloride at 0° C. to room temperature for 30 minutes to 3 hours.

[Chemical Formula 14]

(Synthetic route 5)

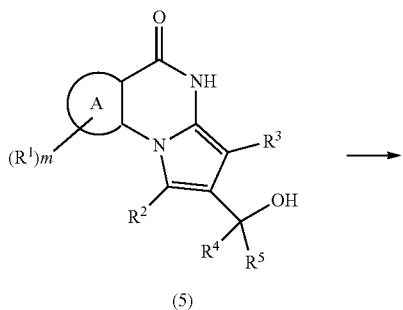

X = Br, Cl (2)

Compound (5) can be synthesized according to Synthetic route 6. Specifically, Compound (5) can be obtained by reacting Compound (6) in an organic solvent such as THF in the presence of a reducing agent such as LAH or an alkylating agent such as methyl lithium or methyl magnesium chloride at room temperature to 70° C. for 3 hours to 24 hours.

[Chemical Formula 15]

(Synthetic route 6)

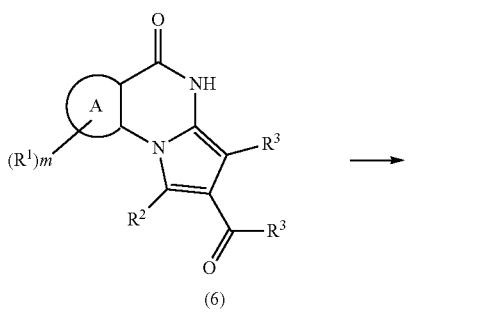

(6)

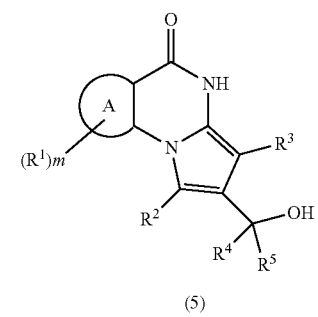

(5)

Compound (6) (in the general formula (6), $R^4$ represents a hydrogen atom or a lower alkyl group) can be synthesized according to Synthetic route 7. That is, Compound (6) can be obtained by reacting Compound (7) in an organic solvent such as THF in the presence of a reducing agent such as LAH or an alkylating agent such as methyl magnesium chloride at room temperature for 3 hours to 24 hours. Compound (7) can be obtained from Compound (4) and methoxymethylamine hydrochloride according to Synthetic route 4.

[Chemical Formula 16]

(Synthetic route 7)

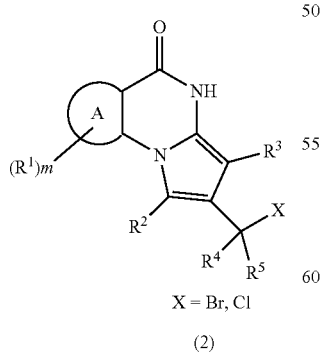

(7)

-continued

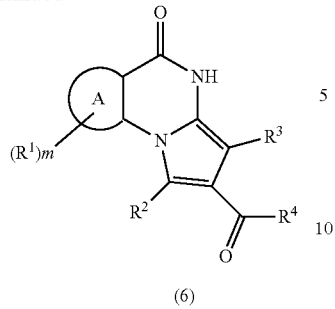

(6)

Compound (4) can be synthesized according to Synthetic route 8. Specifically, Compound (4) can be obtained by treating Compound (8) in a strong acid such as 47% hydrobromic acid at 100° C. for 3 hours to 24 hours.

[Chemical Formula 17]

(Synthetic route 8)

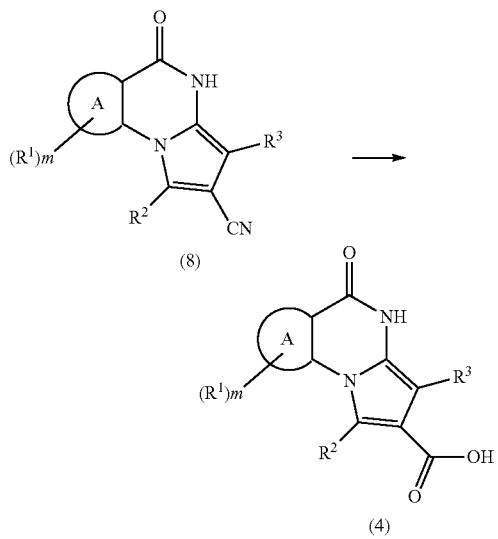

Compound (8) for use in Synthetic route 8 can be synthesized according to Synthetic route 9. Specifically, Compound (9) can be obtained by reacting potassium salt (11) (Z. Chem. 1961, 1, 349) and the corresponding amine (10) in a mixed solution of water and acetic acid at 100° C. for 10 minutes to 30 minutes. Compound (8) can be obtained by reacting the obtained Compound (9) in an organic solvent such as ethanol in the presence of a base such as sodium ethoxide at room temperature for 1 hour to 3 hours.

[Chemical Formula 18]

(Synthetic route 9)

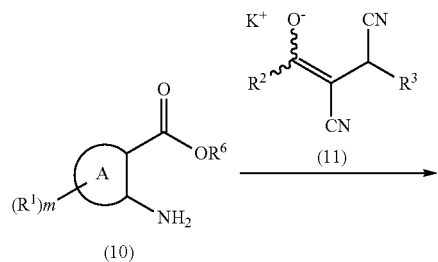

-continued

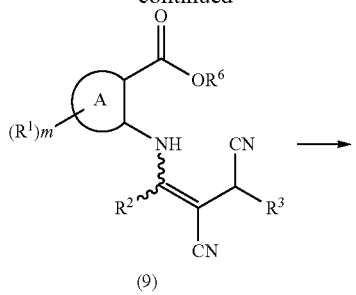

(9)

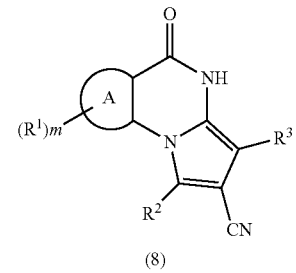

(8)

Various amines (3) for use in Synthetic routes 1 and 4 and amine (10) for use in Synthetic route 9 were commercially available compounds or prepared by a general synthesis procedure known from literature. Concrete preparation methods will be described in detail in the later-described section of Examples [Production Examples].

When the present compound has geometric isomers or optical isomers, such isomers are also involved in the scope of the present invention. The present compound may be in the form of a hydrate or a solvate.

When the present compound has proton tautomerism, such tautomers are also involved in the present invention.

When the present compound has crystal polymorphs and a crystal polymorphic group (crystal polymorphic system), such crystal polymorphs and crystal polymorphic group (crystal polymorphic system) are also involved in the present invention. The crystal polymorphic group (crystal polymorphic system) used herein means crystal forms in respective stages when the crystal form changes depending on the conditions such as production, crystallization, storage and the like of the crystal and the states thereof (including the formulated state) and the entire process.

"Salt" in the present compound is not particularly limited as far as it is a pharmaceutically acceptable salt, and examples thereof include salts with inorganic acids such as hydrochloric acid, hydrobromic acid, hydroiodic acid, nitric acid, sulfuric acid, and phosphoric acid; salts with organic acids such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate ester, methyl sulfate, naphthalenesulfonate, and sulfosalicylic acid; quaternary ammonium salts with methyl bromide, methyl iodide and so on; salts with halogen ions such as bromine ion, chlorine ion and iodine ion; salts with alkaline metals such as lithium, sodium and potassium; salts with alkaline earth metals such as calcium and magnesium; metal salts with iron, zinc and so on; salts with ammonia; and salts with organic amines such as triethylenediamine, 2-aminoethanol, 2,2-iminobis(ethanol), 1-deoxy-1-

(methylamino)-2-D-sorbitol, 2-amino-2-(hydroxymethyl)-1,3-propanediol, procaine, N,N-bis(phenylmethyl)-1,2-ethanediamine and so on.

In the present invention, "PARP" means "poly(ADP ribose) polymerase". PARP includes various isoforms such as PARP1 and PARP2, and these isoforms are also involved in "PARP" in the present invention.

In the present invention, "PARP inhibitor" means the one that inhibits activity of the PARP. As will be described in detail in the section of "Pharmacological test" in later-described Examples, PARP inhibitory activity of the present compound can be easily measured by using Universal Colorimetric PARP Assay kit with Histone-Coated Strip Wells (available from Trevigen, Cat No. 4677-096-K).

In the present invention, "pharmaceutical composition" means a composition usable as a medicine.

The pharmaceutical composition comprising the present compound as an active ingredient can be used for prophylaxis or therapy of, for example, posterior ocular diseases such as age-related macular degeneration (including early age-related maculopathy, atrophic age-related macular degeneration and exudative age-related macular degeneration), diabetic retinopathy, diabetic macular edema, cone dystrophy, cancer-related retinopathy, retinitis pigmentosa, proliferative vitreoretinopathy, retinal artery occlusion, retinal vein occlusion, uveitis, Leber disease, retinopathy of prematurity, retinal detachment, detachment of retinal pigment epithelium, central serous chorioretinopathy, central exudative chorioretinopathy, polypoidal choroidal vasculopathy, multiple choroiditis, neovascular maculopathy, retinal artery macroaneurysm, optic nerve disorder caused by these diseases, optic nerve disorder caused by glaucoma, glaucomatous visual field constriction, ischemic optic neuropathy and the like; anterior ocular diseases such as dry eye, superficial punctate keratopathy, corneal epithelial defect, corneal erosion, corneal ulcer, conjunctival epithelial defect, keratoconjunctivitis sicca, superior limbic keratoconjunctivitis, filamentous keratoconjunctivitis, infectious keratitis, noninfectious keratitis, infectious conjunctivitis, noninfectious conjunctivitis, blepharitis, xerophthalmia, allergic conjunctivitis, anterior uveitis and the like; anterior eye inflammation after surgery; inflammation due to eye tissue transplant rejection and so on, although the use application thereof is not particularly limited.

Pharmaceutical compositions comprising the present compound as an active ingredient can be used as therapeutic drugs for tumor and metastasis thereof (including an adjuvant in cancer treatment or a potentiator for therapy by ionizing radiation or a chemotherapeutic agent); therapeutic drugs for neurodegenerative disease and neurogenic disorder caused by ischemia, injury or massive hemorrhage, or neurodegenerative diseases and neurogenic disorders such as apoplexy or head injury, epilepsy, Alzheimer's disease, Parkinson's disease, Huntington's disease and the like; therapeutic drugs for immunodeficiency or rheumatic disorder or rheumatoid arthritis; therapeutic drugs for inflammations such as sepsis; therapeutic drugs for cardiac disorder after ischemic heart disease; therapeutic drugs for severely stenosed coronary artery or severely stenosed peripheral artery; drugs for therapy of acute myocardial infarction or damage during and after medical solution or mechanical solution; therapeutic drugs for diabetes mellitus; therapeutic drugs for sepsis of multiple tissue failure and acute respiratory distress syndrome; therapeutic drugs for renal disorder after renal ischemia; therapeutic drugs for use during or after renal transplantation; and so on.

As will be described in detail in the section of "Pharmacological test" in later-described Examples, the present compound is useful particularly as a prophylactic or therapeutic drug for posterior ocular disease, and specific examples of the posterior ocular disease on which the present compound is particularly useful include age-related macular degeneration, retinitis pigmentosa, retinal detachment, diabetic macular edema, retinal vein occlusion and detachment of retinal pigment epithelium.

The present compound may be administered orally or parenterally. As dosage forms, tablet, capsule, granule, powder, injection, ophthalmic solution, suppository, transdermal preparation, ointment, aerosol (including inhalant) and the like are recited, and they can be formulated by using commonly used techniques.

For example, oral preparations such as tablet, capsule, granule and powder may be prepared by using required amounts of excipients such as lactose, mannitol, starch, crystalline cellulose, light anhydrous silicic acid, calcium carbonate, and calcium hydrogen phosphate, lubricants such as stearic acid, magnesium stearate and talc; binders such as starch, hydroxypropyl cellulose, hydroxypropylmethyl cellulose, and polyvinylpyrrolidone; disintegrants such as carboxymethylcellulose, low-substituted hydroxypropylmethyl cellulose, and calcium citrate; coating agents such as hydroxypropylmethyl cellulose, macrogol, and silicone resin; stabilizers such as ethyl paraoxybenzoate, and benzyl alcohol; flavoring agents such as sweetener, acidulant and flavor; and so on as required.

Parenteral preparations such as injection and ophthalmic solution may be prepared by using required amounts of tonicity agents such as sodium chloride, concentrated glycerin, propylene glycol, polyethylene glycol, potassium chloride, sorbitol, and mannitol; buffers such as sodium phosphate, sodium hydrogen phosphate, sodium acetate, citric acid, glacial acetic acid, and trometamol; surfactants such as polysorbate 80, polyoxy 40 stearate and polyoxyethylene 60 hydrogenated castor oil; stabilizers such as sodium citrate and sodium edetate; preservatives such as benzalkonium chloride, paraben, benzethonium chloride, paraoxybenzoic acid ester, sodium benzoate, chlorobutanol, and sorbic acid; pH adjusters such as hydrochloric acid, citric acid, phosphoric acid, glacial acetic acid, sodium hydroxide, sodium carbonate, and sodium hydrogen carbonate; soothing agents such as benzyl alcohol; and so on as required.

The dose of the present compound can be appropriately selected depending on the symptom, age, dosage form and the like. For example, an oral preparation may be administered in a dose of typically 0.01 to 1000 mg, preferably 1 to 100 mg per day in a single dose or in several doses. An eye drop may be administered in a concentration of typically 0.0001% to 10% (w/v), and preferably 0.01% to 5% (w/v) in a single dose or in several doses.

EXAMPLES

In the following, Production Examples, Formulation Examples and results of a pharmacological test of the present compound will be shown. It is to be noted that these exemplifications are given for better understanding of the present invention, and are not intended to limit the scope of the present invention.

Production Examples

Reference Example 1

2-Formylsuccinonitrile Potassium Salt (E Isomer/Z Isomer Mixture) (Reference Compound 1-1)

In a solution of succinonitrile (27.5 g, 0.344 mol) and ethyl formate (33 mL, 0.410 mol) in toluene (230 mL)/t-butanol (46 mL), a solution of potassium t-butoxide (39.3 g, 0.350 mol) in t-butanol (300 mL) was added under cooling on ice. The reaction solution was stirred at room temperature for 2 hours. The precipitated solid was collected by filtration, and washed with ethanol (50 mL) and t-butylmethylether (100 mL). By drying under reduced pressure at 80° C., title Reference Compound 1-1 (49.3 g, yield: 98%) was obtained as a pale brown solid (see Z. Chem. 1961, 1, 349).

TABLE 1

| | $^1$H-NMR (400 MHz, DMSO-$d_6$) δ 3.06 (s, 2H), 8.28 (s, 1H). |
|---|---|

Reference Example 2

2-(2,3-Dicyanopropen-1-ylamino)benzoic acid methyl ester (E isomer/Z isomer mixture) (Reference Compound 2-1)

In a solution of 2-formylsuccinonitrile potassium salt (E isomer/Z isomer mixture) (Reference Compound 1-1, 32.8 g, 0.224 mmol) and anthranilic acid methyl ester (33.0 mL, 0.225 mmol) in water (100 mL), acetic acid (100 mL) was added, and the reaction solution was stirred at 100° C. for 10 minutes. After the reaction solution was allowed to cool to room temperature, the precipitated solid was collected by filtration, and washed with water and ethanol. The obtained solid was dried under reduced pressure, to obtain title Reference Compound 2-1 (40.1 g, yield: 74%) as a brown solid (see Z. Chem. 1961, 1, 349).

TABLE 2

| | $^1$H-NMR (400 MHz, DMSO-$d_6$) δ 3.70 (d, J = 0.7 Hz, 2H), 3.90 (s, 3H), 7.06-7.13 (m, 1H), 7.44 (d, J = 8.3 Hz, 1H), 7.58-7.67 (m, 1H), 7.94-7.80 (m, 1H), 8.10-8.20 (m, 1H), 10.30 (d, J = 12.4 Hz, 1H). |
|---|---|

In the following, by using 3-aminothiophene-2-carboxylic acid methyl ester, and 2-amino-5-fluorobenzoic acid methyl ester, Reference Compounds 2-2 and 2-3 were obtained according to the production method for Reference Compound 2-1.

TABLE 3

| 3-(2,3-Dicyanopropen-1-ylamino)thiophene-2-carboxylic acid methyl ester (E isomer/Z isomer mixture) (Reference Compound 2-2) 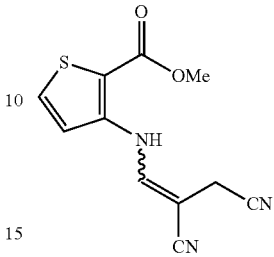 | $^1$H-NMR (400 MHz, DMSO-$d_6$) δ 3.63 (s, 2H), 3.84 (s, 3H), 7.31 (d, J = 5.6 Hz, 1H), 7.94 (d, J = 5.6 Hz, 1H), 8.08 (d, J = 13.4 Hz, 1H), 9.65 (d, J = 13.4 Hz, 1H). |
|---|---|
| 2-(2,3-Dicyanopropen-1-ylamino)-5-fluorobenzoic acid methyl ester (E isomer/Z isomer mixture) (Reference Compound 2-3) 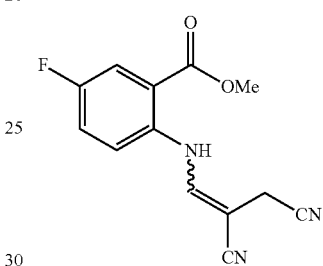 | $^1$H-NMR (400 MHz, DMSO-$d_6$) δ 3.64 (s, 2H), 3.91 (s, 3H), 7.49 (dd, J = 9.3, 4.5 Hz, 1H), 7.60 (td, J = 9.3, 3.2 Hz, 1H), 7.71 (dd, J = 9.3, 3.2 Hz, 1H), 8.14 (d, J = 13.0 Hz, 1H), 10.51 (d, J = 13.0 Hz, 1H). |

Reference Example 3

5-oxo-4,5-dihydropyrrolo[1,2-a]quinazoline-2-carbonitrile (Reference Compound 3-1)

Under cooling on ice, in a solution of 2-(2,3-dicyanopropen-1-ylamino)benzoic acid methyl ester (E isomer/Z isomer mixture) (Reference Compound 2-1, 40.1 g, 0.166 mol) in ethanol (700 mL), a solution of sodium ethoxide (28.2 g, 0.414 mol) in ethanol (300 mL) was added dropwise. After stirring the reaction solution at room temperature for 2 hours, 1M hydrochloric acid (500 mL) was added under cooling on ice. The precipitated solid was collected by filtration, and washed with water. By drying under reduced pressure, the title Reference Compound (33.8 g, yield: 97%) was obtained as a colorless powder (see Z. Chem. 1961, 1, 349).

TABLE 4

| | $^1$H-NMR (400 MHz, DMSO-$d_6$) δ 5.95 (d, J = 1.7 Hz, 1H), 7.52 (ddd, J = 7.3, 7.0, 0.7 Hz, 1H), 7.87 (ddd, J = 7.3, 7.0, 1.5 Hz, 1H), 8.10 (dd, J = 7.3, 0.7 Hz, 1H), 8.14 (dd, J = 7.0, 1.5 Hz, 1H), 8.52 (d, J = 1.7 Hz, 1H), 11.98(s, 1H). |
|---|---|

In the following, by using Reference Compounds 2-2 and 2-3, Reference Compounds 3-2 and 3-3 were obtained according to the production method for Reference Compound 3-1.

TABLE 5

| | |
|---|---|
| 4-Oxo-4,5-dihydropyrrolo[1,2-a]thieno[2,3-e]pyrimidine-7-carbonitrile (Reference Compound 3-2) 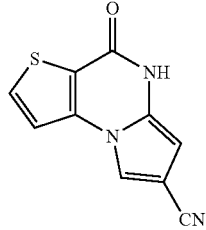 [SMILES: N#Cc1cc2[nH]c(=O)c3sccc3n2c1] | $^1$H-NMR (400 MHz, DMSO-$d_6$) δ 5.99 (d, J = 1.7 Hz, 1H), 7.81 (d, J = 5.4 Hz, 1H), 8.27 (d, J = 5.4 Hz, 1H), 8.32 (d, J =1.7 Hz, 1H), 12.07 (s, 1H). |
| 7-Fluoro-5-oxo-4,5-dihydropyrrolo[1,2-a]quinazoline-2-carbonitrile (Reference Compound 3-3) 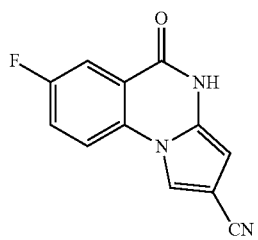 [SMILES: N#Cc1cc2[nH]c(=O)c3cc(F)ccc3n2c1] | $^1$H-NMR (400 MHz, DMSO-$d_6$) δ 5.96 (d, J = 1.8 Hz, 1H), 7.80 (td, J = 8.9, 2.9 Hz, 1H), 7.84 (dd, J = 8.9, 2.9 Hz, 1H), 8.18 (dd, J = 8.9, 4.3 Hz, 1H), 8.52 (d, J = 1.8Hz, 1H), 12.14 (s, 1H). |

Reference Example 4

5-oxo-4,5-dihydropyrrolo[1,2-a]quinazoline-2-carboxylic acid (Reference Compound 4-1)

A solution of 5-oxo-4,5-dihydropyrrolo[1,2-a]quinazoline-2-carbonitrile (Reference Compound 3-1, 33.8 g, 0.162 mol) in 47% hydrobromic acid (400 mL) was stirred at 100° C. for 4 hours. The reaction solution was allowed to cool to room temperature, and water (1.0 L) was added. The precipitated solid was collected by filtration, and dried at 80° C. under reduced pressure, to obtain title Reference Compound 4-1 (36.2 g, yield: 98%) as a brown powder.

TABLE 6

| | |
|---|---|
| 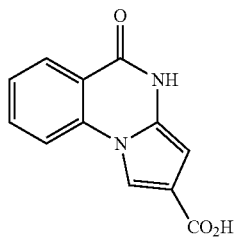 [SMILES: O=C(O)c1cc2[nH]c(=O)c3ccccc3n2c1] | $^1$H-NMR (400 MHz, DMSO-$d_6$) δ 5.86 (s, 1H), 7.47 (t, J = 7.3 Hz, 1H), 7.81 (t, J = 7.3 Hz, 1H), 8.13 (d, J = 7.3 Hz, 1H), 8.20 (d, J = 7.3 Hz, 1H), 8.22 (s, 1H), 11.80 (s, 1H), 12.30 (brs, 1H). |

In the following, by using Reference Compounds 3-2 and 3-3, Reference Compounds 4-2 and 4-3 were obtained according to the production method for Reference Compound 4-1.

TABLE 7

| | |
|---|---|
| 4-Oxo-4,5-dihydropyrrolo[1,2-a]thieno[2,3-e]pyrimidine-7-carboxylic acid (Reference Compound 4-2) 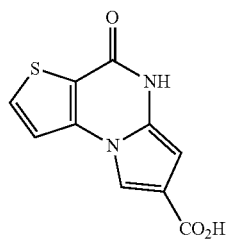 [SMILES: O=C(O)c1cc2[nH]c(=O)c3sccc3n2c1] | $^1$H-NMR (400 MHz, DMSO-$d_6$) δ 5.89 (d, J = 1.8 Hz, 1H), 7.92 (d, J = 5.1 Hz, 1H), 8.08 (d, J = 1.8 Hz, 1H), 8.23 (d, J = 5.1 Hz, 1H), 11.86 (s, 1H). |
| 7-Fluoro-5-oxo-4,5-dihydropyrrolo[1,2-a]quinazoline-2-carboxylic acid (Reference Compound 4-3) 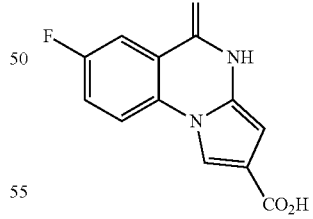 | $^1$H-NMR (400 MHz, DMSO-$d_6$) δ 5.87 (d, J = 1.8 Hz, 1H), 7.72 (td, J = 8.8, 3.1 Hz, 1H), 7.81 (dd, J = 8.8, 3.1 Hz, 1H), 8.24 (d, J = 1.8 Hz, 1H), 8.29 (dd, J = 8.8, 4.4 Hz, 1H), 11.95 (s, 1H), 12.29 (s, 1H). |

Reference Example 5

4-(4-Fluorophenyl)piperidine hydrochloride (Reference Compound 5-1)

In a solution of 4-(4-fluorophenyl)-1,2,3,6-tetrahydropyridine hydrochloride (1.07 g, 5.0 mmol) in methanol (20 mL), 10% palladium on carbon (0.10 g) was added, and stirred overnight in a hydrogen atmosphere at room temperature. The mixture was filtered by using Celite, and washed with methanol (20 mL). The filtrate was concentrated under reduced pressure, to obtain title Reference Compound 5-1 (1.02 g, yield: 94%) as a yellow white solid.

TABLE 8

| | ¹H-NMR (400 MHz, DMSO-d₆) δ 1.71-1.97 (m, 4H), 2.80-2.91 (m, 1H), 2.91-3.03 (m, 2H), 3.33-3.40 (m, 2H), 7.13-7.20 (m, 2H), 7.22-7.30 (m, 2H), 8.75 (s, 2H). |
|---|---|

Reference Example 6

4-Isopropoxyiodobenzene (Reference Compound 6-1)

In a suspension of 4-iodophenol (2.20 g, 10.0 mmol) and potassium carbonate (2.77 g, 20.0 mmol) in anhydrous N,N-dimethylformamide (40 mL), isopropyl iodide (1.10 mL, 11.0 mmol) was added. The reaction solution was stirred overnight at 80° C. After allowing the reaction solution to cool to room temperature, the reaction solution was diluted with water (200 mL), and extracted with diethylether (200 mL). The organic layer was washed with brine (100 mL) and dried over anhydrous magnesium sulfate. By concentration under reduced pressure, title Reference Compound 6-1 (2.45 g, yield: 94%) was obtained as a brown oily substance.

TABLE 9

| | ¹H-NMR (400 MHz, DMSO-d₆) δ 1.24 (d, J = 6.1 Hz, 6H), 4.55-4.61 (m, 1H), 6.76 (d, J = 9.0 Hz, 2H), 7.56 (d, J = 9.0 Hz, 2H). |
|---|---|

In the following, by using 2-bromo-5-fluorophenol and N-(2-chloroethyl)dimethylamine hydrochloride, Reference Compound 6-2 was obtained according to the production method for Reference Compound 6-1.

TABLE 10

| [2-(2-Bromo-5-fluorophenoxy)ethyl]dimethylamine (Reference Compound 6-2) | ¹H-NMR (500 MHz, DMSO-d₆) δ 2.24 (s, 6H), 2.66 (t, J = 5.5 Hz, 2H), 4.14 (t, J = 5.5 Hz, 2H), 6.74-6.80 (m, 1H), 7.10 (dd, J = 12.0, 3.1 Hz, 1H), 7.59 (dd, J = 8.9, 6.4 Hz, 1H). |
|---|---|

Reference Example 7

4-(4-Fluoro-2-methoxyphenyl)piperazine-1-carboxylic acid tert-butyl ester (Reference Compound 7-1)

In an argon atmosphere, in a suspension of 1-Boc-piperazine (2.98 g, 16.0 mmol), palladium acetate (115 mg, 0.0512 mmol), rac-BINAP (391 mg, 0.628 mmol) and sodium tert-butoxide (2.10 g, 21.9 mmol) in anhydrous toluene (50 mL), 2-bromo-5-fluoroanisole (1.88 mL, 14.6 mmol) was added, and the reaction solution was refluxed overnight. After allowing the reaction solution to cool, saturated ammonium chloride aqueous solution (20 mL) was added, and the reaction solution was extracted with ethyl acetate (100 mL). The organic layer was washed with brine (100 mL), and dried over anhydrous magnesium sulfate, and then concentrated under reduced pressure. The obtained residue was purified by silica gel column chromatography (hexane/ethyl acetate), to obtain title Reference Compound 7-1 (2.63 g, yield: 58%) as a brown oily substance.

TABLE 11

| | ¹H-NMR (400 MHz, DMSO-d₆) δ 1.41 (s, 9H), 2.80-2.86 (m, 4H), 3.39-3.46 (m, 4H), 3.79 (s, 3H), 6.65-6.70 (m, 1H), 6.84-6.90 (m, 2H). |
|---|---|

In the following, by using 1-Boc-piperazine and Reference Compounds 6-1, 6-2 or commercially available compounds, Reference Compounds 7-2 to 7-4 were obtained according to the production method for Reference Compound 7-1.

TABLE 12

| 4-(4-Isopropoxyphenyl)piperazine-1-carboxylic acid tert-butyl ester (Reference Compound 7-2) | ¹H-NMIR (400 MHz, DMSO-d₆) δ 1.21 (d, J = 6.1 Hz, 6H), 1.41 (s, 9H), 2.94 (t, J = 5.0 Hz, 4H), 3.44 (t, J = 5.0 Hz, 4H), 4.40-4.51 (m, 1H), 6.80 (d, J = 9.0 Hz, 2H), 6.88 (d, J = 9.0 Hz, 2H). |
|---|---|

| | |
|---|---|
| 4-Benzo[1,3]dioxol-5-yl-piperazine-1-carboxylic acid tert-butyl ester (Reference Compound 7-3) 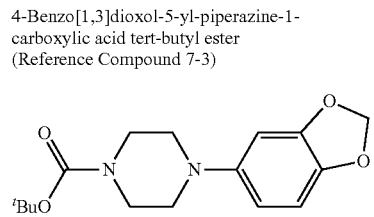 | $^1$H-NMR (400 MHz, DMSO-$d_6$) δ 1.41 (s, 9H), 2.90-2.98 (m, 4H), 3.40-3.45 (m, 4H), 5.92 (s, 2H), 6.36 (dd, J = 8.3, 2.2 Hz, 1H), 6.69 (d, J = 2.2 Hz, 1H), 6.77 (d, J = 8.3 Hz, 1H). |
| 4-[2-(2-Dimethylaminoethoxy)-4-fluorophenyl]piperazine-1-carboxylic acid tert-butyl ester (Reference Compound 7-4) 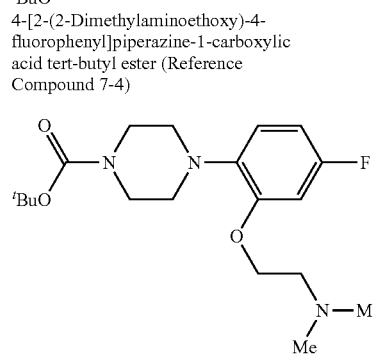 | $^1$H-NMR (400 MHz, DMSO-$d_6$) δ 1.41 (s, 9H), 2.23 (s, 6H), 2.64 (t, J = 5.6 Hz, 2H), 2.85-2.90 (m, 4H), 3.35-3.45 (m, 4H), 4.04 (t, J = 5.6 Hz, 2H), 6.63-6.70 (m, 1H), 6.84-6.90 (m, 2H). |

Reference Example 8

1-(4-Fluoro-2-methoxyphenyl)piperazine dihydrochloride (Reference Compound 8-1)

A solution of 4M hydrogen chloride in 1,4-dioxane (20 mL) was added to a solution of 4-(4-fluoro-2-methoxyphenyl)piperazine-1-carboxylic acid tert-butyl ester (Reference Compound 7-1, 2.59 g, 8.34 mmol) in methanol (5 mL), and stirred at room temperature for 3 days. The precipitated solid was collected by filtration, and dried under reduced pressure, to obtain title Reference Compound 8-1 (1.55 g, yield: 66%) as a colorless powder.

TABLE 13

| | |
|---|---|
| 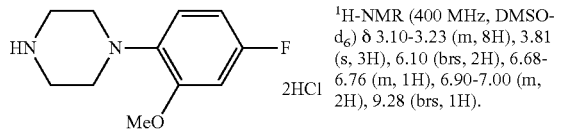 | $^1$H-NMR (400 MHz, DMSO-$d_6$) δ 3.10-3.23 (m, 8H), 3.81 (s, 3H), 6.10 (brs, 2H), 6.68-6.76 (m, 1H), 6.90-7.00 (m, 2H), 9.28 (brs, 1H). |

In the following, by using Reference Compounds 7-2 to 7-5, Reference Compounds 8-2 to 8-4 were obtained according to the production method for Reference Compound 8-1.

TABLE 14

| | |
|---|---|
| 1-(4-Isopropoxyphenyl)piperazine hydrochloride (Reference Compound 8-2) 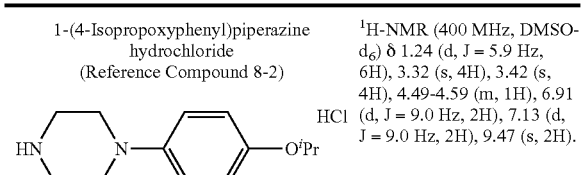 | $^1$H-NMR (400 MHz, DMSO-$d_6$) δ 1.24 (d, J = 5.9 Hz, 6H), 3.32 (s, 4H), 3.42 (s, 4H), 4.49-4.59 (m, 1H), 6.91 (d, J = 9.0 Hz, 2H), 7.13 (d, J = 9.0 Hz, 2H), 9.47 (s, 2H). |

TABLE 14-continued

| | |
|---|---|
| 1-Benzo[1,3]dioxol-5-yl-piperazine dihydrochloride (Reference Compound 8-3) 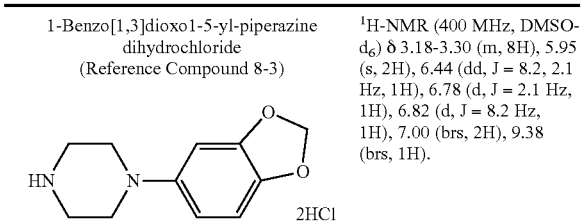 | $^1$H-NMR (400 MHz, DMSO-$d_6$) δ 3.18-3.30 (m, 8H), 5.95 (s, 2H), 6.44 (dd, J = 8.2, 2.1 Hz, 1H), 6.78 (d, J = 2.1 Hz, 1H), 6.82 (d, J = 8.2 Hz, 1H), 7.00 (brs, 2H), 9.38 (brs, 1H). |
| 1-[2-(2-Dimethylaminoethoxy)-4-fluorophenyl]piperazine trihydrochloride (Reference Compound 8-4) 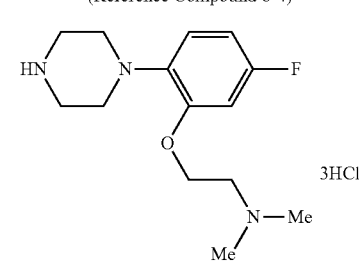 | $^1$H-NMR (400 MHz, DMSO-$d_6$) δ 2.86 (d, J = 4.9 Hz, 6H), 3.10-3.30 (m, 8H), 3.53-3.60 (m, 2H), 4.38-4.60 (m, 2H), 6.00 (brs, 1H), 6.77-6.83 (m, 1H), 6.99-7.08 (m, 1H), 9.47 (brs, 2H), 11.10 (brs, 1H). |

Reference Example 9

1-(4-Fluorophenyl)-3-methylpiperazine (Reference Compound 9-1)

In an argon atmosphere, 1-Bromo-4-fluorobenzene (3.14 mL, 28.5 mmol) was added to a solution of 2-methylpiperazine (3.15 g, 31.3 mmol), palladium acetate (220 mg, 0.980 mmol), rac-BINAP (750 mg, 1.20 mmol) and sodium tert-butoxide (4.00 g, 42.0 mmol) in anhydrous toluene (90 mL). The reaction solution was refluxed overnight, and allowed to cool, and then water (30 mL) was added. The toluene layer was washed with brine (30 mL), and dried over anhydrous magnesium sulfate, and then concentrated under reduced pressure. The obtained residue was purified by silica gel column chromatography (hexane/ethyl acetate), to obtain title Reference Compound 9-1 (4.24 g, yield: 77%) as a brown oily substance.

TABLE 15

| Structure | ¹H-NMR |
|---|---|
| Me-substituted piperazine with 4-fluorophenyl group (HN-piperazine(Me)-C₆H₄-F) | ¹H-NMR (400 MHz, DMSO-d₆) δ 1.00 (d, J = 6.1 Hz, 3H), 2.12 (t, J = 10.7 Hz, 1H), 2.20 (brs, 1H), 2.44-2.55 (m, 1H), 2.70- 2.80 (m, 2H), 2.90-2.95 (m, 1H), 3.35-3.43 (m, 2H), 6.85-6.94 (m, 2H), 6.98-7.05 (m, 2H). |

Example 1

2-[4-(4-Fluorophenyl)piperazine-1-carbonyl]pyrrolo[1,2-a]quinazolin-5(4H)-one (Compound 1-1)

Diisopropylethylamine (11.4 mL, 65.5 mmol) and HCTU (8.11 g, 19.6 mmol) were added to a solution of 5-oxo-4,5-dihydropyrrolo[1,2-a]quinazoline-2-carboxylic acid (Reference Compound 4-1, 3.00 g, 13.1 mmol) and 4-fluorophenylpiperazine dihydrochloride (3.98 g, 15.7 mmol) in N,N-dimethylformamide (50 mL), and the reaction solution was stirred overnight at room temperature. Water (100 mL) and ethyl acetate (100 mL) were added to this reaction solution, and the reaction solution was stirred for 10 minutes. The precipitated solid in the organic layer was collected by filtration, and dried at 50° C. under reduced pressure, to obtain title Compound 1-1 (2.80 g) as a pale brown powder. The aqueous layer was extracted with ethyl acetate (100 mL), washed with brine (100 mL), dried over anhydrous magnesium sulfate, concentrated under reduced pressure, and the precipitated solid was collected by filtration, and dried at 50° C. under reduced pressure to obtain title Compound 1-1 (0.48 g) as a pale brown powder (total amount: 3.28 g, yield: 63%).

TABLE 16

| Structure | ¹H-NMR |
|---|---|
| Compound 1-1 structure | ¹H-NMR (400 MHz, DMSO-d₆) δ 3.15-3.25 (m, 4H), 3.70-3.90 (m, 4H), 5.76 (d, J = 1.7 Hz, 1H), 6.96-7.03 (m, 2H), 7.04-7.12 (m, 2H), 7.40-7.48 (m, 1H), 7.79-7.88 (m, 1H), 7.96 (d, J = 1.7 Hz, 1H), 8.10-8.15 (m, 2H), 11.81 (s, 1H). |

In the following, by using Reference Compounds 4-1 to 4-3, 5-1, 8-1 to 8-5, 9-1 and commercially available compounds, Compounds 1-2 to 1-58 were obtained according to the production method for Compound 1-1.

TABLE 17

| Compound | ¹H-NMR |
|---|---|
| 2-[4-(4-Chlorobenzyl)piperazine-1-carbonyl]pyrrolo[1,2-a]quinazolin-5(4H)-one (Compound 1-2) | ¹H-NMR (400 MHz, DMSO-d₆) δ 2.30-2.50 (m, 4H), 3.51 (s, 2H), 3.55-3.70 (m, 4H), 5.71 (d, J = 1.8 Hz, 1H), 7.30-7.50 (m, 5H), 7.81 (t, J = 7.0 Hz, 1H), 7.90 (d, J = 1.8 Hz, 1H), 8.10-8.13 (m, 2H), 11.78 (s, 1H). |
| 2-[4-(Thiazol-2-yl)piperazine-1-carbonyl]pyrrolo[1,2-a]quinazolin-5(4H)-one (Compound 1-3) | ¹H-NMR (400 MHz, DMSO-d₆) δ 3.48-3.51 (m, 4H), 3.79-3.81 (m, 4H), 5.77 (d, J = 1.8 Hz, 1H), 6.91 (d, J = 3.7 Hz, 1H), 7.22 (d, J = 3.7 Hz, 1H), 7.45 (t, J = 8.0 Hz, 1H), 7.82 (td, J = 8.0, 1.6 Hz, 1H), 7.96 (d, J = 1.8 Hz, 1H), 8.13 (dd, J = 8.0, 1.6 Hz, 1H), 8.13 (d, J = 8.0 Hz, 1H), 11.81 (s, 1H). |

TABLE 17-continued

| | |
|---|---|
| 2-(4-Phenylpiperazine-1-carbonyl)pyrrolo[1,2-a]quinazolin-5(4H)-one (Compound 1-4)<br>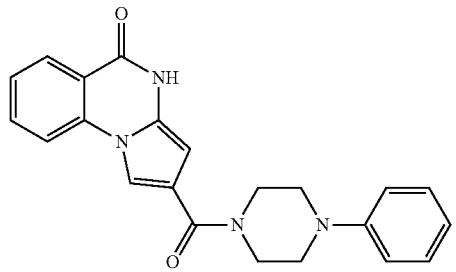 [SMILES: O=C(c1cc2[nH]c(=O)c3ccccc3n2c1)N1CCN(c2ccccc2)CC1] | ¹H-NMR (500 MHz, DMSO-d₆) δ 3.19 (t, J= 5.0 Hz, 4H), 3.78-3.85 (m, 4H), 5.77 (d, J = 1.8 Hz, 1H), 6.82 (tt, J = 7.5, 1.3 Hz, 1H), 6.97 (dt, J = 7.5, 1.3 Hz, 2H), 7.24 (td, J = 7.5, 1.3 Hz, 2H), 7.45 (ddd, J = 8.4, 7.5, 1.4 Hz, 1H), 7.82 (ddd, J = 8.4, 7.5, 1.4 Hz, 1H), 7.97 (d, J = 1.8 Hz, 1H), 8.12-8.14 (m, 2H), 11.82 (s, 1H). |

TABLE 18

| | |
|---|---|
| 2-(4-Phenylpiperidine-1-carbonyl)pyrrolo[1,2-a]quinazolin-5(4H)-one (Compound 1-5)<br>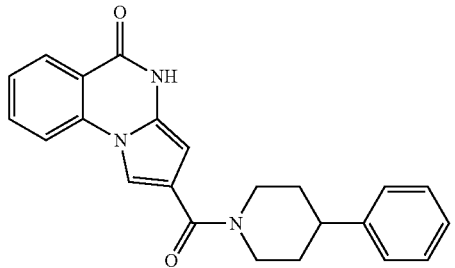 | ¹H-NMR (400 MHz, DMSO-d₆) δ 1.49-1.71 (m, 2H), 1.75-1.96 (m, 2H), 2.77-3.11 (m, 3H), 4.29-4.67 (m, 2H), 5.75 (d, J = 1.7 Hz, 1H), 7.13-7.37 (m, 5H), 7.44 (t, J = 8.0 Hz, 1H), 7.77-7.86 (m, 1H), 7.92 (d, J = 1.7 Hz, 1H), 8.10-8.16 (m, 2H), 11.78 (s, 1H). |
| 2-(4-Phenyl-1,2,3,6-tetrahydropyridine-1-carbonyl)pyrrolo[1,2-a]quinazolin-5(4H)-one (Compound 1-6)<br>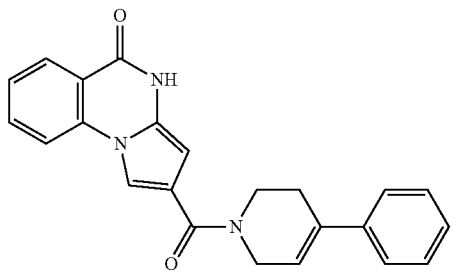 [SMILES: O=C(c1cc2[nH]c(=O)c3ccccc3n2c1)N1CC=C(c2ccccc2)CC1] | ¹H-NMR (400 MHz, DMSO-d₆) δ 2.60 (s, 2H), 3.86 (t, J = 5.4 Hz, 2H), 4.34 (s, 2H), 5.80 (d, J = 1.6 Hz, 1H), 6.21 (s, 1H), 7.27 (t, J = 7.3 Hz, 1H), 7.36 (t, J = 7.3 Hz, 2H), 7.43-7.45 (m, 1H), 7.47 (d, J = 7.3 Hz, 2H), 7.82 (dd, J = 8.0, 1.7 Hz, 1H), 7.99 (d, J = 1.6 Hz, 1H), 8.13 (dd, J = 8.0, 1.7 Hz, 1H), 8.15 (d, J = 8.0 Hz, 1H), 11.82 (s, 1H). |
| 2-[4-(4-Chlorophenyl)-1,2,3,6-tetrahydropyridine-1-carbonyl]pyrrolo[1,2-a]quinazolin-5(4H)-one (Compound 1-7)<br>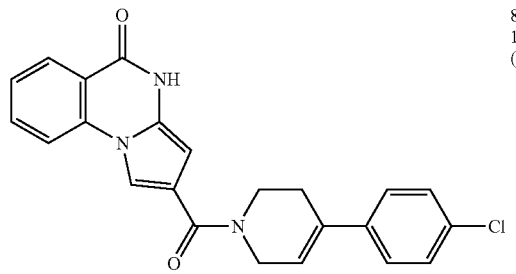 | ¹H-NMR (400 MHz, DMSO-d₆) δ 2.58 (s, 2H), 3.85 (t, J = 5.4 Hz, 2H), 4.34 (s, 2H), 5.80 (d, J = 1.6 Hz, 1H), 6.25 (s, 1H), 7.40-7.50 (m, 5H), 7.82 (ddd, J = 8.1, 7.3, 1.4 Hz, 1H), 7.98 (d, J = 1.6 Hz, 1H), 8.13 (dd, J = 8.1, 1.4 Hz, 1H), 8.14 (d, J = 8.1 Hz, 1H), 11.81 (s, 1H). |

TABLE 19

| 2-[4-(4-Fluorophenyl)-1,2,3,6-tetrahydropyridine-1-carbonyl]pyrrolo[1,2-a]quinazolin-5(4H)-one (Compound 1-8) 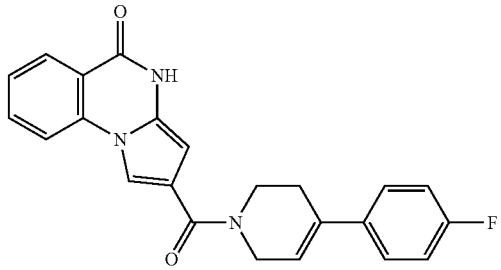 [SMILES: O=C(c1cc2[nH]c(=O)c3ccccc3n2c1)N1CC=C(c2ccc(F)cc2)CC1] | $^1$H-NMR (400 MHz, DMSO-$d_6$) δ 2.58 (s, 2H), 3.85 (t, J = 5.4 Hz, 2H), 4.33 (s, 2H), 5.80 (d, J = 1.6 Hz, 1H), 6.18 (s, 1H), 7.19 (t, J = 8.9 Hz, 2H), 7.43-7.47 (m, 1H), 7.49-7.52 (m, 2H), 7.82 (ddd, J = 8.0, 7.8, 1.5 Hz, 1H), 7.98 (d, J = 1.6 Hz, 1H), 8.13 (dd, J = 7.8, 1.5 Hz, 1H), 8.14 (d, J = 8.0 Hz, 1H), 11.80 (s, 1H). |
|---|---|
| 2-[4-(2-Fluorophenyl)piperazine-1-carbonyl]pyrrolo[1,2-a]quinazolin-5(4H)-one (Compound 1-9) 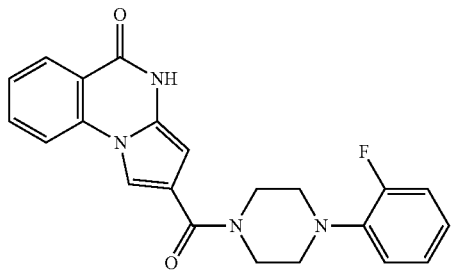 [SMILES: O=C(c1cc2[nH]c(=O)c3ccccc3n2c1)N1CCN(c2ccccc2F)CC1] | $^1$H-NMR (400 MHz, DMSO-$d_6$) δ 3.03-3.07 (m, 4H), 3.79-3.86 (m, 4H), 5.77 (d, J = 1.8 Hz, 1H), 6.98-7.20 (m, 4H), 7.45 (t, J = 7.9 Hz, 1H), 7.82 (td, J = 7.9, 1.6 Hz, 1H), 7.96 (d, J = 1.8 Hz, 1H), 8.11-8.15 (m, 2H), 11.81 (s, 1H). |
| 2-(4-Methylpiperazine-1-carbonyl)pyrrolo[1,2-a]quinazolin-5(4H)-one (Compound 1-10) 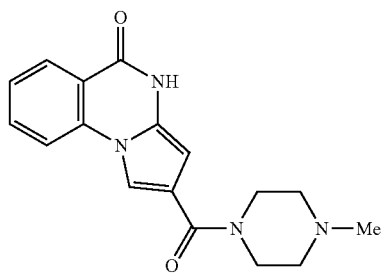 [SMILES: CN1CCN(C(=O)c2cc3[nH]c(=O)c4ccccc4n3c2)CC1] | $^1$H-NMR (400 MHz, DMSO-$d_6$) δ 2.51-2.55 (m, 4H), 2.73 (s, 3H), 3.00-3.15 (m, 4H), 5.77 (d, J = 1.8 Hz, 1H), 7.46 (t, J = 7.9 Hz, 1H), 7.84 (td, J = 7.9, 1.4 Hz, 1H), 7.97 (d, J = 1.8 Hz, 1H), 8.13 (d, J = 7.9 Hz, 1H), 8.14 (dd, J = 7.9, 1.4 Hz, 1H), 11.85 (s, 1H). |

TABLE 20

| 2-(4-Benzylpiperazine-1-carbonyl)pyrrolo[1,2-a]quinazolin-5(4H)-one (Compound 1-11) 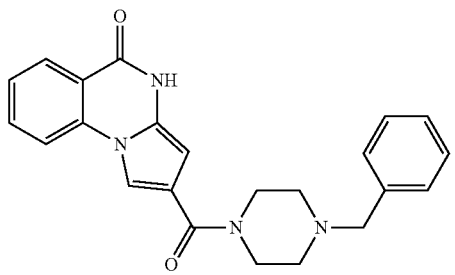 [SMILES: O=C(c1cc2[nH]c(=O)c3ccccc3n2c1)N1CCN(Cc2ccccc2)CC1] | $^1$H-NMR (400 MHz, DMSO-$d_6$) δ 2.30-2.50 (m, 4H), 3.52 (s, 2H), 3.60-3.70 (m, 4H), 5.71 (d, J = 2.0 Hz, 1H), 7.24-7.40 (m, 5H), 7.43 (ddd, J = 8.0, 7.0, 1.0 Hz, 1H), 7.80 (ddd, J = 8.0, 7.0, 1.5 Hz, 1H), 7.89 (d, J = 2.0 Hz, 1H), 8.05-8.14 (m, 2H), 11.77 (s, 1H). |
|---|---|

TABLE 20-continued

| | |
|---|---|
| 2-[4-(4-Chlorophenyl)piperazine-1-carbonyl]pyrrolo[1,2-a]quinazolin-5(4H)-one (Compound 1-12) 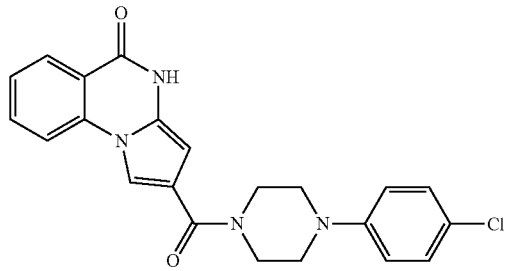 [SMILES: O=C(c1cc2[nH]c(=O)c3ccccc3n2c1)N1CCN(c2ccc(Cl)cc2)CC1] | $^1$H-NMR (400 MHz, DMSO-d$_6$) δ 3.20 (t, J = 5.0 Hz, 4H), 3.79 (t, J = 5.0 Hz, 4H), 5.76 (d, J = 2.0 Hz, 1H), 6.98 (d, J = 9.0 Hz, 2H), 7.26 (d, J = 9.0 Hz, 2H), 7.45 (ddd, J = 8.2, 7.5, 1.3 Hz, 1H), 7.82 (ddd, J = 8.2, 7.5, 1.3 Hz, 1H), 7.96 (d, J = 2.0 Hz, 1H), 8.11-8.14 (m, 2H), 11.81 (s, 1H). |
| 2-[4-(4-Fluorobenzyl)piperazine-1-carbonyl]pyrrolo[1,2-a]quinazolin-5(4H)-one (Compound 1-13) 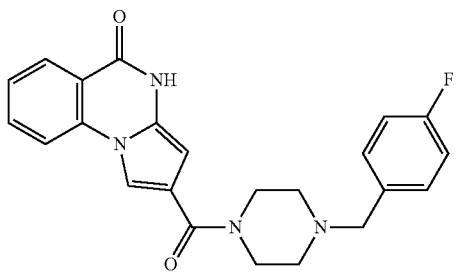 [SMILES: O=C(c1cc2[nH]c(=O)c3ccccc3n2c1)N1CCN(Cc2ccc(F)cc2)CC1] | $^1$H-NMR (400 MHz, DMSO-d$_6$) δ 2.39 (t, J = 4.9 Hz, 4H), 3.50 (s, 2H), 3.65 (s, 4H), 5.71 (d, J = 1.8 Hz, 1H), 7.13-7.18 (m, 2H), 7.34-7.38 (m, 2H), 7.43 (t, J = 7.3 Hz, 1H), 7.81 (ddd, J = 8.0, 7.3, 1.6 Hz, 1H), 7.89 (d, J = 1.8 Hz, 1H), 8.11 (d, J = 8.0 Hz, 1H), 8.12 (dd, J = 8.0, 1.6 Hz, 1H), 11.78 (s, 1H). |

TABLE 21

| | |
|---|---|
| 2-[4-(4-Fluorophenyl)piperidine-1-carbonyl]pyrrolo[1,2-a]quinazolin-5(4H)-one (Compound 1-14) 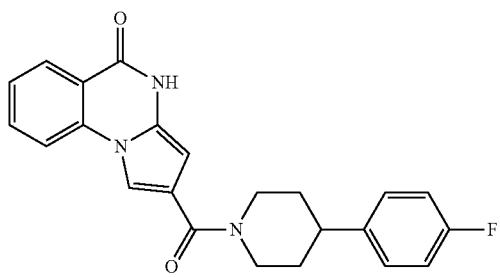 [SMILES: O=C(c1cc2[nH]c(=O)c3ccccc3n2c1)N1CCC(c2ccc(F)cc2)CC1] | $^1$H-NMR (400 MHz, DMSO-d$_6$) δ 1.48-1.69 (m, 2H), 1.75-1.90 (m, 2H), 2.80-3.16 (m, 3H), 4.48 (s, 2H), 5.75 (d, J = 1.8 Hz, 1H), 7.09-7.17 (m, 2H), 7.29-7.36 (m, 2H), 7.44 (t, J = 7.6 Hz, 1H), 7.76-7.86 (m, 1H), 7.92 (d, J = 1.8 Hz, 1H), 8.13-8.14 (m, 2H), 11.78 (s, 1H). |
| 2-[4-(3-Fluorophenyl)piperazine-1-carbonyl]pyrrolo[1,2-a]quinazolin-5(4H)-one (Compound 1-15) 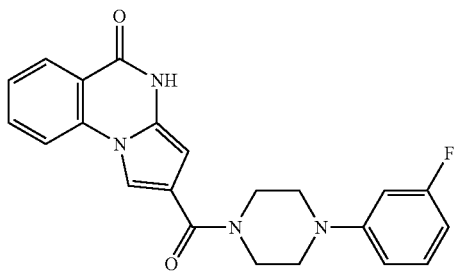 [SMILES: O=C(c1cc2[nH]c(=O)c3ccccc3n2c1)N1CCN(c2cccc(F)c2)CC1] | $^1$H-NMR (400 MHz, DMSO-d$_6$) δ 3.22-3.28 (m, 4H), 3.77-3.82 (m, 4H), 5.77 (d, J = 1.8 Hz, 1H), 6.58 (td, J = 8.2, 2.2 Hz, 1H), 6.75-6.81 (m, 2H), 7.24 (q, J = 8.2 Hz, 1H), 7.45 (t, J = 7.9 Hz, 1H), 7.82 (td, J = 7.9, 1.1 Hz, 1H), 7.96 (d, J = 1.8 Hz, 1H), 8.13 (dd, J = 7.9, 1.1 Hz, 2H), 11.81 (s, 1H). |

TABLE 21-continued

| Compound | ¹H-NMR |
|---|---|
| 2-[4-(4-Methoxyphenyl)piperazine-1-carbonyl]pyrrolo[1,2-a]quinazolin-5(4H)-one (Compound 1-16) | ¹H-NMR (400 MHz, DMSO-$d_6$) δ 3.03-3.07 (m, 4H), 3.69 (s, 3H), 3.76-3.82 (m, 4H), 5.75 (d, J = 2.0 Hz, 1H), 6.84 (d, J = 9.3 Hz, 2H), 6.94 (d, J = 9.3 Hz, 2H), 7.44 (t, J = 7.8 Hz, 1H), 7.82 (td, J = 7.8, 1.4 Hz, 1H), 7.95 (d, J = 2.0 Hz, 1H), 8.11-8.14 (m, 2H), 11.81 (s, 1H). |

TABLE 22

| Compound | ¹H-NMR |
|---|---|
| 2-[4-(Pyridin-2-yl)piperazine-1-carbonyl]pyrrolo[1,2-a]quinazolin-5(4H)-one (Compound 1-17) | ¹H-NMR (400 MHz, DMSO-$d_6$) δ 3.55-3.59 (m, 4H), 3.74-3.79 (m, 4H), 5.77 (d, J = 1.8 Hz, 1H), 6.67 (dd, J = 7.0, 5.0 Hz, 1H), 6.86 (d, J = 8.5 Hz, 1H), 7.45 (t, J = 7.7 Hz, 1H), 7.54-7.59 (m, 1H), 7.82 (td, J = 7.7, 1.4 Hz, 1H), 7.96 (d, J = 1.8 Hz, 1H), 8.12-8.15 (m, 3H), 11.81 (s, 1H). |
| 2-[4-(Pyridin-3-yl)piperazine-1-carbonyl]pyrrolo[1,2-a]quinazolin-5(4H)-one (Compound 1-18) | ¹H-NMR (400 MHz, DMSO-$d_6$) δ 3.25-3.29 (m, 4H), 3.79-3.84 (m, 4H), 5.77 (d, J = 1.7 Hz, 1H), 7.24 (dd, J = 8.5, 4.5 Hz, 1H), 7.36 (ddd, J = 8.5, 2.9, 1.2 Hz, 1H), 7.45 (t, J = 7.9 Hz, 1H), 7.82 (td, J = 7.9, 1.3 Hz, 1H), 7.97 (d, J = 1.7 Hz, 1H), 8.03 (dd, J = 4.5, 1.2 Hz, 1H), 8.12-8.15 (m, 2H), 8.34 (d, J = 2.9 Hz, 1H), 11.82 (s, 1H). |
| 2-[N-Methyl-N-(3-phenylpropyl)aminocarbonyl]pyrrolo[1,2-a]quinazolin-5(4H)-one (Compound 1-19) | ¹H-NMR (400 MHz, DMSO-$d_6$) δ 1.86-1.90 (m, 2H), 2.58 (t, J = 7.3 Hz, 2H), 3.33 (s, 3H), 3.48 (t, J = 7.3 Hz, 2H), 5.76 (s, 1H), 7.20-7.24 (m, 5H), 7.30-7.34 (m, 1H), 7.44 (t, J = 7.4 Hz, 1H), 7.82 (ddd, J = 7.9, 7.4, 1.5 Hz, 1H), 8.09 (s, 1H), 8.13 (dd, J = 7.9, 1.5 Hz, 1H), 11.77 (s, 1H). |

TABLE 23

| | |
|---|---|
| 2-[4-(4-Bromophenyl)piperazine-1-carbonyl]pyrrolo[1,2-a]quinazolin-5(4H)-one (Compound 1-20) 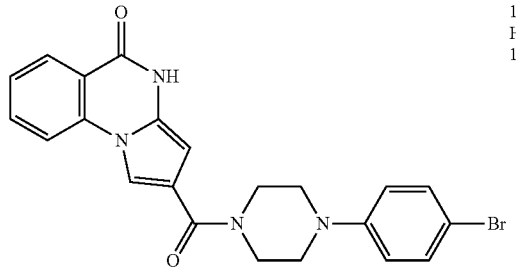 | $^1$H-NMR (500 MHz, DMSO-$d_6$) δ 3.15-3.25 (m, 4H), 3.75-3.85 (m, 4H), 5.76 (d, J = 1.8 Hz, 1H), 6.93 (d, J = 9.2 Hz, 2H), 7.38 (d, J = 9.2 Hz, 2H), 7.40-7.47 (m, 1H), 7.79-7.85 (m, 1H), 7.96 (d, J = 1.8 Hz, 1H), 8.10-8.15 (m, 2H), 11.82 (s, 1H). |
| 2-(3,4-Dihydroisoquinoline-2(1H)-carbonyl)pyrrolo[1,2-a]quinazolin-5(4H)-one (Compound 1-21) 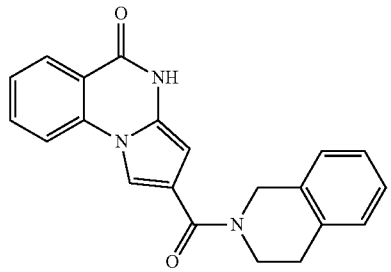 [SMILES: O=C(c1cc2[nH]c(=O)c3ccccc3n2c1)N1CCc2ccccc2C1] | $^1$H-NMR (400 MHz, DMSO-$d_6$) δ 2.87-2.93 (m, 2H), 3.83-3.90 (m, 2H), 4.76-4.86 (m, 2H), 5.80 (d, J = 1.5 Hz, 1H), 7.18-7.22 (m, 4H), 7.44 (t, J = 7.7 Hz, 1H), 7.82 (td, J = 7.7, 1.3 Hz, 1H), 7.99 (d, J = 1.5 Hz, 1H), 8.12-8.15 (m, 2H), 11.81 (s, 1H). |
| 2-(4-Dimethylaminopiperidine-1-carbonyl)pyrrolo[1,2-a]quinazolin-5(4H)-one (Compound 1-22) 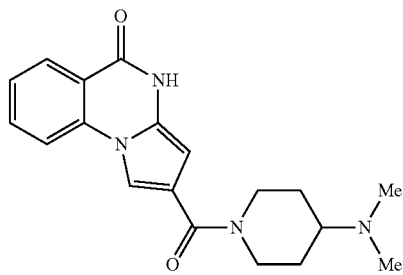 [SMILES: CN(C)C1CCN(C(=O)c2cc3[nH]c(=O)c4ccccc4n3c2)CC1] | $^1$H-NMR (400 MHz, CD$_3$OD) δ 1.65-1.76 (m, 2H), 2.12-2.19 (m, 2H), 2.86-2.91 (m, 1H), 2.90 (s, 6H), 3.47-3.56 (m, 2H), 4.65-4.74 (m, 2H), 5.90 (d, J = 1.7 Hz, 1H), 7.47 (t, J = 8.0 Hz, 1H), 7.80 (d, J = 1.7 Hz, 1H), 7.82 (td, J = 8.0, 1.2 Hz, 1H), 7.95 (d, J = 8.0 Hz, 1H), 8.24 (dd, J = 8.0, 1.2 Hz, 1H). |

TABLE 24

| | |
|---|---|
| 2-[4-(Pyridin-4-yl)piperazine-1-carbonyl]pyrrolo[1,2-a]quinazolin-5(4H)-one (Compound 1-23) 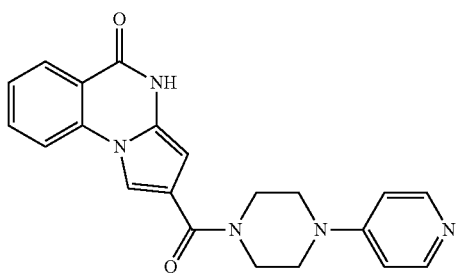 [SMILES: O=C(c1cc2[nH]c(=O)c3ccccc3n2c1)N1CCN(c2ccncc2)CC1] | $^1$H-NMR (400 MHz, DMSO-$d_6$) δ 3.41-3.45 (m, 4H), 3.76-3.82 (m, 4H), 5.78 (d, J = 2.0 Hz, 1H), 6.84 (dd, J = 5.1, 1.5 Hz, 2H), 7.45 (t, J = 7.9 Hz, 1H), 7.82 (td, J = 7.9, 1.5 Hz, 1H), 7.97 (d, J = 2.0 Hz, 1H), 8.11-8.15 (m, 2H), 8.19 (dd, J = 5.1, 1.5 Hz, 2H), 11.82 (s, 1H). |

TABLE 24-continued

| | |
|---|---|
| 2-[4-(4-Fluorophenyl)-2-methylpiperazine-1-carbonyl]pyrrolo[1,2-a]quinazolin-5(4H)-one (Compound 1-24) 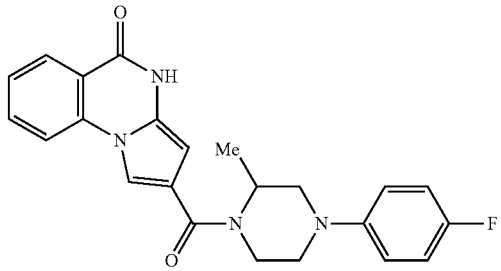 [SMILES: CC1CN(c2ccc(F)cc2)CCN1C(=O)c1cc2[nH]c(=O)c3ccccc3n2c1] | $^1$H-NMR (400 MHz, DMSO-d$_6$) δ 1.35 (d, J = 6.6 Hz, 3H), 2.60-2.70 (m, 1H), 2.78-2.84 (m, 1H), 3.30-3.50 (m, 2H), 3.56 (d, J = 12.0 Hz, 1H), 4.26 (d, J = 12.0 Hz, 1H), 4.67 (s, 1H), 5.74 (d, J = 1.7 Hz, 1H), 6.94-7.00 (m, 2H), 7.03-7.11 (m, 2H), 7.44 (t, J = 8.0 Hz, 1H), 7.82 (t, J = 8.0 Hz, 1H), 7.93 (d, J = 1.7 Hz, 1H), 8.10-8.15 (m, 2H), 11.80 (s, 1H). |
| 2-[4-(2-Methoxyphenyl)piperazine-1-carbonyl]pyrrolo[1,2-a]quinazolin-5(4H)-one (Compound 1-25) 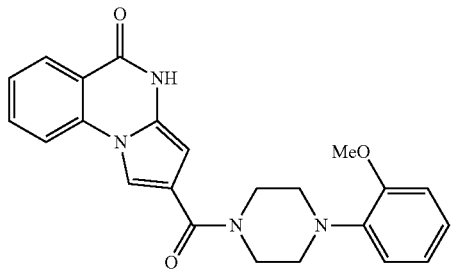 [SMILES: COc1ccccc1N1CCN(C(=O)c2cc3[nH]c(=O)c4ccccc4n3c2)CC1] | $^1$H-NMR (400 MHz, DMSO-d$_6$) δ 2.97-3.00 (m, 4H), 3.78-3.83 (m, 4H), 3.80 (s, 3H), 5.76 (d, J = 1.8 Hz, 1H), 6.87-7.01 (m, 4H), 7.44 (t, J = 7.9 Hz, 1H), 7.82 (td, J = 7.9, 1.5 Hz, 1H), 7.95 (d, J = 1.8 Hz, 1H), 8.13 (dd, J = 7.9, 1.5 Hz, 1H), 8.14 (d, J = 7.9 Hz, 1H), 11.82 (s, 1H). |

TABLE 25

| | |
|---|---|
| 2-[4-(3-Methoxyphenyl)piperazine-1-carbonyl]pyrrolo[1,2-a]quinazolin-5(4H)-one (Compound 1-26) 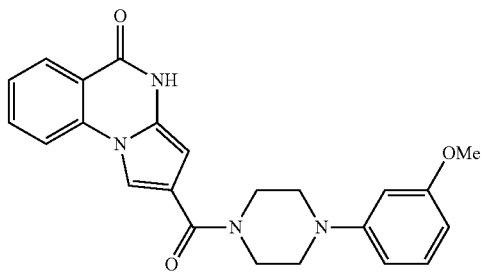 [SMILES: COc1cccc(N2CCN(C(=O)c3cc4[nH]c(=O)c5ccccc5n4c3)CC2)c1] | $^1$H-NMR (400 MHz, DMSO-d$^6$) δ 3.17-3.21 (m, 4H), 3.72 (s, 3H), 3.76-3.81 (m, 4H), 5.76 (d, J = 1.8 Hz, 1H), 6.40 (dd, J = 8.2, 2.2 Hz, 1H), 6.49 (t, J = 2.2 Hz, 1H), 6.56 (dd, J = 8.2, 2.2 Hz, 1H), 7.13 (t, J = 8.2 Hz, 1H), 7.45 (t, J = 7.9 Hz, 1H), 7.82 (td, J = 7.9, 1.5 Hz, 1H), 7.96 (d, J = 1.8 Hz, 1H), 8.13 (dd, J = 7.9, 1.5 Hz, 1H), 8.13 (d, J = 7.9 Hz, 1H), 11.78 (s, 1H). |
| 2-(4-Cyclohexylpiperazine-1-carbonyl)pyrrolo[1,2-a]quinazolin-5(4H)-one (Compound 1-27) 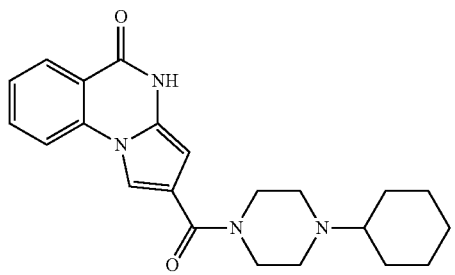 [SMILES: O=C(c1cc2[nH]c(=O)c3ccccc3n2c1)N1CCN(C2CCCCC2)CC1] | $^1$H-NMR (400 MHz, DMSO-d$^6$) δ 1.00-1.30 (m, 5H), 1.50-1.60 (m, 1H), 1.64-1.82 (m, 4H), 2.10-2.35 (m, 1H), 2.40-2.60 (m, 4H), 3.50-3.70 (m, 4H), 5.70 (d, J = 2.0 Hz, 1H), 7.43 (t, J = 8.0 Hz, 1H), 7.77-7.84 (m, 1H), 7.89 (d, J = 2.0 Hz, 1H), 8.10-8.15 (m, 2H), 11.79 (s, 1H). |

TABLE 25-continued

| | |
|---|---|
| 2-[4-Cyclopropylmethylpiperazine-1-carbonyl]pyrrolo[1,2-a]quinazolin-5(4H)-one (Compound 1-28)<br />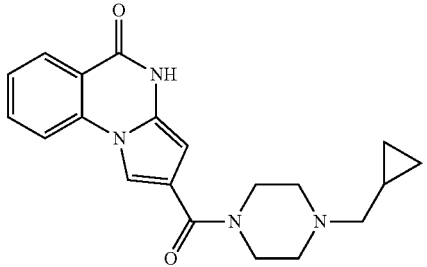 [SMILES: O=C(c1cc2[nH]c(=O)c3ccccc3n2c1)N1CCN(CC2CC2)CC1] | $^1$H-NMR (500 MHz, DMSO-$d_6$) δ 0.03-0.12 (m, 2H), 0.44-0.50 (m, 2H), 0.80-0.90 (m, 1H), 2.21 (d, J = 6.4 Hz, 2H), 2.40-2.50 (m, 4H), 3.50-3.80 (m, 4H), 5.71 (d, J = 1.8 Hz, 1H), 7.40-7.46 (m, 1H), 7.78-7.85 (m, 1H), 7.91 (d, J = 1.8 Hz, 1H), 8.10-8.14 (m, 2H), 11.79 (s, 1H). |

TABLE 26

| | |
|---|---|
| 2-[4-(4-Trifluoromethylphenyl)piperazine-1-carbonyl]pyrrolo[1,2-a]quinazolin-5(4H)-one (Compound 1-29)<br />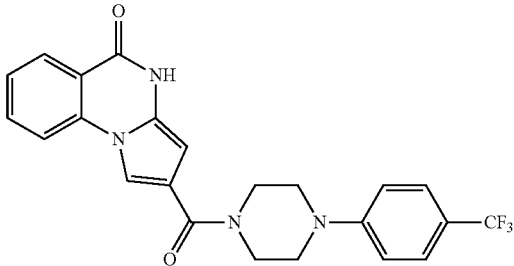 [SMILES: O=C(c1cc2[nH]c(=O)c3ccccc3n2c1)N1CCN(c2ccc(C(F)(F)F)cc2)CC1] | $^1$H-NMR (400 MHz, DMSO-$d_6$) δ 3.36-3.41 (m, 4H), 3.78-3.84 (m, 4H), 5.78 (d, J = 1.8 Hz, 1H), 7.09 (d, J = 8.7 Hz, 2H), 7.45 (t, J = 7.9 Hz, 1H), 7.54 (d, J = 8.7 Hz, 2H), 7.82 (t, J = 7.9 Hz, 1H), 7.98 (d, J = 1.8 Hz, 1H), 8.12-8.14 (m, 2H), 11.83 (s, 1H). |
| 2-[4-(5-Chloropyridin-2-yl)piperazine-1-carbonyl]pyrrolo[1,2-a]quinazolin-5(4H)-one (Compound 1-30)<br />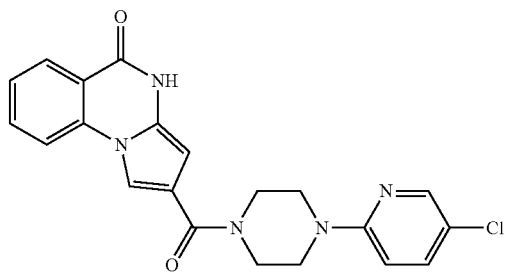 [SMILES: O=C(c1cc2[nH]c(=O)c3ccccc3n2c1)N1CCN(c2ccc(Cl)cn2)CC1] | $^1$H-NMR (400 MHz, DMSO-$d_6$) δ 3.55-3.62 (m, 4H), 3.73-3.80 (m, 4H), 5.77 (d, J = 1.7 Hz, 1H), 6.90 (d, J = 9.1 Hz, 1H), 7.45 (t, J = 7.7 Hz, 1H), 7.64 (dd, J = 9.1, 2.6 Hz, 1H), 7.82 (t, J = 7.7 Hz, 1H), 7.97 (d, J = 1.7 Hz, 1H), 8.12-8.13 (m, 2H), 8.14 (d, J = 2.6 Hz, 1H), 11.82 (s, 1H). |
| 2-(3-Phenylpiperidine-1-carbonyl)pyrrolo[1,2-a]quinazolin-5(4H)-one (Compound 1-31)<br />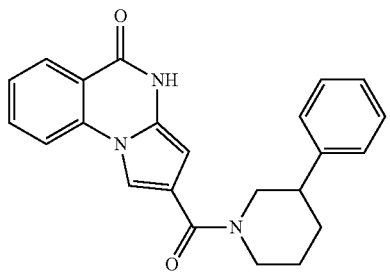 [SMILES: O=C(c1cc2[nH]c(=O)c3ccccc3n2c1)N1CCCC(c2ccccc2)C1] | $^1$H-NMR (400 MHz, DMSO-$d_6$) δ 1.50-1.63 (m, 1H), 1.75-1.85 (m, 2H), 1.92-2.01 (m, 1H), 2.70-2.78 (m, 2H), 2.84-2.89 (m, 1H), 4.28-4.49 (m, 2H), 5.73 (d, J = 1.5 Hz, 1H), 7.21-7.25 (m, 1H), 7.28-7.33 (m, 4H), 7.43 (t, J = 7.6 Hz, 1H), 7.81 (t, J = 7.6 Hz, 1H), 7.93 (d, J = 1.5 Hz, 1H), 8.09-8.13 (m, 2H), 11.77 (s, 1H). |

TABLE 27

| | |
|---|---|
| 2-[4-(3-Methylphenyl)piperazine-1-carbonyl]pyrrolo[1,2-a]quinazolin-5(4H)-one (Compound 1-32)<br />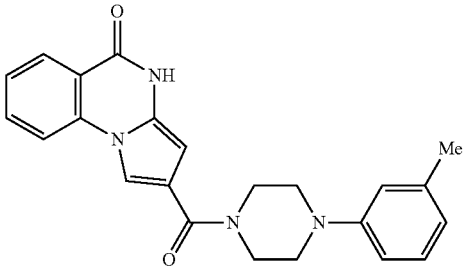 [SMILES: Cc1cccc(N2CCN(C(=O)c3cc4[nH]c(=O)c5ccccc5n4c3)CC2)c1] | $^1$H-NMR (400 MHz, DMSO-d$_6$) δ 2.26 (s, 3H), 3.12-3.21 (m, 4H), 3.74-3.84 (m, 4H), 5.76 (d, J = 2.0 Hz, 1H), 6.64 (d, J = 7.6 Hz, 1H), 6.70-6.85 (m, 2H), 7.12 (t, J = 7.6 Hz, 1H), 7.45 (t, J = 7.6 Hz, 1H), 7.79-7.85 (m, 1H), 7.96 (d, J = 2.0 Hz, 1H), 8.10-8.16 (m, 2H), 11.80 (s, 1H). |
| 2-[4-(Piperidin-1-yl)piperidine-1-carbonyl]pyrrolo[1,2-a]quinazolin-5(4H)-one (Compound 1-33)<br />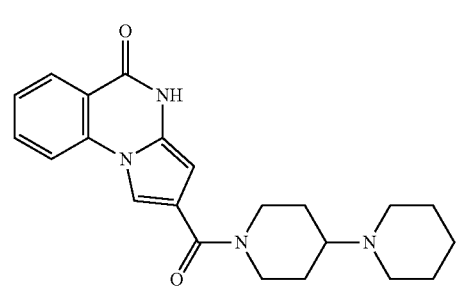 [SMILES: O=C(c1cc2[nH]c(=O)c3ccccc3n2c1)N1CCC(N2CCCCC2)CC1] | $^1$H-NMR (400 MHz, DMSO-d$_6$) δ 1.23-1.56 (m, 8H), 1.66-1.84 (m, 2H), 2.36-2.55 (m, 6H), 2.78-2.98 (m, 1H), 4.15-4.52 (m, 2H), 5.70 (d, J = 1.9 Hz, 1H), 7.43 (t, J = 7.9 Hz, 1H), 7.77-7.85 (m, 1H), 7.89 (d, J = 1.9 Hz, 1H), 8.08-8.16 (m, 2H), 11.78 (s, 1H). |
| 2-(Pyrrolidine-1-carbonyl)pyrrolo[1,2-a]quinazolin-5(4H)-one (Compound 1-34)<br />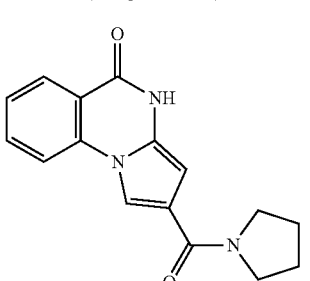 | $^1$H-NMR (400 MHz, DMSO-d$_6$) δ 1.78-2.00 (m, 4H), 3.40-3.50 (m, 2H), 3.65-3.80 (m, 2H), 5.89 (d, J = 1.7 Hz, 1H), 7.40-7.50 (m, 1H), 7.78-7.85 (m, 1H), 7.99 (d, J = 1.7 Hz, 1H), 8.10-8.15 (m, 1H), 8.19 (d, J = 8.0 Hz, 1H), 11.79 (s, 1H). |

TABLE 28

| | |
|---|---|
| 2-[4-(2,4-Difluorophenyl)piperazine-1-carbonyl]pyrrolo[1,2-a]quinazolin-5(4H)-one (Compound 1-35)<br />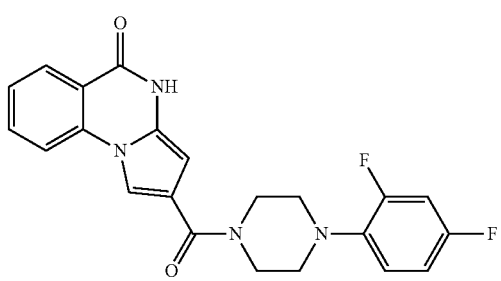 | $^1$H-NMR (400 MHz, DMSO-d$_6$) δ 2.97-3.02 (m, 4H), 3.78-3.85 (m, 4H), 5.76 (d, J = 1.8 Hz, 1H), 6.99-7.05 (m, 1H), 7.08-7.15 (m, 1H), 7.20-7.27 (m, 1H), 7.45 (t, J = 7.7 Hz, 1H), 7.82 (td, J = 7.7, 1.5 Hz, 1H), 7.96 (d, J = 1.8 Hz, 1H), 8.12-8.15 (m, 2H), 11.82 (s, 1H). |

TABLE 28-continued

| | |
|---|---|
| 2-[4-(Furo[3,2-c]pyridin-4-yl)piperazine-1-carbonyl]pyrrolo[1,2-a]quinazolin-5(4H)-one (Compound 1-36) 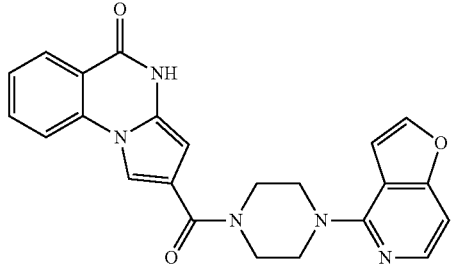 | $^1$H-NMR (400 MHz, DMSO-$d_6$) δ 3.71-3.76 (m, 4H), 3.81-3.87 (m, 4H), 5.79 (d, J = 1.7 Hz, 1H), 7.08 (dd, J = 5.8, 0.9 Hz, 1H), 7.22 (dd, J = 2.3, 0.9 Hz, 1H), 7.45 (t, J = 7.7 Hz, 1H), 7.83 (td, J = 7.7, 1.5 Hz, 1H), 7.97 (d, J = 2.3 Hz, 1H), 7.98 (d, J = 1.7 Hz, 1H), 8.00 (d, J = 5.8 Hz, 1H), 8.12-8.16 (m, 2H), 11.83 (s, 1H). |
| 2-[4-(1H-Indol-4-yl)piperazine-1-carbonyl]pyrrolo[1,2-a]quinazolin-5(4H)-one (Compound 1-37) 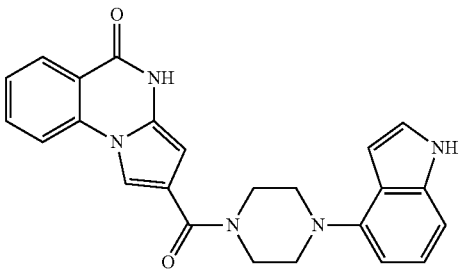 | $^1$H-NMR (400 MHz, DMSO-$d_6$) δ 3.13-3.18 (m, 4H), 3.87-3.92 (m, 4H), 5.78 (d, J = 1.7 Hz, 1H), 6.44-6.51 (m, 2H), 6.98 (t, J = 7.9 Hz, 1H), 7.06 (d, J = 7.9 Hz, 1H), 7.27 (t, J = 2.8 Hz, 1H), 7.45 (t, J = 7.6 Hz, 1H), 7.82 (td, J = 7.6, 1.7 Hz, 1H), 7.97 (d, J = 1.7 Hz, 1H), 8.11-8.16 (m, 2H), 11.07 (s, 1H), 11.82 (s, 1H). |

TABLE 29

| | |
|---|---|
| 2-[4-(4-Isopropoxyphenyl)piperazine-1-carbonyl]pyrrolo[1,2-a]quinazolin-5(4H)-one (Compound 1-38) 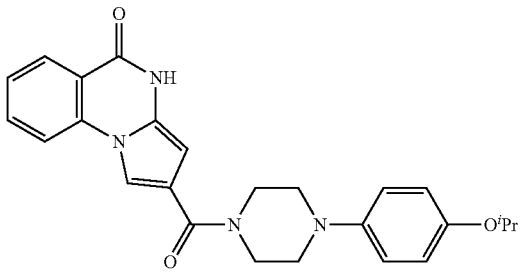 | $^1$H-NMR (400 MHz, DMSO-$d_6$) δ 1.22 (d, J = 5.9 Hz, 6H), 2.99-3.11 (m, 4H), 3.70-3.88 (m, 4H), 4.40-4.54 (m, 1H), 5.76 (d, J = 1.9 Hz, 1H), 6.82 (d, J = 9.0 Hz, 2H), 6.91 (d, J = 9.0 Hz, 2H), 7.45 (t, J = 7.7 Hz, 1H), 7.82 (t, J = 7.7 Hz, 1H), 7.95 (d, J = 1.9 Hz, 1H), 8.09-8.17 (m, 2H), 11.81 (s, 1H). |
| 2-[4-(4-Fluoro-2-methoxyphenyl)piperazine-1-carbonyl]pyrrolo[1,2-a]quinazolin-5(4H)-one (Compound 1-39) 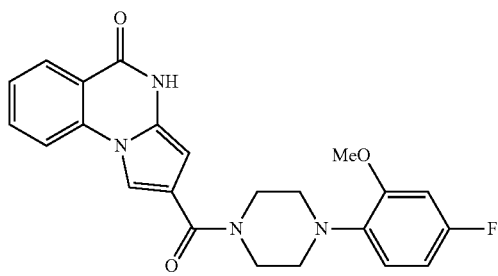 | $^1$H-NMR (400 MHz, DMSO-$d_6$) δ 2.88-2.97 (m, 4H), 3.70-3.87 (m, 4H), 3.81 (s, 3H), 5.76 (d, J = 1.5 Hz, 1H), 6.67-6.72 (m, 1H), 6.86-6.94 (m, 2H), 7.44 (dd, J = 7.8, 7.3 Hz, 1H), 7.82 (dd, J = 7.8, 6.8 Hz, 1H), 7.95 (d, J = 1.5 Hz, 1H), 8.10-8.15 (m, 2H), 11.82 (s, 1H). |

TABLE 29-continued

| | |
|---|---|
| 2-[4-(1,3-Benzodioxol-5-yl)piperazine-1-carbonyl]pyrrolo[1,2-a]quinazolin-5(4H)-one (Compound 1-40)<br>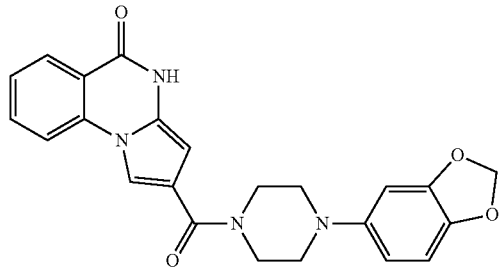 | $^1$H-NMR (400 MHz, DMSO-d$_6$) δ 3.00-3.10 (m, 4H), 3.70-3.85 (m, 4H), 5.76 (d, J = 1.7 Hz, 1H), 5.93 (s, 2H), 6.38 (dd, J = 8.5, 2.2 Hz, 1H), 6.72 (d, J = 2.2 Hz, 1H), 6.79 (d, J = 8.5 Hz, 1H), 7.45 (dd, J = 8.0, 7.6 Hz, 1H), 7.75-7.85 (m, 1H), 7.95 (d, J = 1.7 Hz, 1H), 8.10-8.16 (m, 2H), 11.82 (s, 1H). |

TABLE 30

| | |
|---|---|
| 7-[4-(4-Fluorophenyl)piperazine-1-carbonyl]pyrrolo[1,2-a]thieno[2,3-e]pyrimidin-4(5H)-one (Compound 1-41)<br>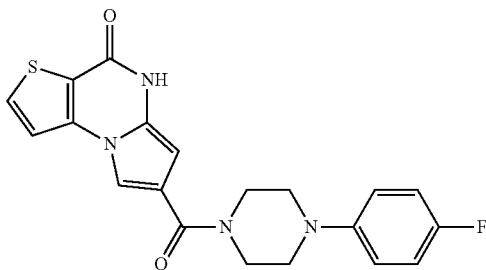 | $^1$H-NMR (400 MHz, DMSO-d$_6$) δ 3.10-3.20 (m, 4H), 3.70-3.90 (m, 4H), 5.80 (d, J = 1.7 Hz, 1H), 6.98-7.12 (m, 4H), 7.82 (d, J = 1.7 Hz, 1H), 7.85 (d, J = 5.4 Hz, 1H), 8.23 (d, J = 5.4 Hz, 1H), 11.86 (s, 1H). |
| 7-[4-(4-Chlorophenyl)piperazine-1-carbonyl]pyrrolo[1,2-a]thieno[2,3-e]pyrimidin-4(5H)-one (Compound 1-42)<br>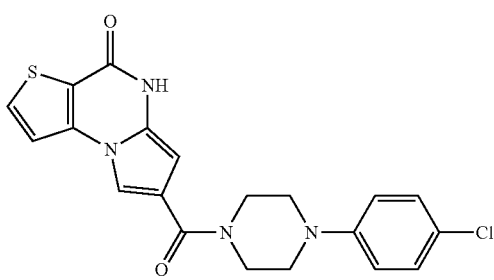 | $^1$H-NMR (400 MHz, DMSO-d$_6$) δ 3.15-3.30 (m, 4H), 3.70-3.90 (m, 4H), 5.80 (d, J = 1.7 Hz, 1H), 6.98 (d, J = 9.0 Hz, 2H), 7.26 (d, J = 9.0 Hz, 2H), 7.82 (d, J = 1.7 Hz, 1H), 7.86 (d, J = 5.4 Hz, 1H), 8.23 (d, J = 5.4 Hz, 1H), 11.87 (s, 1H). |
| 7-(Pyrrolidine-1-carbonyl)pyrrolo[1,2-a]thieno[2,3-e]pyrimidin-4(5H)-one (Compound 1-43)<br>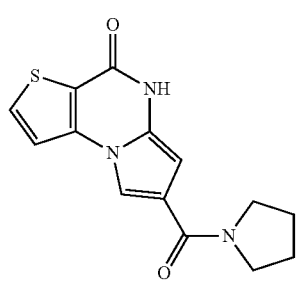 | $^1$H-NMR (400 MHz, DMSO-d$_6$) δ 1.77-2.00 (m, 4H), 3.40-3.55 (m, 2H), 3.60-3.80 (m, 2H), 5.94 (d, J = 1.7 Hz, 1H), 7.88 (d, J = 1.7 Hz, 1H), 7.91 (d, J = 5.4 Hz, 1H), 8.23 (d, J = 5.4 Hz, 1H), 11.84 (s, 1H). |

TABLE 31

| Compound | ¹H-NMR |
|---|---|
| 7-Fluoro-2-[4-(pyridin-2-yl)piperazine-1-carbonyl]pyrrolo[1,2-a]quinazolin-5(4H)-one (Compound 1-44) | ¹H-NMR (400 MHz, DMSO-d$_6$) δ 3.54-3.60 (m, 4H), 3.73-3.79 (m, 4H), 5.78 (d, J = 1.8 Hz, 1H), 6.67 (dd, J = 7.0, 4.9 Hz, 1H), 6.86 (d, J = 8.8 Hz, 1H), 7.57 (ddd, J = 8.8, 7.0, 2.0 Hz, 1H), 7.74 (td, J = 8.8, 3.1 Hz, 1H), 7.82 (dd, J = 8.8, 3.1 Hz, 1H), 7.98 (d, J = 1.8 Hz, 1H), 8.14 (dd, J = 4.9, 2.0 Hz, 1H), 8.23 (dd, J = 8.8, 4.3 Hz, 1H), 11.97 (s, 1H). |
| 7-Fluoro-2-[4-(4-fluorophenyl)piperazine-1-carbonyl]pyrrolo[1,2-a]quinazolin-5(4H)-one (Compound 1-45) | ¹H-NMR (500 MHz, DMSO-d$_6$) δ 3.10-3.14 (m, 4H), 3.76-3.82 (m, 4H), 5.77 (d, J = 1.8 Hz, 1H), 6.87-7.12 (m, 4H), 7.75 (td, J = 8.8, 3.2 Hz, 1H), 7.82 (dd, J = 8.8, 3.2 Hz, 1H), 7.98 (d, J = 1.8 Hz, 1H), 8.23 (dd, J = 8.8, 4.3 Hz, 1H), 11.97 (s, 1H). |
| 2-[4-(4-Fluorophenyl)homopiperazine-1-carbonyl]pyrrolo[1,2-a]quinazolin-5(4H)-one (Compound 1-46) | ¹H-NMR (500 MHz, DMSO-d$_6$, 100° C.) δ 1.90-2.00 (m, 2H), 3.55 (t, J = 6.1 Hz, 2H), 3.58-3.65 (m, 4H), 3.82 (t, J = 5.8 Hz, 2H), 5.71 (d, J = 1.5 Hz, 1H), 6.70-6.80 (m, 2H), 6.90-7.00 (m, 2H), 7.43 (d, J = 7.6 Hz, 1H), 7.63 (d, J = 1.5 Hz, 1H), 7.77-7.81 (m, 1H), 7.97 (d, J = 8.3 Hz, 1H), 8.15 (d, J = 7.6 Hz, 1H), 11.44 (s, 1H). |

TABLE 32

| Compound | ¹H-NMR |
|---|---|
| 2-[4-(tert-Butoxycarbonyl)homopiperazine-1-carbonyl]pyrrolo[1,2-a]quinazolin-5(4H)-one (Compound 1-47) | ¹H-NMR (500 MHz, DMSO-d$_6$, 100° C.) δ 1.39 (s, 9H), 1.76-1.82 (m, 2H), 3.42 (t, J = 5.8 Hz, 2H), 3.51 (t, J = 5.5 Hz, 2H), 3.64 (t, J = 5.5 Hz, 2H), 3.75 (t, J = 5.5 Hz, 2H), 5.79 (d, J = 1.8 Hz, 1H), 7.41-7.45 (m, 1H), 7.76 (d, J = 1.8 Hz, 1H), 7.77-7.82 (m, 1H), 8.01 (d, J = 8.2 Hz, 1H), 8.15 (dd, J = 7.9, 1.2 Hz, 1H), 11.46 (s, 1H). |

TABLE 32-continued

| | |
|---|---|
| 2-[4-(tert-Butoxycarbonyl)piperazine-1-carbonyl]pyrrolo[1,2-a]quinazolin-5(4H)-one (Compound 1-48)<br>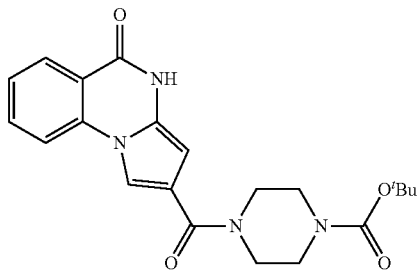 | $^1$H-NMR (500 MHz, DMSO-$d_6$) δ 1.42 (s, 9H), 3.30-3.45 (m, 4H), 3.57-3.70 (m, 4H), 5.74 (d, J = 2.1 Hz, 1H), 7.40-7.50 (m, 1H), 7.79-7.83 (m, 1H), 7.92 (d, J = 2.1 Hz, 1H), 8.10-8.16 (m, 2H), 11.80 (s, 1H). |
| 2-(Phenylaminocarbonyl)pyrrolo[1,2-a]quinazolin-5(4H)-one (Compound 1-49)<br>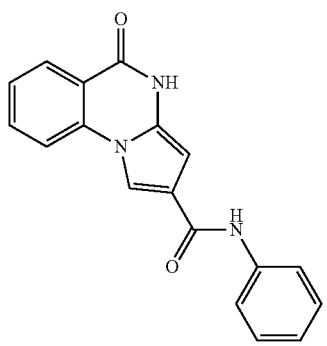 | $^1$H-NMR (400 MHz, DMSO-$d_6$) δ 6.27 (d, J = 2.0 Hz, 1H), 7.07 (tt, J = 8.3, 1.1 Hz, 1H), 7.34 (t, J = 8.3 Hz, 2H), 7.47 (t, J = 8.1 Hz, 1H), 7.77 (dd, J = 8.3, 1.1 Hz, 2H), 7.85 (td, J = 8.1, 1.3 Hz, 1H), 8.09 (d, J = 8.1 Hz, 1H), 8.15 (dd, J = 8.1, 1.3 Hz, 1H), 8.29 (d, J = 2.0 Hz, 1H), 9.81 (s, 1H), 11.96 (s, 1H). |

TABLE 33

| | |
|---|---|
| 2-(4-Methylhomopiperazine-1-carbonyl)pyrrolo[1,2-a]quinazolin-5(4H)-one (Compound 1-50)<br>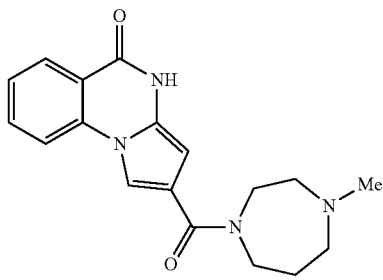 | $^1$H-NMR (500 MHz, DMSO-$d_6$, 100° C.) δ 1.15-1.90 (m, 2H), 2.34 (s, 3H), 2.55-2.64 (m, 2H), 2.65-2.83 (m, 2H), 3.60-3.73 (m, 4H), 5.79 (d, J = 1.8 Hz, 1H), 7.43 (ddd, J = 8.2, 7.3, 0.9 Hz, 1H), 7.76 (d, J = 1.8 Hz, 1H), 7.79 (ddd, J = 8.2, 7.3, 1.5 Hz, 1H), 8.03 (dd, J = 8.2, 0.9 Hz, 1H), 8.15 (dd, J = 7.3, 1.5 Hz, 1H), 11.43 (s, 1H). |
| 2-[(2-Dimethylaminoethyl)aminocarbonyl]pyrrolo[1,2-a]quinazolin-5(4H)-one (Compound 1-51)<br>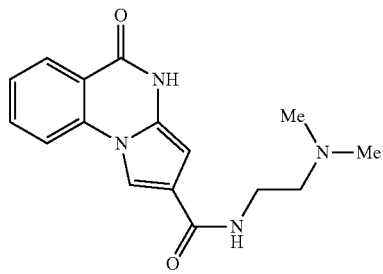 | $^1$H-NMR (400 MHz, DMSO-$d_6$) δ 2.21 (s, 6H), 2.35-2.45 (m, 2H), 3.20-3.40 (m, 2H), 6.04 (d, J = 2.0 Hz, 1H), 7.40-7.48 (m, 1H), 7.79-7.86 (m, 1H), 7.95-8.14 (m, 4H), 11.86 (s, 1H). |

TABLE 33-continued

| | |
|---|---|
| 2-[(Pyridin-4-ylmethyl)aminocarbonyl]pyrrolo[1,2-a]quinazolin-5(4H)-one (Compound 1-52)<br>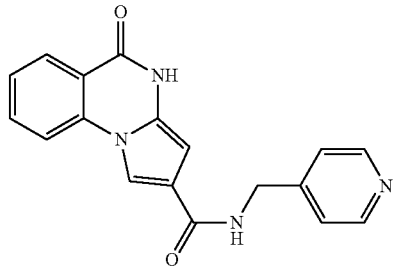 | $^1$H-NMR (400 MHz, DMSO-d$_6$) δ 4.46 (d, J = 5.9 Hz, 2H), 6.12 (d, J = 1.9 Hz, 1H), 7.30 (d, J = 5.9 Hz, 2H), 7.45 (t, J = 8.3 Hz, 1H), 7.82 (td, J = 8.3, 1.6 Hz, 1H), 8.06 (d, J = 8.3 Hz, 1H), 8.13 (dd, J = 8.3, 1.6 Hz, 1H), 8.14 (d, J = 1.9 Hz, 1H), 8.50 (d, J = 5.9 Hz, 2H), 8.72 (t, J = 5.9 Hz, 1H), 11.90 (s, 1H). |

TABLE 34

| | |
|---|---|
| 2-[2-(Morpholin-4-ylethyl)aminocarbonyl]pyrrolo[1,2-a]quinazolin-5(4H)-one (Compound 1-53)<br>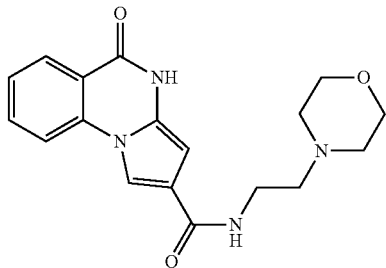 | $^1$H-NMR (400 MHz, DMSO-d$_6$) δ 2.35-2.48 (m, 4H), 2.49-2.55 (m, 2H), 3.27-3.41 (m, 2H), 3.58 (t, J = 4.5 Hz, 4H), 6.04 (d, J = 2.0 Hz, 1H), 7.44 (t, J = 7.8 Hz, 1H), 7.82 (t, J = 7.8 Hz, 1H), 7.95-8.10 (m, 3H), 8.12 (d, J = 7.8 Hz, 1H), 11.86 (s, 1H). |
| 2-(Benzylaminocarbonyl)pyrrolo[1,2-a]quinazolin-5(4H)-one (Compound 1-54)<br>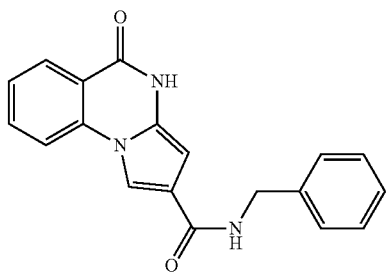 | $^1$H-NMR (400 MHz, DMSO-d$_6$) δ 4.45 (d, J = 6.0 Hz, 2H), 6.11 (d, J = 1.8 Hz, 1H), 7.22-7.35 (m, 5H), 7.44 (t, J = 7.9 Hz, 1H), 7.82 (td, J = 7.9, 1.3 Hz, 1H), 8.03 (d, J = 7.9 Hz, 1H), 8.13 (dd, J = 7.9, 1.3 Hz, 1H), 8.13 (d, J = 1.8 Hz, 1H), 8.61 (t, J = 6.0 Hz, 1H), 11.87 (s, 1H). |
| 2-(2-Phenylethylaminocarbonyl)pyrrolo[1,2-a]quinazolin-5(4H)-one (Compound 1-55)<br>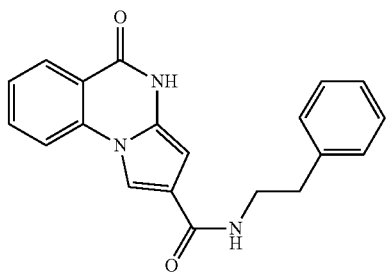 | $^1$H-NMR (400 MHz, DMSO-d$_6$) δ 2.83 (t, J = 7.4 Hz, 2H), 3.44 (td, J = 7.4, 5.6 Hz, 2H), 6.04 (d, J = 1.8 Hz, 1H), 7.18-7.32 (m, 5H), 7.44 (t, J = 8.1 Hz, 1H), 7.81 (td, J = 8.1, 1.5 Hz, 1H), 8.03 (d, J = 8.1 Hz, 1H), 8.06 (d, J = 1.8 Hz, 1H), 8.12 (dd, J = 8.1, 1.5 Hz, 1H), 8.15 (t, J = 5.6 Hz, 1H), 11.85 (s, 1H). |

TABLE 35

| | |
|---|---|
| 2-(3-Phenylpropylaminocarbonyl)pyrrolo[1,2-a]quinazolin-5(4H)-one (Compound 1-56)<br>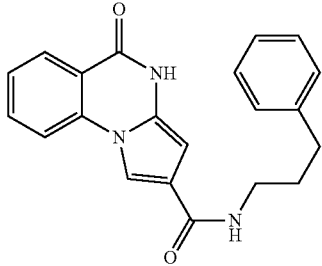 | $^1$H-NMR (400 MHz, DMSO-$d_6$) δ 1.77-1.85 (m, 2H), 2.63 (t, J = 7.6 Hz, 2H), 3.24 (td, J = 7.6, 5.6 Hz, 2H), 6.07 (d, J = 2.0 Hz, 1H), 7.16-7.31 (m, 5H), 7.44 (t, J = 8.0 Hz, 1H), 7.81 (td, J = 8.0, 1.3 Hz, 1H), 8.04 (d, J = 8.0 Hz, 1H), 8.07 (d, J = 2.0 Hz, 1H), 8.07 (t, J = 5.6 Hz, 1H), 8.12 (dd, J = 8.0, 1.3 Hz, 1H), 11.85 (s, 1H). |
| 2-[4-[2-(2-Dimethylaminoethoxy)-4-fluorophenyl]piperazine-1-carbonyl]pyrrolo[1,2-a]quinazolin-5(4H)-one (Compound 1-57)<br>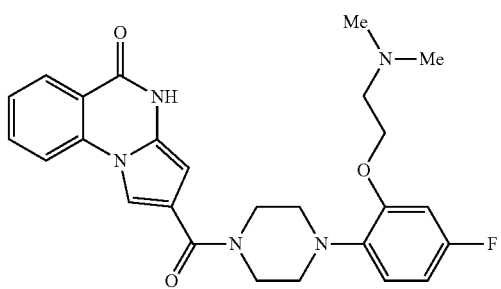 | $^1$H-NMR (400 MHz, DMSO-$d_6$) δ 2.25 (s, 6H), 2.66 (t, J = 5.6 Hz, 2H), 2.90-3.03 (m, 4H), 3.70-3.83 (m, 4H), 4.06 (t, J = 5.6 Hz, 2H), 5.75 (d, J = 1.7 Hz, 1H), 6.65-6.72 (m, 1H), 6.86-6.91 (m, 2H), 7.42-7.48 (m, 1H), 7.79-7.85 (m, 1H), 7.95 (d, J = 1.7 Hz, 1H), 8.10-8.17 (m, 2H), 11.81 (s, 1H). |
| 2-[4-(Morpholin-4-yl)piperidine-1-carbonyl]pyrrolo[1,2-a]quinazolin-5(4H)-one (Compound 1-58)<br>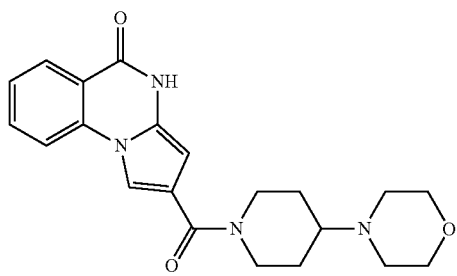 | $^1$H-NMR (400 MHz, DMSO-$d_6$) δ 1.39-1.51 (m, 2H), 1.88-2.02 (m, 2H), 2.47-2.49 (m, 2H), 2.84-2.90 (m, 3H), 3.41-3.46 (m, 2H), 3.59-3.79 (m, 4H), 4.34-4.48 (m, 2H), 5.72 (d, J = 2.0 Hz, 1H), 7.45 (t, J = 7.6 Hz, 1H), 7.82 (td, J = 7.6, 1.7 Hz, 1H), 7.92 (d, J = 2.0 Hz, 1H), 8.10-8.15 (m, 2H), 11.82 (s, 1H). |

Example 2

2-[4-(4-Fluorophenyl)piperazin-1-ylmethyl]pyrrolo[1,2-a]quinazolin-5 (4H)-one (Compound 2-1)

Under cooling on ice, lithium aluminum hydride (657 mg, 17.3 mmol) was added to a solution of 2-[4-(4-fluorophenyl)piperazine-1-carbonyl]pyrrolo[1,2-a]quinazolin-5(4H)-one (the above Compound 1-1, 3.38 g, 8.66 mmol) in anhydrous tetrahydrofuran (75 mL). This reaction solution was stirred at room temperature for 2 hours. A small amount of ethyl acetate was added dropwise to the reaction solution, and then a saturated aqueous solution of sodium potassium tartrate tetrahydrate (100 mL), and water (100 mL) were added sequentially. The mixture was extracted twice with chloroform (100 mL). The organic layer was dried over anhydrous magnesium sulfate, and concentrated under reduced pressure. The obtained residue was collected by filtration with ethanol, to obtain the title compound (2.85 g, yield: 87%) as a pale yellow powder.

TABLE 36

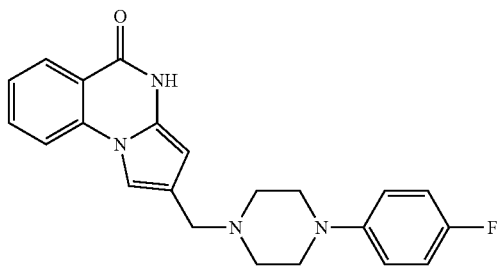 [SMILES: O=c1[nH]c2cc(CN3CCN(c4ccc(F)cc4)CC3)cn2c2ccccc12]

¹H-NMR (500 MHz, DMSO-d₆) δ 2.45-2.60 (m, 4H), 3.00-3.15 (m, 4H), 3.43 (s, 2H), 5.57 (d, J = 1.7 Hz, 1H), 6.90-6.98 (m, 2H), 7.00-7.10 (m, 2H), 7.36 (dd, J = 8.0, 7.3 Hz, 1H), 7.48 (d, J = 1.7 Hz, 1H), 7.74-7.80 (m, 1H), 7.95 (d, J = 8.0 Hz, 1H), 8.09 (dd, J = 8.0, 1.5 Hz, 1H), 11.66 (s, 1H).

In the following, by using any one of Compounds 1-2 to 1-45, 1-57 and 1-58, Compounds 2-2 to 2-47 were obtained according to the production method for Compound 2-1.

TABLE 37

2-[4-(4-Chlorobenzyl)piperazin-1-ylmethyl]pyrrolo[1,2-a]quinazolin-5(4H)-one (Compound 2-2)

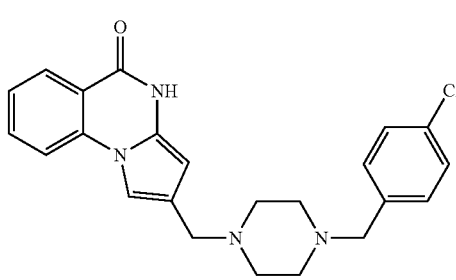

¹H-NMR (400 MHz, DMSO-d₆) δ 2.20-2.60 (m, 8H), 3.37 (s, 2H), 3.44 (s, 2H), 5.52 (d, J = 1.7 Hz, 1H), 7.29-7.40 (m, 5H), 7.42 (d, J = 1.7 Hz, 1H), 7.75 (ddd, J = 8.5, 7.1, 1.5 Hz, 1H), 7.93 (d, J = 8.5 Hz, 1H), 8.08 (dd, J = 7.1, 1.5 Hz, 1H), 11.65 (s, 1H).

2-[4-(Thiazol-2-yl)piperazin-1-ylmethyl]pyrrolo[1,2-a]quinazolin-5(4H)-one (Compound 2-3)

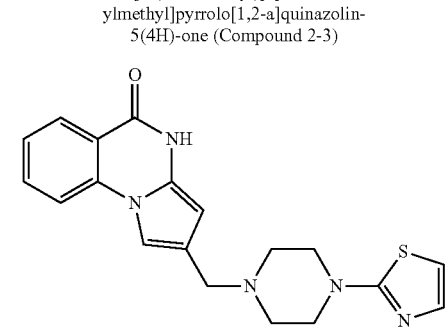

¹H-NMR (400 MHz, DMSO-d₆) δ 2.51-2.53 (m, 4H), 3.38-3.41 (m, 4H), 3.45 (s, 2H), 5.57 (d, J = 1.7 Hz, 1H), 6.83 (d, J = 3.7 Hz, 1H), 7.15 (d, J = 3.7 Hz, 1H), 7.36 (t, J = 8.0 Hz, 1H), 7.48 (d, J = 1.7 Hz, 1H), 7.77 (td, J = 8.0, 1.5 Hz, 1H), 7.94 (d, J = 8.0 Hz, 1H), 8.09 (dd, J = 8.0, 1.5 Hz, 1H), 11.67 (s, 1H).

2-(4-Phenylpiperazin-1-ylmethyl)pyrrolo[1,2-a]quinazolin-5(4H)-one (Compound 2-4)

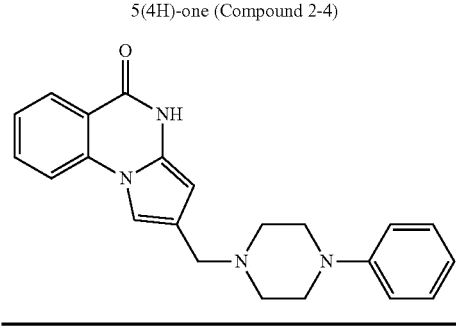

¹H-NMR (400 MHz, DMSO-d₆) δ 2.54 (t, J = 5.0 Hz, 4H), 3.13 (t, J = 5.0 Hz, 4H), 3.44 (s, 2H), 5.58 (d, J = 1.7 Hz, 1H), 6.76 (tt, J = 7.5, 1.3 Hz, 1H), 6.91 (dt, J = 7.5, 1.3 Hz, 2H), 7.19 (t, J = 7.5 Hz, 2H), 7.36 (ddd, J = 8.0, 7.3, 1.3 Hz, 1H), 7.49 (d, J = 1.7 Hz, 1H), 7.77 (ddd, J = 8.0, 7.3, 1.3 Hz, 1H), 7.95 (dd, J = 8.0, 1.3 Hz, 1H), 8.09 (dd, J = 7.3, 1.3 Hz, 1H), 11.67 (s, 1H).

TABLE 38

| Compound | ¹H-NMR |
|---|---|
| 2-(4-Phenylpiperidin-1-ylmethyl)pyrrolo[1,2-a]quinazolin-5(4H)-one (Compound 2-5) | ¹H-NMR (500 MHz, DMSO-d₆) δ 1.57-1.82 (m, 4H), 1.97-2.12 (m, 1H), 2.40-2.60 (m, 2H), 2.93-3.10 (m, 2H), 3.36-3.51 (m, 2H), 5.54-5.61 (m, 1H), 7.17 (t, J = 7.2 Hz, 1H), 7.20-7.33 (m, 4H), 7.36 (t, J = 7.6 Hz, 1H), 7.43-7.51 (m, 1H), 7.73-7.81 (m, 1H), 7.95 (d, J = 8.0 Hz, 1H), 8.09 (dd, J = 8.0, 1.2 Hz, 1H), 11.68 (s, 1H). |
| 2-(4-Phenyl-1,2,3,6-tetrahydropyridin-1-ylmethyl)pyrrolo[1,2-a]quinazolin-5(4H)-one (Compound 2-6) | ¹H-NMR (400 MHz, DMSO-d₆) δ 2.49 (s, 2H), 2.68 (t, J = 5.6 Hz, 2H), 3.10 (s, 2H), 3.50 (s, 2H), 5.58 (d, J = 1.7 Hz, 1H), 6.15 (s, 1H), 7.23 (t, J = 7.3 Hz, 1H), 7.30-7.38 (m, 3H), 7.42 (d, J = 7.3 Hz, 2H), 7.50 (d, J = 1.7 Hz, 1H), 7.76 (ddd, J = 8.0, 7.3, 1.5 Hz, 1H), 7.95 (d, J = 8.0 Hz, 1H), 8.10 (dd, J = 8.0, 1.5 Hz, 1H), 11.80 (s, 1H). |
| 2-[4-(4-Chlorophenyl)-1,2,3,6-tetrahydropyridin-1-ylmethyl]pyrrolo[1,2-a]quinazolin-5(4H)-one (Compound 2-7) | ¹H-NMR (400 MHz, DMSO-d₆) δ 2.46 (s, 2H), 2.67 (t, J = 5.6 Hz, 2H), 3.09 (d, J = 3.2 Hz, 2H), 3.50 (s, 2H), 5.58 (d, J = 1.7 Hz, 1H), 6.20 (s, 1H), 7.34-7.39 (m, 3H), 7.43-7.46 (m, 2H), 7.49 (d, J = 1.7 Hz, 1H), 7.76 (ddd, J = 8.0, 7.3, 1.6 Hz, 1H), 7.95 (d, J = 8.0 Hz, 1H), 8.09 (dd, J = 8.0, 1.6 Hz, 1H), 11.68 (s, 1H). |

TABLE 39

| Compound | ¹H-NMR |
|---|---|
| 2-[4-(4-Fluorophenyl)-1,2,3,6-tetrahydropyridin-1-ylmethyl]pyrrolo[1,2-a]quinazolin-5(4H)-one (Compound 2-8) | ¹H-NMR (400 MHz, DMSO-d₆) δ 2.47 (s, 2H), 2.67 (t, J = 5.6 Hz, 2H), 3.09 (s, 2H), 3.50 (s, 2H), 5.58 (d, J = 1.5 Hz, 1H), 6.12 (s, 1H), 7.14 (t, J = 8.9 Hz, 2H), 7.36 (t, J = 7.6 Hz, 1H), 7.44-7.47 (m, 2H), 7.49 (brs, 1H), 7.76 (ddd, J = 8.1, 7.3, 1.6 Hz, 1H), 7.95 (d, J = 8.1 Hz, 1H), 8.09 (dd, J = 8.1, 1.6 Hz, 1H), 11.68 (s, 1H). |

TABLE 39-continued

| | |
|---|---|
| 2-[4-(2-Fluorophenyl)piperazin-1-ylmethyl]pyrrolo[1,2-a]quinazolin-5(4H)-one (Compound 2-9) | ¹H-NMR (400 MHz, DMSO-d₆) δ 2.53-2.61 (m, 4H), 2.98-3.05 (m, 4H), 3.45 (s, 2H), 5.58 (s, 1H), 6.92-7.15 (m, 4H), 7.36 (t, J = 7.8 Hz, 1H), 7.49 (s, 1H), 7.77 (td, J = 7.8, 1.5 Hz, 1H), 7.95 (d, J = 7.8 Hz, 1H), 8.10 (dd, J = 7.8, 1.5 Hz, 1H), 11.68 (s, 1H). |
| 2-(4-Methylpiperazin-1-ylmethyl)pyrrolo[1,2-a]quinazolin-5(4H)-one (Compound 2-10) | ¹H-NMR (500 MHz, DMSO-d₆) δ 2.14 (s, 3H), 2.22-2.32 (m, 4H), 2.35-2.44 (m, 4H), 3.35 (s, 2H), 5.53 (d, J = 1.7 Hz, 1H), 7.35 (t, J = 8.0 Hz, 1H), 7.43 (d, J = 1.7 Hz, 1H), 7.76 (td, J = 8.0, 1.5 Hz, 1H), 7.93 (d, J = 8.0 Hz, 1H), 8.08 (dd, J = 8.0, 1.5 Hz, 1H), 11.65 (s, 1H). |

TABLE 40

| | |
|---|---|
| 2-(4-Benzylpiperazin-1-ylmethyl)pyrrolo[1,2-a]quinazolin-5(4H)-one (Compound 2-11) | ¹H-NMR (500 MHz, DMSO-d₆) δ 2.20-2.60 (m, 8H), 3.36 (s, 2H), 3.45 (s, 2H), 5.52 (d, J = 1.8 Hz, 1H), 7.20-7.38 (m, 6H), 7.43 (d, J = 1.8 Hz, 1H), 7.75 (td, J = 7.3, 1.5 Hz, 1H), 7.93 (d, J = 7.3 Hz, 1H), 8.08 (dd, J = 7.3, 1.5 Hz, 1H), 11.65 (s, 1H). |
| 2-[4-(4-Chlorophenyl)piperazin-1-ylmethyl]pyrrolo[1,2-a]quinazolin-5(4H)-one (Compound 2-12) | ¹H-NMR (400 MHz, DMSO-d₆) δ 2.40-2.60 (m, 4H), 3.13 (t, J = 4.8 Hz, 4H), 3.43 (s, 2H), 5.57 (d, J = 1.7 Hz, 1H), 6.92 (d, J = 9.3 Hz, 2H), 7.21 (d, J = 9.2 Hz, 2H), 7.36 (ddd, J = 8.2, 7.3 Hz, 1H), 7.48 (d, J = 1.7 Hz, 1H), 7.76 (ddd, J = 8.2, 7.3, 1.3 Hz, 1H), 7.94 (dd, J = 8.2, 1.3 Hz, 1H), 8.09 (dd, J = 8.2, 1.3 Hz, 1H), 11.67 (s, 1H). |

TABLE 40-continued

| | |
|---|---|
| 2-[4-(4-Fluorobenzyl)piperazin-1-ylmethyl]pyrrolo[1,2-a]quinazolin-5(4H)-one (Compound 2-13)<br>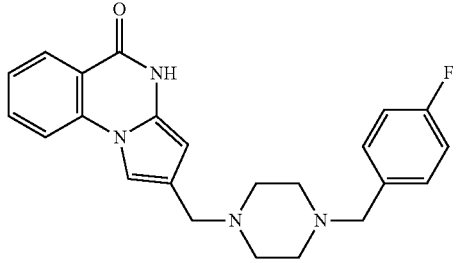 | $^1$H-NMR (400 MHz, DMSO-d$_6$) δ 2.37 (brs, 8H), 3.36 (s, 2H), 3.43 (s, 2H), 5.52 (d, J = 1.7 Hz, 1H), 7.10-7.14 (m, 2H), 7.29-7.32 (m, 2H), 7.35 (t, J = 7.6 Hz, 1H), 7.42 (d, J = 1.7 Hz, 1H), 7.75 (ddd, J = 8.0, 7.6, 1.6 Hz, 1H), 7.92 (d, J = 8.0 Hz, 1H), 8.08 (dd, J = 7.6, 1.6 Hz, 1H), 11.65 (s, 1H). |

TABLE 41

| | |
|---|---|
| 2-[4-(4-Fluorophenyl)piperidin-1-ylmethyl]pyrrolo[1,2-a]quinazolin-5(4H)-one (Compound 2-14)<br>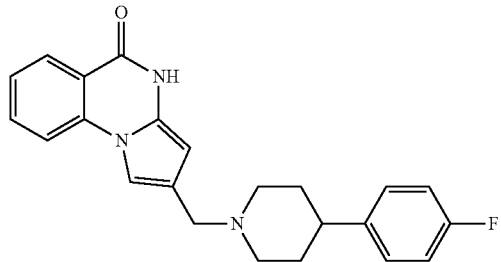 | $^1$H-NMR (400 MHz, DMSO-d$_6$) δ 1.53-1.79 (m, 4H), 1.95-2.08 (m, 2H), 2.43-2.54 (m, 1H), 2.99 (d, J = 11.5 Hz, 2H), 3.41 (s, 2H), 5.56 (d, J = 1.5 Hz, 1H), 7.05-7.14 (m, 2H), 7.24-7.32 (m, 2H), 7.36 (t, J = 7.9 Hz, 1H), 7.46 (d, J = 1.5 Hz, 1H), 7.72-7.80 (m, 1H), 7.94 (d, J = 7.9 Hz, 1H), 8.09 (dd, J = 7.9, 1.2 Hz, 1H), 11.66 (s, 1H). |
| 2-[4-(3-Fluorophenyl)piperazin-1-ylmethyl]pyrrolo[1,2-a]quinazolin-5(4H)-one (Compound 2-15)<br>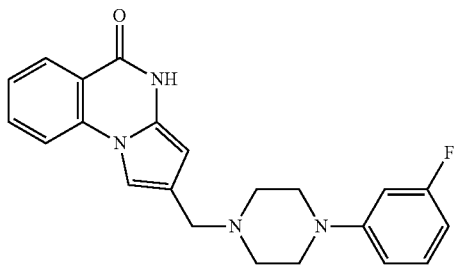 | $^1$H-NMR (400 MHz, DMSO-d$_6$) δ 2.51-2.54 (m, 4H), 3.15-3.19 (m, 4H), 3.43 (s, 2H), 5.57 (d, J = 1.7 Hz, 1H), 6.52 (td, J = 8.1, 2.1 Hz, 1H), 6.69-6.75 (m, 2H), 7.19 (q, J = 8.1 Hz, 1H), 7.36 (t, J = 8.0 Hz, 1H), 7.48 (d, J = 1.7 Hz, 1H), 7.77 (td, J = 8.0, 1.5 Hz, 1H), 7.95 (d, J = 8.0 Hz, 1H), 8.09 (dd, J = 8.0, 1.5 Hz, 1H), 11.67 (s, 1H). |
| 2-[4-(4-Methoxyphenyl)piperazin-1-ylmethyl]pyrrolo[1,2-a]quinazolin-5(4H)-one (Compound 2-16)<br>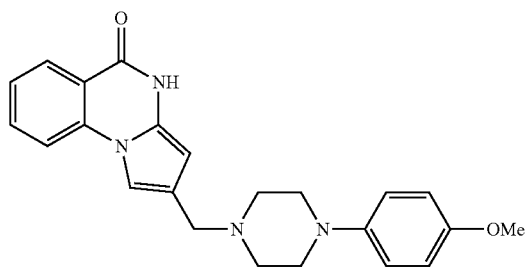 | $^1$H-NMR (400 MHz, DMSO-d$_6$) δ 2.52-2.55 (m, 4H), 2.99-3.03 (m, 4H), 3.43 (s, 2H), 3.67 (s, 3H), 5.57 (d, J = 1.6 Hz, 1H), 6.80 (d, J = 9.1 Hz, 2H), 6.87 (d, J = 9.1 Hz, 2H), 7.36 (t, J = 8.0 Hz, 1H), 7.48 (d, J = 1.6 Hz, 1H), 7.77 (td, J = 8.0, 1.6 Hz, 1H), 7.95 (d, J = 8.0 Hz, 1H), 8.09 (dd, J = 8.0, 1.6 Hz, 1H), 11.66 (s, 1H). |

TABLE 42

| Compound | ¹H-NMR |
|---|---|
| 2-[4-(Pyridin-2-yl)piperazin-1-ylmethyl]pyrrolo[1,2-a]quinazolin-5(4H)-one (Compound 2-17) | ¹H-NMR (400 MHz, DMSO-d₆) δ 2.46-2.49 (m, 4H), 3.43 (s, 2H), 3.45-3.49 (m, 4H), 5.58 (d, J = 1.6 Hz, 1H), 6.62 (dd, J = 7.0, 5.0 Hz, 1H), 6.79 (d, J = 8.5 Hz, 1H), 7.36 (t, J = 7.9 Hz, 1H), 7.48 (d, J = 1.6 Hz, 1H), 7.51 (ddd, J = 8.5, 7.0, 1.5 Hz, 1H), 7.77 (td, J = 7.9, 1.5 Hz, 1H), 7.95 (d, J = 7.9 Hz, 1H), 8.09 (dd, J = 5.0, 1.5 Hz, 1H), 8.09 (dd, J = 7.9, 1.5 Hz, 1H), 11.67 (s, 1H). |
| 2-[4-(Pyridin-3-yl)piperazin-1-ylmethyl]pyrrolo[1,2-a]quinazolin-5(4H)-one (Compound 2-18) | ¹H-NMR (400 MHz, DMSO-d₆) δ 2.53-2.58 (m, 4H), 3.17-3.22 (m, 4H), 3.44 (s, 2H), 5.57 (d, J = 1.7 Hz, 1H), 7.19 (dd, J = 8.3, 4.6 Hz, 1H), 7.30 (ddd, J = 8.3, 2.9, 1.2 Hz, 1H), 7.36 (t, J = 8.1 Hz, 1H), 7.49 (d, J = 1.7 Hz, 1H), 7.77 (td, J = 8.1, 1.3 Hz, 1H), 7.95 (d, J = 8.1 Hz, 1H), 7.98 (dd, J = 4.6, 1.2 Hz, 1H), 8.09 (dd, J = 8.1, 1.3 Hz, 1H), 8.28 (d, J = 2.9 Hz, 1H), 11.68 (s, 1H). |
| 2-[N-Methyl-N-(3-phenylpropyl)aminomethyl]pyrrolo[1,2-a]quinazolin-5(4H)-one (Compound 2-19) | ¹H-NMR (400 MHz, DMSO-d₆) δ 1.71-1.79 (m, 2H), 2.18 (s, 3H), 2.36 (s, 2H), 2.59 (t, J = 7.6 Hz, 2H), 3.41 (s, 2H), 5.56 (d, J = 1.5 Hz, 1H), 7.11-7.15 (m, 1H), 7.17-7.25 (m, 4H), 7.36 (t, J = 7.6 Hz, 1H), 7.43 (s, 1H), 7.77 (ddd, J = 8.0, 7.6, 1.5 Hz, 1H), 7.93 (d, J = 8.0 Hz, 1H), 8.10 (dd, J = 7.6, 1.5 Hz, 1H), 11.66 (s, 1H). |

TABLE 43

| Compound | ¹H-NMR |
|---|---|
| 2-[4-(4-Bromophenyl)piperazin-1-ylmethyl]pyrrolo[1,2-a]quinazolin-5(4H)-one (Compound 2-20) | ¹H-NMR (400 MHz, DMSO-d₆) δ 2.40-2.60 (m, 4H), 3.00-3.20 (m, 4H), 3.43 (s, 2H), 5.57 (d, J = 1.7 Hz, 1H), 6.88 (d, J = 9.0 Hz, 2H), 7.29-7.40 (m, 3H), 7.48 (d, J = 1.7 Hz, 1H), 7.76 (ddd, J = 8.5, 8.3, 1.5 Hz, 1H), 7.94 (d, J = 8.3 Hz, 1H), 8.09 (dd, J = 8.3, 1.5 Hz, 1H), 11.82 (br s, 1H). |

TABLE 43-continued

| 2-(1,2,3,4-Tetrahydroisoquinolin-2(1H)-ylmethyl)pyrrolo[1,2-a]quinazolin-5(4H)-one (Compound 2-21) 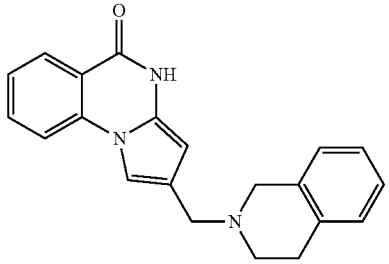 | $^1$H-NMR (400 MHz, DMSO-d$_6$) δ 2.68-2.73 (m, 2H), 2.79-2.84 (m, 2H), 3.56 (s, 4H), 5.59 (d, J = 1.6 Hz, 1H), 7.00-7.11 (m, 4H), 7.36 (t, J = 7.9 Hz, 1H), 7.51 (d, J = 1.6 Hz, 1H), 7.76 (td, J = 7.9, 1.5 hz, 1H), 7.95 (d, J = 7.9 Hz, 1H), 8.09 (dd, J = 7.9, 1.5 Hz, 1H), 11.67 (s, 1H). |
|---|---|
| 2-(4-Dimethylaminopiperidin-1-ylmethyl)pyrrolo[1,2-a]quinazolin-5(4H)-one (Compound 2-22) 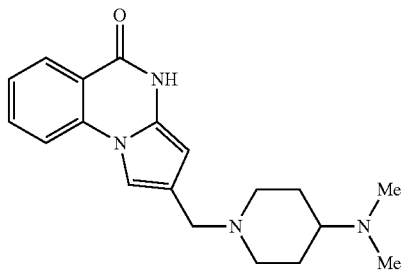 | $^1$H-NMR (400 MHz, CD$_3$OD) δ 1.55-1.66 (m, 2H), 1.90-1.97 (m, 2H), 2.10-2.18 (m, 2H), 2.40 (s, 6H), 2.41-2.47 (m, 1H), 3.09-3.15 (m, 2H), 3.56 (s, 2H), 5.77 (d, J = 1.7 Hz, 1H), 7.35-7.39 (m, 2H), 7.75-7.82 (m, 2H), 8.19 (d, J = 8.0 Hz, 1H). |

TABLE 44

| 2-[4-(Pyridin-4-yl)piperazin-1-ylmethyl]pyrrolo[1,2-a]quinazolin-5(4H)-one (Compound 2-23) 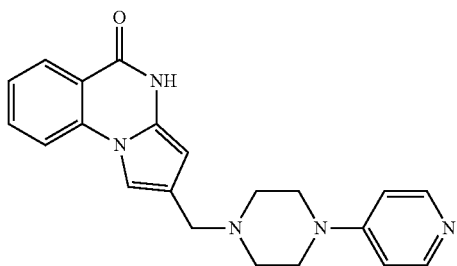 | $^1$H-NMR (400 MHz, CD$_3$OD) δ 2.63-2.69 (m, 4H), 3.40-3.47 (m, 4H), 3.57 (s, 2H), 5.80 (d, J = 1.7 Hz, 1H), 6.84 (dd, J = 5.2, 1.6 Hz, 2H), 7.38 (td, J = 7.7, 1.5 Hz, 1H), 7.40 (d, J = 1.7 Hz, 1H), 7.77 (td, J = 7.7, 1.5 Hz, 1H), 7.82 (dd, J = 7.7, 1.5 Hz, 1H), 8.10 (dd, J = 5.2, 1.6 Hz, 2H), 8.20 (dd, J = 7.7, 1.5 Hz, 1H). |
|---|---|
| 2-[4-(4-Fluorophenyl)-2-methylpiperazin-1-ylmethyl]pyrrolo[1,2-a]quinazolin-5(4H)-one (Compound 2-24) 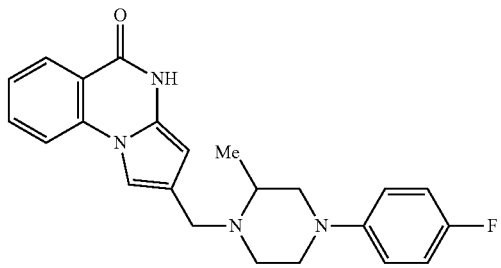 | $^1$H-NMR (400 MHz, DMSO-d$_6$) δ 1.17 (d, J = 5.6 Hz, 3H), 2.26-2.35 (m, 1H), 2.40-2.50 (m, 2H), 2.68-2.76 (m, 1H), 2.80-2.90 (m, 1H), 3.30-3.43 (m, 3H), 3.82 (d, J = 13.7 Hz, 1H), 5.56 (d, J = 1.7 Hz, 1H), 6.89-6.94 (m, 2H), 6.96-7.06 (m, 2H), 7.34-7.40 (m, 1H), 7.48 (d, J = 1.7 Hz, 1H), 7.75-7.81 (m, 1H), 7.96 (d, J = 8.3 Hz, 1H), 8.10-8.15 (dd, J = 8.0, 1.5 Hz, 1H), 11.68 (s, 1H). |

TABLE 44-continued

| | |
|---|---|
| 2-[4-(2-Methoxyphenyl)piperazin-1-ylmethyl]pyrrolo[1,2-a]quinazolin-5(4H)-one (Compound 2-25)<br>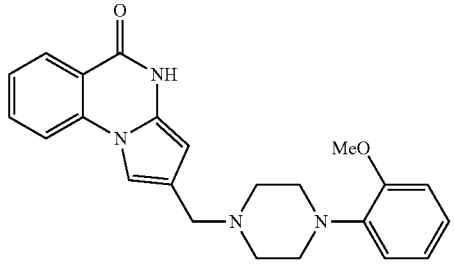 | $^1$H-NMR (400 MHz, DMSO-d$_6$) δ 2.51-2.57 (m, 4H), 2.93-2.99 (m, 4H), 3.44 (s, 2H), 3.76 (s, 3H), 5.57 (d, J = 1.7 Hz, 1H), 6.84-6.95 (m, 4H), 7.36 (t, J = 7.9 Hz, 1H), 7.48 (d, J = 1.7 Hz, 1H), 7.77 (td, J = 7.9, 1.6 Hz, 1H), 7.95 (d, J = 7.9 Hz, 1H), 8.09 (dd, J = 7.9, 1.6 Hz, 1H), 11.67 (s, 1H). |

TABLE 45

| | |
|---|---|
| 2-[4-(3-Methoxyphenyl)piperazin-1-ylmethyl]pyrrolo[1,2-a]quinazolin-5(4H)-one (Compound 2-26)<br>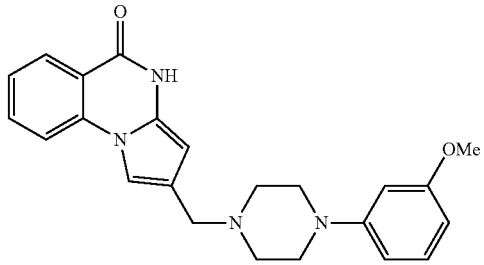 | $^1$H-NMR (400 MHz, DMSO-d$_6$) δ 2.51-2.54 (m, 4H), 3.10-3.15 (m, 4H), 3.43 (s, 2H), 3.70 (s, 3H), 5.57 (d, J = 1.6 Hz, 1H), 6.35 (dd, J = 8.2 2.2 Hz, 1H), 6.42 (t, J = 2.2 Hz, 1H), 6.51 (dd, J = 8.2, 2.2 Hz, 1H), 7.09 (t, J = 8.2 Hz, 1H), 7.36 (t, J = 7.9 Hz, 1H), 7.49 (d, J = 1.6 Hz, 1H), 7.77 (td, J = 7.9, 1.5 Hz, 1H), 7.95 (d, J = 7.9 Hz, 1H), 8.09 (dd, J = 7.9, 1.5 Hz, 1H), 11.67 (s, 1H). |
| 2-(4-Cyclohexylpiperazin-1-ylmethyl)pyrrolo[1,2-a]quinazolin-5(4H)-one (Compound 2-27)<br>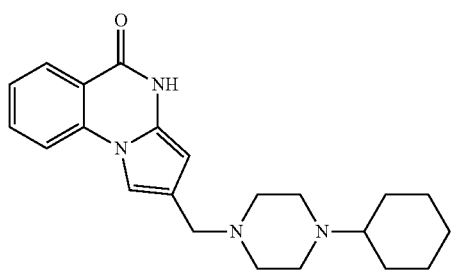 | $^1$H-NMR (400 MHz, DMSO-d$_6$) δ 1.00-1.25 (m, 5H), 1.50-1.60 (m, 1H), 1.65-1.80 (m, 4H), 2.10-2.35 (m, 1H), 2.20-2.50 (m, 10H), 5.52 (d, J = 1.7 Hz, 1H), 7.33-7.38 (m, 1H), 7.43 (d, J = 1.7 Hz, 1H), 7.72-7.80 (m, 1H), 7.93 (d, J = 8.3 Hz, 1H), 8.08 (dd, J = 7.8, 1.5 Hz, 1H), 11.65 (s, 1H). |
| 2-(4-Cyclopropylmethylpiperazin-1-ylmethyl)pyrrolo[1,2-a]quinazolin-5(4H)-one (Compound 2-28)<br>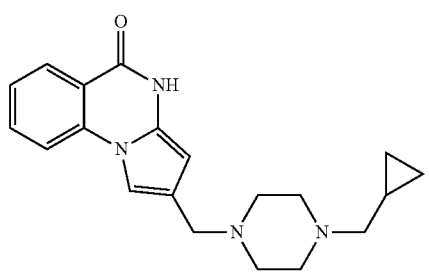 | $^1$H-NMR (400 MHz, DMSO-d$_6$) δ 0.01-0.60 (m, 2H), 0.40-0.46 (m, 2H), 0.75-0.85 (m, 1H), 2.14 (d, J = 6.3 Hz, 2H), 2.20-2.60 (m, 10H), 5.53 (d, J = 1.5 Hz, 1H), 7.30-7.40 (m, 1H), 7.43 (d, J = 1.5 Hz, 1H), 7.73-7.78 (m, 1H), 7.93 (d, J = 8.3 Hz, 1H), 8.09 (dd, J = 7.8, 1.5 Hz, 1H), 1.66 (s, 1H). |

TABLE 46

| Compound | ¹H-NMR |
|---|---|
| 2-[4-(4-Trifluoromethylphenyl)piperazin-1-ylmthyl]pyrrolo[1,2-a]quinazolin-5(4H)-one (Compound 2-29) | ¹H-NMR (400 MHz, DMSO-d₆) δ 2.52-2.56 (m, 4H), 3.25-3.30 (m, 4H), 3.44 (s, 2H), 5.58 (d, J = 1.7 Hz, 1H), 7.05 (d, J = 8.8 Hz, 2H), 7.36 (t, J = 8.0 Hz, 1H), 7.49 (d, J = 8.8 Hz, 2H), 7.50 (d, J = 1.7 Hz, 1H), 7.77 (td, J = 8.0, 1.5 Hz, 1H), 7.95 (d, J = 8.0 Hz, 1H), 8.09 (dd, J = 8.0, 1.5 Hz, 1H), 11.68 (s, 1H). |
| 2-[4-(5-Chloropyridin-2-yl)piperazin-1-ylmethyl]pyrrolo[1,2-a]quinazolin-5(4H)-one (Compound 2-39) | ¹H-NMR (500 MHz, DMSO-d₆) δ 2.44-2.49 (m, 4H), 3.43 (s, 2H), 3.45-3.50 (m, 4H), 5.57 (s, 1H), 6.85 (d, J = 9.2 Hz, 1H), 7.36 (t, J = 7.6 Hz, 1H), 7.49 (s, 1H), 7.58 (dd, J = 9.2, 2.27 Hz, 1H), 7.77 (td, J = 7.6, 1.7 Hz, 1H), 7.95 (d, J = 7.6 Hz, 1H), 8.09 (dd, J = 7.6, 1.7 Hz, 1H), 8.09 (d, J = 2.7 Hz, 1H), 11.69 (s, 1H). |
| 2-(3-Phenylpiperidin-1-ylmethyl)pyrrolo[1,2-a]quinazolin-5(4H)-one (Compound 2-31) | ¹H-NMR (400 MHz, DMSO-d₆) δ 1.36-1.47 (m, 1H), 1.54-1.65 (m, 1H), 1.67-1.75 (m, 1H), 1.77-1.84 (m, 1H), 1.96 (t, J = 11.5 Hz, 2H) 2.69-2.77 (m, 1H), 2.87-2.95 (m, 2H), 3.38 (d, J = 13.4 Hz, 1H), 3.43 (d, J = 13.4 Hz, 1H), 5.54 (d, J = 1.7 Hz, 1H), 7.15-7.20 (m, 4H), 7.21-7.29 (m, 1H), 7.34 (t, J = 7.8 Hz, 1H), 7.43 (d, J = 1.7 Hz, 1H), 7.74 (td, J = 7.8, 1.5 Hz, 1H), 7.92 (d, J = 7.8 Hz, 1H), 8.08 (dd, J = 7.8, 1.5 Hz, 1H), 11.64 (s, 1H). |

TABLE 47

| Compound | ¹H-NMR |
|---|---|
| 2-[4-(3-Methylphenyl)piperazin-1-ylmethyl]pyrrolo[1,2-a]quinazolin-5(4H)-one (Compound 2-32) | ¹H-NMR (400 MHz, DMSO-d₆) δ 2.23 (s, 3H), 2.51-2.57 (m, 4H), 3.07-3.16 (m, 4H), 3.43 (s, 2H), 5.58 (s, 1H), 6.58 (d, J = 7.6 Hz, 1H), 6.66-6.76 (m, 2H), 7.07 (t, J = 7.6 Hz, 1H), 7.36 (t, J = 7.9 Hz, 1H), 7.48 (s, 1H), 7.73-7.81 (m, 1H), 7.95 (d, J = 7.9 Hz, 1H), 8.09 (dd, J = 7.9, 1.3 Hz, 1H), 11.68 (s, 1H). |

TABLE 47-continued

| Compound | 1H-NMR |
|---|---|
| 2-[4-(Piperidin-1-yl)piperidin-1-ylmethyl]pyrrolo[1,2-a]quinazolin-5(4H)-one (Compound 2-33) | $^1$H-NMR (400 MHz, DMSO-d$_6$) δ 1.25-1.52 (m, 6H), 1.58-1.71 (m, 2H), 1.78-1.93 (m, 2H), 2.07-2.20 (m, 1H), 2.36-2.46 (m, 4H), 2.83-2.96 (m, 2H), 3.27-3.39 (m, 4H), 5.52 (d, J = 1.6 Hz, 1H), 7.35 (t, J = 7.8 Hz, 1H), 7.42 (d, J = 1.6 Hz, 1H), 7.76 (td, J = 7.8, 1.3 Hz, 1H), 7.93 (d, J = 7.8 Hz, 1H), 8.08 (dd, J = 7.8, 1.3 Hz, 1H), 11.65 (s, 1H). |
| 2-(Pyrrolidin-1-ylmethyl)pyrrolo[1,2-a]quinazolin-5(4H)-one (Compound 2-34) | $^1$H-NMR (400 MHz, DMSO-d$_6$) δ 1.65-1.80 (m, 4H), 2.40-2.75 (m, 4H), 3.50-3.70 (m, 2H), 5.61 (s, 1H), 7.30-7.40 (m, 1H), 7.49 (s, 1H), 7.74-7.82 (m, 1H), 7.93 (d, J = 7.9 Hz, 1H), 8.09 (dd, J = 7.9, 1.5 Hz, 1H), 11.70 (s, 1H). |

TABLE 48

| Compound | 1H-NMR |
|---|---|
| 2-[4-(2,4-Difluorophenyl)piperazin-1-ylmethyl]pyrrolo[1,2-a]quinazolin-5(4H)-one (Compound 2-35) | $^1$H-NMR (400 MHz, DMSO-d$_6$) δ 2.53-2.59 (m, 4H), 2.93-3.00 (m, 4H), 3.44 (s, 2H), 5.57 (d, J = 1.6 Hz, 1H), 6.95-7.09 (m, 2H), 7.15-7.21 (m, 1H), 7.36 (t, J = 8.0 Hz, 1H), 7.49 (d, J = 1.6 Hz, 1H), 7.77 (td, J = 8.0, 1.5 Hz, 1H), 7.95 (d, J = 8.0 Hz, 1H), 8.09 (dd, J = 8.0, 1.5 Hz, 1H), 11.68 (s, 1H). |
| 2-[4-(Furo[3,2-c]pyridin-4-yl)piperazin-1-ylmethyl]pyrrolo[1,2-a]quinazolin-5(4H)-one (Compound 2-36) | $^1$H-NMR (400 MHz, DMSO-d$_6$) δ 2.53-2.58 (m, 4H), 3.45 (s, 2H), 3.62-3.67 (m, 4H), 5.59 (d, J = 1.6 Hz, 1H), 7.02 (dd, J = 5.8, 0.9 Hz, 1H), 7.15 (dd, J = 2.2, 0.9 Hz, 1H), 7.36 (t, J = 7.8 Hz, 1H), 7.50 (d, J = 1.6 Hz, 1H), 7.77 (td, J = 7.8, 1.5 Hz, 1H), 7.93 (d, J = 2.2 Hz, 1H), 7.95 (d, J = 7.8 Hz, 1H), 7.96 (d, J = 5.8 Hz, 1H), 8.10 (dd, J = 7.8, 1.5 Hz, 1H), 11.69 (s, 1H). |

TABLE 48-continued

| | |
|---|---|
| 2-[4-(1H-Indol-4-yl)piperazin-1-ylmethyl]pyrrolo[1,2-a]quinazolin-5(4H)-one (Compound 2-37) 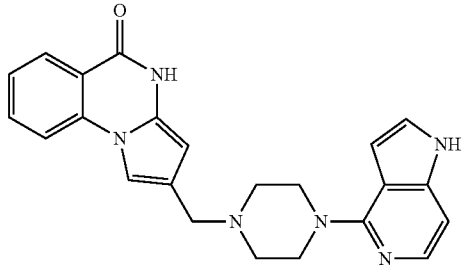 | $^1$H-NMR (400 MHz, DMSO-$d_6$) δ 2.61-2.73 (m, 4H), 3.08-3.20 (m, 4H), 3.51 (s, 2H), 5.61 (s, 1H), 6.35-6.37 (m, 1H), 6.44 (d, J = 7.1 Hz, 1H), 6.92-7.03 (m, 2H), 7.21-7.23 (m, 1H), 7.36 (t, J = 7.8 Hz, 1H), 7.52 (s, 1H), 7.78 (t, J = 7.8 Hz, 1H), 7.96 (d, J = 7.8 Hz, 1H), 8.10 (d, J = 7.8 Hz, 1H), 11.01 (s, 1H), 11.69 (s, 1H). |

TABLE 49

| | |
|---|---|
| 2-[4-(4-Isopropoxyphenyl)piperazin-1-ylmethyl]pyrrolo[1,2-a]quinazolin-5(4H)-one (Compound 2-38) 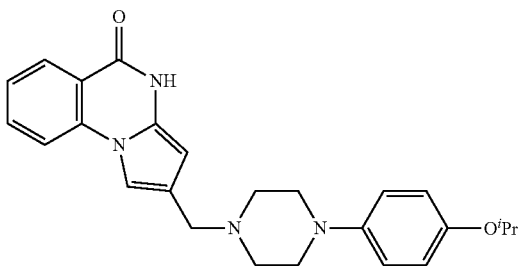 | $^1$H-NMR (400 MHz, DMSO-$d_6$) δ 1.21 (d, J = 6.1 Hz, 6H), 2.45-2.59 (m, 4H), 2.94-3.08 (m, 4H), 3.44 (s, 2H), 4.37-4.49 (m, 1H), 5.58 (s, 1H), 6.78 (d, J = 9.1 Hz, 2H), 6.85 (d, J = 9.1 Hz, 2H), 7.36 (t, J = 7.7 Hz, 1H), 7.49 (s, 1H), 7.77 (t, J = 7.7 Hz, 1H), 7.95 (d, J = 7.7 Hz, 1H), 8.09 (d, J = 7.7 Hz, 1H), 11.68 (s, 1H). |
| 2-[4-(4-Fluoro-2-methoxyphenyl)piperazin-1-ylmethyl]pyrrolo[1,2-a]quinazolin-5(4H)-one (Compound 2-39) 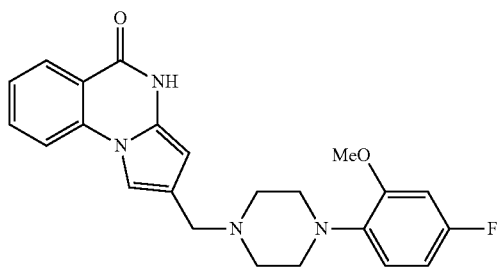 | $^1$H-NMR (500 MHz, DMSO-$d_6$) δ 2.40-2.60 (m, 4H), 2.80-3.00 (m, 4H), 3.43 (s, 2H), 3.77 (s, 3H), 5.56 (d, J = 1.5 Hz, 1H), 6.66 (td, J = 8.6, 2.7 Hz, 1H), 6.80-6.90 (m, 2H), 7.34-7.38 (m, 1H), 7.48 (d, J = 1.5 Hz, 1H), 7.75-8.00 (m, 1H), 7.95 (d, J = 8.2 Hz, 1H), 8.08 (dd, J = 7.9, 1.5 Hz, 1H), 11.68 (s, 1H). |
| 2-[4-(1,3-Benzodioxol-5-yl)piperazin-1-ylmethyl]pyrrolo[1,2-a]quinazolin-5(4H)-one (Compound 2-40) 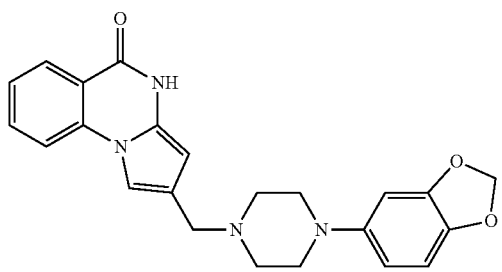 | $^1$H-NMR (500 MHz, DMSO-$d_6$) δ 2.40-2.55 (m, 4H), 2.97-3.05 (m, 4H), 3.42 (s, 2H), 5.56 (d, J = 1.7 Hz, 1H), 5.90 (s, 2H), 6.32 (dd, J = 8.3, 2.4 Hz, 1H), 6.65 (d, J = 2.4 Hz, 1H), 6.75 (d, J = 8.3 Hz, 1H), 7.36 (dd, J = 7.8, 7.3 Hz, 1H), 7.48 (d, J = 1.7 Hz, 1H), 7.74-7.80 (m, 1H), 7.95 (d, J = 8.3 Hz, 1H), 8.09 (dd, J = 7.8, 1.5 Hz, 1H), 11.68 (s, 1H). |

TABLE 50

| | |
|---|---|
| 7-[4-(4-Fluorophenyl)piperazin-1-ylmethyl]pyrrolo[1,2-a]thieno[2,3-e]pyrimidin-4(5H)-one (Compound 2-41) | $^1$H-NMR (400 MHz, DMSO-d$_6$) δ 2.40-2.60 (m, 4H), 3.00-3.13 (m, 4H), 3.44 (s, 2H), 5.60 (d, J = 1.5 Hz, 1H), 5.90-5.96 (m, 2H), 6.00-6.08 (m, 2H), 7.34 (d, J = 1.5 Hz, 1H), 7.73 (d, J = 5.4 Hz, 1H), 8.17 (d, J = 5.4 Hz, 1H), 11.71 (s, 1H). |
| 7-[4-(4-Chlorophenyl)piperazin-1-ylmethyl]pyrrolo[1,2-a]thieno[2,3-e]pyrimidin-4(5H)-one (Compound 2-42) | $^1$H-NMR (500 MHz, DMSO-d$_6$) δ 2.40-2.60 (m, 4H), 3.08-3.20 (m, 4H), 3.44 (s, 2H), 5.60 (d, J = 1.8 Hz, 1H), 6.92 (d, J = 9.2 Hz, 2H), 7.21 (d, J = 9.2 Hz, 2H), 7.34 (d, J = 1.8 Hz, 1H), 7.73 (d, J = 5.5 Hz, 1H), 8.18 (d, J = 5.5 Hz, 1H), 11.71 (s, 1H). |
| 7-(Pyrrolidin-1-ylmethyl)pyrrolo[1,2-a]thieno[2,3-e]pyrimidin-4(5H)-one (Compound 2-43) | $^1$H-NMR (500 MHz, DMSO-d$_6$) δ 1.64-1.73 (m, 4H), 2.40-2.50 (m, 4H), 3.48 (s, 2H), 5.57 (d, J = 1.5 Hz, 1H), 7.29 (d, J = 1.5 Hz, 1H), 7.72 (d, J = 5.5 Hz, 1H), 8.17 (d, J = 5.5 Hz, 1H), 11.69 (s, 1H). |

TABLE 51

| | |
|---|---|
| 7-Fluoro-2-[4-(pyridin-2-yl)piperazin-1-ylmethyl]pyrrolo[1,2-a]quinazolin-5(4H)-one (Compound 2-44) | $^1$H-NMR (400 MHz, DMSO-d$_6$) δ 2.50-2.55 (m, 4H), 3.41-3.51 (m, 4H), 3.43 (s, 2H), 5.59 (s, 1H), 6.62 (dd, J = 7.0, 5.1 Hz, 1H), 6.80 (d, J = 8.5 Hz, 1H), 7.51 (ddd, J = 8.5, 7.0, 1.5 Hz, 1H), 7.51 (s, 1H), 7.68 (td, J = 8.8, 3.30 Hz, 1H), 7.78 (dd, J = 8.8, 3.0 Hz, 1H), 8.04 (dd, J = 8.8, 4.4 Hz, 1H), 8.09 (dd, J = 5.1, 1.5 Hz, 1H), 11.84 (s, 1H). |

TABLE 51-continued

| | |
|---|---|
| 7-Fluoro-2-[4-(4-fluorophenyl)piperazin-1-ylmethyl]pyrrolo[1,2-a]quinazolin-5(4H)-one (Compound 2-45) | $^1$H-NMR (400 MHz, DMSO-$d_6$) δ 2.52-2.56 (m, 4H), 3.05-3.09 (m, 4H), 3.43 (s, 2H), 5.58 (d, J = 1.5 Hz, 1H), 6.90-6.96 (m, 2H), 7.00-7.07 (m, 2H), 7.51 (d, J = 1.5 Hz, 1H), 7.68 (td, J = 8.8, 3.1 Hz, 1H), 7.78 (dd, J = 8.8, 3.1 Hz, 1H), 8.04 (dd, J = 8.8, 4.3 Hz, 1H), 11.83 (s, 1H). |

TABLE 52

| | |
|---|---|
| 2-[4-[2-(2-Dimethylaminoethoxy)-4-fluorophenyl]piperazin-1-ylmethyl]pyrrolo[1,2-a]quinazolin-5(4H)-one (Compound 2-46) | $^1$H-NMR (500 MHz, DMSO-$d_6$) δ 2.22 (s, 6H), 2.40-2.60 (m, 4H), 2.63 (t, J = 5.5 Hz, 2H), 2.85-3.05 (m, 4H), 3.42 (s, 2H), 4.02 (t, J = 5.5 Hz, 2H), 5.57 (d, J = 1.8 Hz, 1H), 6.60-6.70 (m, 1H), 6.80-6.88 (m, 2H), 7.33-7.40 (m, 1H), 7.48 (d, J = 1.8 Hz, 1H), 7.74-7.79 (m, 1H), 7.95 (d, J = 9.2 Hz, 1H), 8.09 (dd, J = 7.9, 1.5 Hz, 1H), 1168 (s, 1H). |
| 2-[4-(Morpholin-4-yl)piperidin-1-ylmethyl]pyrrolo[1,2-a]quinazolin-5(4H)-one (Compound 2-47) | $^1$H-NMR (500 MHz, DMSO-$d_6$) δ 1.50-1.61 (m, 2H), 1.89-1.95 (m, 2H), 2.03-2.11 (m, 2H), 2.15-2.24 (m, 1H), 2.54-2.59 (m, 4H), 3.04-3.10 (m, 2H), 3.51 (s, 2H), 3.66-3.71 (m, 4H), 4.32 (s, 1H), 5.77 (d, J = 2.0 Hz, 1H), 7.35-7.39 (m, 2H), 7.74-7.83 (m, 2H), 8.19 (dd, J = 7.9, 0.9 Hz, 1H). |

Example 3

2-[4-(4-Hydroxyphenyl)piperazin-1-ylmethyl]pyrrolo[1,2-a]quinazolin-5(4H)-one (Compound 3-1)

Under cooling on ice, boron tribromide (0.100 mL, 1.04 mmol) was added to a solution of 2-[4-(4-methoxyphenyl)piperazin-1-ylmethyl]pyrrolo[1,2-a]quinazolin-5(4H)-one (the above Compound 2-16, 200 mg, 0.515 mmol) in methylene chloride (3.0 mL). The reaction solution was stirred at room temperature for 1 hour. The reaction solution was diluted with methanol (2.0 mL) under cooling on ice, and then concentrated under reduced pressure. The obtained residue was dissolved in 1M sodium hydroxide aqueous solution (2.0 mL), and 2M hydrochloric acid was added so that pH of the solution was 7. The precipitate was collected by filtration, and dried under reduced pressure, to obtain title Compound 3-1 (43.2 mg, yield: 22%) as an orange powder.

TABLE 53

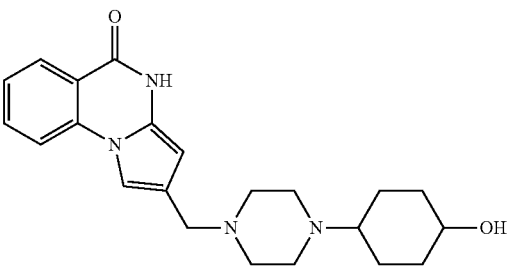 [SMILES: O=c1[nH]c2cc(CN3CCN(C4CCC(O)CC4)CC3)cn2c2ccccc12]

¹H-NMR (400 MHz, DMSO-d₆) δ 2.52-2.56 (m, 4H), 2.93-2.98 (m, 4H), 3.43 (s, 2H), 5.57 (s, 1H), 6.63 (d, J = 9.0 Hz, 2H), 6.76 (d, J = 9.0 Hz, 2H), 7.36 (t, J = 7.8 Hz, 1H), 7.48 (s, 1H), 7.77 (td, J = 7.8, 1.5 Hz, 1H), 7.95 (d, J = 7.8 Hz, 1H), 8.09 (dd, J = 7.8, 1.5 Hz, 1H), 8.78 (s, 1H), 11.67 (s, 1H).

Example 4

2-[1-[4-(4-Fluorophenyl)piperazin-1-yl]-1,1-dideuteriomethyl]pyrrolo[1,2-a]quinazolin-5(4H)-one (Compound 4-1)

Under cooling on ice, lithium aluminum deuteride (66.4 mg, 1.42 mmol) was added to a solution of 2-[4-(4-fluorophenyl)piperazine-1-carbonyl]pyrrolo[1,2-a]quinazolin-5(4H)-one (the above Compound 1-1, 278 mg, 0.712 mmol) in anhydrous tetrahydrofuran (6 mL). The reaction solution was stirred at room temperature for 2 hours. To the reaction solution, a small amount of ethyl acetate was added dropwise, and then a saturated aqueous solution of sodium potassium tartrate tetrahydrate (3 mL) and water (20 mL) were added sequentially. The mixture was extracted twice with chloroform (40 mL). The organic layer was dried over anhydrous magnesium sulfate, and then the solvent was distilled off under reduced pressure. The obtained residue was collected by filtration with ethanol, to obtain the title compound (174 mg, yield: 65%) as a pale yellow powder.

TABLE 54

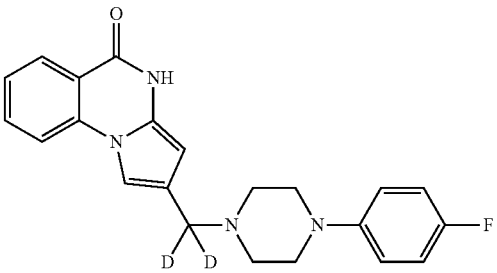 [SMILES: [2H]C([2H])(c1cc2[nH]c(=O)c3ccccc3n2c1)N1CCN(c2ccc(F)cc2)CC1]

¹H-NMR (400 MHz, DMSO-d₆) δ 2.30-2.60 (m, 4H), 3.00-3.16 (m, 4H), 5.57 (d, J = 1.7 Hz, 1H), 6.90-6.97 (m, 2H), 6.99-7.07 (m, 2H), 7.36 (t, J = 7.3 Hz, 1H), 7.48 (d, J = 1.7 Hz, 1H), 7.77 (td, J = 7.3, 1.5 Hz, 1H), 7.95 (d, J = 7.3 Hz, 1H), 8.09 (dd, J = 7.3, 1.5 Hz, 1H), 11.67 (s, 1H).

Example 5

2-(Homopiperazine-1-carbonyl)pyrrolo[1,2-a]quinazolin-5(4H)-one hydrochloride (Compound 5-1)

10% hydrogen chloride in methanol (3 mL) was added to a solution of 2-[4-(tert-butoxycarbonyl)homopiperazine-1-carbonyl]pyrrolo[1,2-a]quinazolin-5(4H)-one (the above Compound 1-47, 156 mg, 0.380 mmol) in methanol (1 mL), and the reaction solution was stirred overnight at room temperature. The precipitated solid was collected by filtration, and dried under reduced pressure, to obtain the title compound (102 mg, yield: 87%) as a colorless powder.

TABLE 55

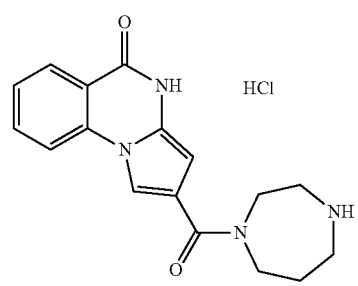 [SMILES: O=C(c1cc2[nH]c(=O)c3ccccc3n2c1)N1CCCNCC1 ; Cl]

¹H-NMR (400 MHz, DMSO-d₆) δ 2.05-2.15 (m, 2H), 3.21 (t, J = 5.5 Hz, 2H), 3.28 (t, J = 5.2 Hz, 2H), 3.80 (t, J = 6.1 Hz, 2H), 3.91 (t, J = 5.2 Hz, 2H), 5.84 (d, J = 1.8 Hz, 1H), 7.42-7.46 (m, 1H), 7.76-7.82 (m, 1H), 7.82 (d, J = 1.8 Hz, 1H), 8.03 (d, J = 7.9 Hz, 1H), 8.16 (dd, J = 7.9, 1.2 Hz, 1H), 9.17 (s, 2H), 11.51 (s, 1H).

In the following, by using Compound 1-48, Compound 5-2 was obtained according to the production method for Compound 5-1.

TABLE 56

2-(Piperazine-1-carbonyl)pyrrolo[1,2-a]quinazolin-5(4H)-one (Compound 5-2)

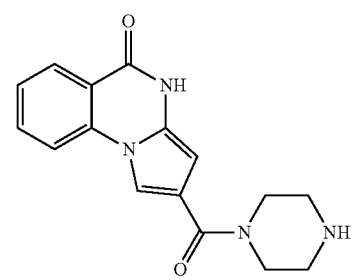

¹H-NMR (500 MHz, DMSO-d₆) δ 2.65-2.80 (m, 4H), 3.50-3.75 (m, 4H), 5.71 (d, J = 1.8 Hz, 1H), 7.40-7.50 (m, 1H), 7.75-7.85 (m, 1H), 7.90 (d, J = 1.8 Hz, 1H), 8.10-8.14 (m, 2H), 12.00 (s, 1H).

Example 6

2-[4-Cyclopropylcarbonylhomopiperazine-1-carbonyl]pyrrolo[1,2-a]quinazolin-5(4H)-one (Compound 6-1)

Diisopropylethylamine (0.11 mL, 0.63 mmol) and cyclopropane carbonyl chloride (30 μL, 0.33 mmol) were sequentially added to a solution of 2-(homopiperazine-1-carbonyl)pyrrolo[1,2-a]quinazolin-5(4H)-one hydrochloride (Compound 5-1, 70.0 mg, 0.20 mmol) in anhydrous N,N-dimethylformamide (0.50 mL), and the reaction solution was stirred overnight at room temperature. The reaction solution was diluted with ethyl acetate (20 mL), and washed sequentially with 0.1 M sodium hydroxide aqueous solution (20 mL) and brine (20 mL). The aqueous layer was extracted twice with chloroform (20 mL), and combined with the ethyl acetate layer, and dried over anhydrous magnesium sulfate. After concentration under reduced pressure, the obtained residue was purified by silica gel column chromatography (ethyl acetate), to obtain the title compound (25.8 mg, yield: 34%) as a colorless powder.

TABLE 57

$^1$H-NMR (500 MHz, DMSO-$d_6$, 100° C.) δ 0.60-0.80 (m, 4H), 1.70-2.00 (m, 3H), 3.50-4.00 (m, 8H), 5.78 (d, J = 1.8 Hz, 1H), 7.40-7.45 (m, 1H), 7.76 (d, J = 1.8 Hz, 1H), 7.77-7.83 (m, 1H), 8.01 (d, J = 8.2 Hz, 1H), 8.15 (dd, J = 7.9, 1.5 Hz, 1H), 11.46 (s, 1H).

Formulation Examples

In the following, typical formulation examples containing the present compound are shown.

1) Tablet (in 150 mg)

| | |
|---|---|
| Present compound | 1 mg |
| Lactose | 100 mg |
| Corn starch | 40 mg |
| Carboxymethylcellulose calcium | 4.5 mg |
| Hydroxypropylcellulose | 4 mg |
| Magnesium stearate | 0.5 mg |

By coating the tablet of the above formulation with 3 mg of a coating agent (ordinary coating agents such as hydroxypropylmethylcellulose, macrogol, silicone resin and the like), an intended tablet can be obtained. Also by appropriately changing the kind and/or the amount of the present compound and additives, a desired tablet can be obtained.

2) Capsule (in 150 mg)

| | |
|---|---|
| Present compound | 5 mg |
| Lactose | 135 mg |
| Carboxymethylcellulose calcium | 4.5 mg |
| Hydroxypropylcellulose | 4 mg |
| Magnesium stearate | 1.5 mg |

By appropriately changing the kind and/or the amount of the present compound and additives, a desired capsule can be obtained.

3) Ophthalmic Solution (in 100 mL)

| | |
|---|---|
| Present compound | 100 mg |
| Sodium chloride | 900 mg |
| Polysorbate 80 | 500 mg |
| Sodium hydroxide | q.s. |
| Hydrochloric acid | q.s. |
| Sterile purified water | q.s. |

By appropriately changing the kind and/or the amount of the present compound and additives, a desired ophthalmic solution can be obtained.

[Pharmacological Test]

1. PARP Inhibitory Activity Measurement Test

For evaluating PARP inhibitory activity of the present compound, inhibitory activity of each test compound against human recombinant PARP 1 was measured using Universal Colorimetric PARP Assay kit with Histone-Coated Strip Wells (Cat No.: 4677-096-K) available from Trevigen. The test was conducted according to the procedure in the instruction attached to this kit. The concrete operation will be described below.

(Preparation of Test Compound Solution)

After dissolving the test compound in dimethyl sulfoxide, the solution was diluted with a PARP buffer attached to the kit to prepare a 50 μM test compound solution.

(Test Method and Measurement Method)

In each well of a histone-coated 96-well plate, 10 μL of the test compound solution (50 μM), 15 μL of human recombinant PARP1 (33.3 Unit/mL) and 25 μL of PARP cocktail (containing activated DNA and biotinated NAD) were added, and incubated at room temperature for 1 hour (final reaction amount: 50 μL). Each well was washed twice with 200 μL of 0.1% Triton-X-containing Dulbecco's phosphate buffer, and further washed twice with 200 μL of Dulbecco's phosphate buffer, and then 50 μL of Strep-HRP was added, followed by incubation at room temperature for 1 hour. Each well was washed twice with 200 μL of 0.1% Triton-X-containing Dulbecco's phosphate buffer, and further washed twice with 200 μL of Dulbecco's phosphate buffer, and then 50 μL of TACS-Sapphire coloriometric substrate was added, followed by incubation at room temperature for 15 minutes. After stopping the reaction by adding 50 μL of 0.2 M HCl, absorbance at 450 nm (Abs 450) was measured by a microplate reader. The number of examples in each group was 1 to 2.

(Negative Control)

Using a well into which dimethyl sulfoxide and a PARP buffer were added in place of the test compound solution and human recombinant PARP1, the above operation was conducted as a negative control.

(Positive Control)

Using a well into which a PARP buffer containing dimethyl sulfoxide was added in place of the test compound solution, the above operation was conducted as a positive control.

(Calculation of PARP1 Inhibition Rate)

PARP1 inhibition rate (%) was calculated according to the following Formula 1.

$$\text{PARP1 inhibition rate}(\%) = (Abs_B - Abs_X)/(Abs_B - Abs_A) \times 100 \quad \text{[Formula 1]}$$

$Abs_A$: absorbance of negative control (Abs 450)
$Abs_B$: absorbance of positive control (Abs 450)
$Abs_X$: absorbance of test compound-treated group (Abs 450)

(Result)

PARP inhibition rate of each test compound (compound concentration: 10 μM) is shown in the following Tables 58 and 59.

TABLE 58

| Compound | Inhibition rate (%) |
|---|---|
| 1-1 | 90 |
| 1-2 | 55 |
| 1-3 | 100 |
| 1-4 | 99 |
| 1-5 | 71 |
| 1-6 | 23 |
| 1-7 | 44 |
| 1-8 | 51 |
| 1-10 | 68 |
| 1-11 | 86 |
| 1-12 | 64 |
| 1-13 | 67 |
| 1-14 | 44 |
| 1-15 | 74 |
| 1-21 | 84 |
| 1-47 | 93 |
| 1-49 | 36 |
| 1-50 | 92 |
| 1-51 | 92 |
| 1-52 | 94 |
| 1-53 | 96 |
| 1-54 | 81 |
| 1-55 | 81 |
| 1-56 | 83 |
| 2-1 | 100 |
| 2-2 | 78 |
| 2-3 | 99 |
| 2-4 | 100 |
| 2-5 | 96 |
| 2-6 | 100 |
| 2-7 | 99 |
| 2-8 | 100 |
| 2-9 | 99 |
| 2-10 | 98 |
| 2-11 | 99 |
| 2-12 | 100 |
| 2-13 | 96 |
| 2-14 | 100 |

TABLE 59

| Compound | Inhibition rate (%) |
|---|---|
| 2-15 | 98 |
| 2-16 | 100 |
| 2-17 | 100 |
| 2-18 | 95 |
| 2-19 | 93 |
| 2-20 | 90 |
| 2-21 | 65 |
| 2-22 | 97 |
| 2-23 | 100 |
| 2-24 | 99 |
| 2-25 | 100 |
| 2-26 | 78 |
| 2-27 | 99 |
| 2-28 | 99 |
| 2-29 | 40 |
| 2-30 | 100 |
| 2-31 | 66 |
| 2-32 | 97 |
| 2-33 | 96 |
| 2-34 | 96 |
| 2-35 | 100 |
| 2-36 | 82 |
| 2-37 | 71 |
| 2-38 | 98 |
| 2-39 | 100 |
| 2-40 | 100 |
| 2-41 | 100 |
| 2-42 | 100 |
| 2-43 | 91 |
| 2-44 | 98 |
| 2-45 | 100 |
| 2-46 | 85 |
| 2-47 | 99 |
| 3-1 | 100 |
| 4-1 | 100 |
| 5-1 | 99 |
| 5-2 | 85 |
| 6-1 | 90 |

(Discussion)

As is apparent from Tables 58 and 59, it was demonstrated that the present compound has strong PARP inhibitory activity.

2. Evaluation Test of Retinal Degeneration Inhibitory Activity in Rat MNU-Induced Model For examining influence of the present compound on the retinal degeneration, retinal degeneration inhibitory activity of test compound was evaluated, using a rat N-methyl-N-nitrosourea (hereinafter, "MNU")-induced retinal degeneration model. The rat MNU-induced retinal degeneration model is a model animal in which cell death of retinal photoreceptor cell is induced by administration of MNU which is a DNA alkylation agent, and is generally used as a model animal for chorioretinal degenerative diseases such as retinitis pigmentosa (Exp. Eye. Res., 84(2), 285-292 (2007)).

(Test Method and Measurement Method)

By the previous day of MNU administration, retinal volumes of 8-week-old Brown Norway male rats were measured by using optical coherence tomography (OCT) (product of Carl Zeiss, model number: STRATUS OCT Model 3000). An MNU administration liquid was intraperitoneally administered to the rats at a dose of 50 to 60 mg/kg, and on the seventh day after administration, retinal volumes were measured by using OCT. The normal control group underwent no treatment, and retinal volumes were measured on the same day as the MNU administration group. The number of examples in each group was 4 rats (8 eyes).

(Administration Method)

Test compound-administered group: A solution of each test compound suspended in 1% (w/v) methylcellulose aqueous solution was orally administered once 30 minutes before MNU administration at a dose of 1 to 30 mg/kg.

Normal control group and vehicle-administered group: 1% (w/v) methylcellulose aqueous solution was orally administered once 30 minutes before MNU administration.

(Calculation of Retinal Volume Reduction Inhibition Rate)

According to the following Formula 2, retinal volume reduction inhibition rate (%) was calculated.

$$\text{Retinal volume reduction inhibition rate}(\%) = (RV_{X\text{-}pre}/RV_{X\text{-}post} - RV_{B\text{-}pre}/RV_{B\text{-}post})/(RV_{A\text{-}pre}/RV_{A\text{-}post} - RV_{B\text{-}pre}/RV_{B\text{-}post}) \times 100 \quad \text{[Formula 2]}$$

$RV_{A\text{-}pre}$: retinal volume before MNU administration of normal control group (mm$^3$)

$RV_{A\text{-}post}$: retinal volume on the seventh day after MNU administration of normal control group (mm$^3$)

$RV_{B\text{-}pre}$: retinal volume before MNU administration of vehicle-administered group (mm$^3$)

$RV_{B\text{-}post}$: retinal volume on the seventh day after MNU administration of vehicle-administered group (mm$^3$)

$RV_{X\text{-}pre}$: retinal volume before MNU administration of test compound-administered group (mm$^3$)

$RV_{X\text{-}post}$: retinal volume on the seventh day after MNU administration of test compound-administered group (mm$^3$)

(Results)

Retinal volume reduction inhibition rate by each test compound (dose: 1, 10 or 30 mg/kg) is shown in Table 60.

TABLE 60

| Compound | MNU administration dose (mg/kg) | Test compound administration dose (mg/kg) | Inhibition rate (%) |
|---|---|---|---|
| 2-1 | 60 | 10 | 65 |
| 2-5 | 50 | 10 | 16 |
| 2-7 | 50 | 10 | 69 |
| 2-8 | 50 | 10 | 39 |
| 2-9 | 50 | 10 | 25 |
| 2-12 | 60 | 30 | 47 |
| 2-14 | 50 | 10 | 33 |
| 2-16 | 50 | 10 | 29 |
| 2-17 | 50 | 10 | 48 |
| 2-30 | 50 | 10 | 72 |
| 2-35 | 50 | 10 | 61 |
| 2-39 | 50 | 10 | 84 |
| 2-40 | 50 | 10 | 88 |
| 2-44 | 50 | 10 | 81 |
| 2-45 | 50 | 1 | 81 |
| 4-1 | 50 | 10 | 94 |

(Discussion)

As is apparent from Table 60, it was demonstrated that the present compound suppresses retinal volume reduction observed in rat MNU-induced model. Therefore, it is considered that the present compound has the potential to become therapeutic agents for posterior ocular diseases such as age-related macular degeneration, retinitis pigmentosa, retinal detachment, diabetic macular edema, cone dystrophy, cancer-related retinopathy, retinal vein obstruction and detachment of retinal pigment epithelium.

3. Evaluation Test of Retinal Vascular Hyperpermeability Inhibitory Activity in Rat Thrombin Model For examining the influence of the present compound on retinal vascular hyperpermeability, the retinal vascular hyperpermeability inhibitory activity of the test compound was evaluated using a rat thrombin-induced retinal vascular hyperpermeability model. The rat thrombin-induced retinal vascular hyperpermeability model is an animal in which retinal vascular permeability is increased by administration of thrombin, and is used as a model animal for diabetic retinopathy, diabetic macular edema and so on (IONS, 2000, 41(4), S18, 92).

(Test Method and Measurement Method)

A thrombin liquid preparation was intravitreally administered to 8-week old Brown Norway male rat at a dose of 3 U/eye, and the vitreous body was collected on the next day of administration, and intravitreal protein concentration was measured by the Bradford method. A normal control group received intravitreal administration of DPBS. The number of examples in each group was 4 rats (7-8 eyes).

(Administration Method)

Test compound-administered group: A solution of each test compound suspended in 1% (w/v) methylcellulose aqueous solution was orally administered in a dose of 100 mg/kg, 1.5 hours before and 22.5 hours after thrombin administration.

Normal control group and vehicle-administered group

A solution of each test compound suspended in 1% (w/v) methylcellulose aqueous solution was orally administered at a dose of mg/kg 1.5 hours before and 22.5 hours after thrombin administration.

(Calculation of Retinal Vascular Hyperpermeability Inhibition Rate)

According to the following Formula 3, retinal vascular hyperpermeability inhibition rate was calculated.

$$\text{Retinal vascular hyperpermeability inhibition rate}(\%) = (P_B - P_X)/(P_B - P_A) \times 100 \quad \text{[Formula 3]}$$

$P_A$: intravitreal protein concentration of normal control group $P_B$: intravitreal protein concentration of vehicle-administered group $P_X$: intravitreal protein concentration of test compound-administered group (Result)

Retinal vascular hyperpermeability inhibition rate of test compound is shown in Table 61.

TABLE 61

| Compound | Administration dose (mg/kg) | Inhibition rate (%) |
|---|---|---|
| 2-1 | 100 | 63 |

(Discussion)

As is apparent from Table 61, it was demonstrated that the present compound suppresses retinal vascular hyperpermeability. Therefore, it is considered that the present compound has the potential to become therapeutic agents for posterior ocular diseases such as diabetic retinopathy and diabetic macular edema accompanied by retinal vascular hyperpermeability.

INDUSTRIAL APPLICABILITY

The present compound is useful in that it has strong PARP inhibitory activity and has the potential to become therapeutic agents for various diseases including posterior ocular diseases.

The invention claimed is:
1. A compound represented by the following general formula (1) or a salt thereof;

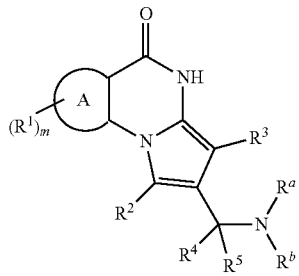

(1)

(wherein R¹ represents a halogen atom, a lower alkyl group, a hydroxy group, a lower alkoxy group, an amino group, a nitro group or a cyano group;
R² and R³ may be the same or different and each represent a hydrogen atom, a halogen atom or a lower alkyl group;
R⁴ and R⁵ may be the same or different and each represent a hydrogen atom, a deuterium atom or a lower alkyl group, or R⁴ and R⁵ may form an oxo group;
R$^a$ and R$^b$ may be the same or different and each represent a hydrogen atom, a lower alkyl group optionally having a substituent or an aryl group optionally having a substituent;
R$^a$ and R$^b$ may bind to each other to form a nitrogen-containing heterocyclic ring which may be substituted by one or plural R$^c$;
R$^c$ represents a lower alkyl group optionally having a substituent, a lower cycloalkyl group optionally having a substituent, an aryl group optionally having a substituent, a heterocyclic group optionally having a substituent, a hydroxy group, a lower alkoxy group optionally having a substituent, a lower alkylcarbonyl group optionally having a substituent, a lower cycloalkylcarbonyl group optionally having a substituent, a lower alkylaminocarbonyl group optionally having a substituent, a lower cycloalkylaminocarbonyl group optionally having a substituent, a lower alkoxycarbonyl group optionally having a substituent, an amino group, a lower alkylamino group or a carboxyl group;
ring A represents a benzene ring or an unsaturated heteromonocyclic ring; and
m represents 0, 1 or 2).

2. The compound according to claim 1 or a salt thereof, wherein in the general formula (1),
R¹ represents a halogen atom or a lower alkyl group;
R² and R³ may be the same or different and each represent a hydrogen atom, a halogen atom or a lower alkyl group;
R⁴ and R⁵ may be the same or different and each represent a hydrogen atom, a deuterium atom or a lower alkyl group, or R⁴ and R⁵ may form an oxo group;
R$^a$ and R$^b$ may be the same or different and each represent a hydrogen atom, a lower alkyl group or an aryl group, and the lower alkyl group or the aryl group may be substituted by a deuterium atom, an aryl group, a heterocyclic group, an amino group or a lower alkylamino group;
R$^a$ and R$^b$ may bind to each other to form a nitrogen-containing heterocyclic ring which may be substituted by one or plural R$^c$;
R$^c$ represents a lower alkyl group, a lower cycloalkyl group, an aryl group, a heterocyclic group, a hydroxy group, a lower alkoxy group, a lower alkylcarbonyl group, a lower cycloalkylcarbonyl group, a lower alkylaminocarbonyl group, a lower cycloalkylaminocarbonyl group, a lower alkoxycarbonyl group, an amino group, a lower alkylamino group or a carboxyl group, and the lower alkyl group, the lower cycloalkyl group, the aryl group, the heterocyclic group, the lower alkoxy group, the lower alkylcarbonyl group, the lower cycloalkylcarbonyl group, the lower alkylaminocarbonyl group, the lower cycloalkylaminocarbonyl group, the lower alkoxycarbonyl group or the lower alkylamino group may be substituted by one or plural groups selected from the group consisting of a deuterium atom, a halogen atom, a lower alkyl group, a lower alkyl group substituted by a halogen atom, a lower cycloalkyl group, an aryl group, an aryl group substituted by a halogen atom, a heterocyclic group, a hydroxy group, a lower alkoxy group and a lower alkoxy group substituted by a lower alkylamino group;
ring A represents a benzene ring or a 5-membered unsaturated heteromonocyclic ring; and
m represents 0 or 1.

3. The compound according to claim 1 or a salt thereof, wherein in the general formula (1),
R¹ represents a halogen atom or a lower alkyl group;
R² and R³ each represent a hydrogen atom;
R⁴ and R⁵ may be the same or different and each represent a hydrogen atom, a deuterium atom or a lower alkyl group, or R⁴ and R⁵ may form an oxo group;
R$^a$ and R$^b$ may be the same or different and each represent a hydrogen atom, a lower alkyl group or an aryl group, and the lower alkyl group or the aryl group may be substituted by an aryl group, a heterocyclic group, an amino group or a lower alkylamino group;
R$^a$ and R$^b$ may bind to each other to form a nitrogen-containing heteromonocyclic ring or a nitrogen-containing heterobicyclic ring which may be substituted by one or plural R$^c$;
R$^c$ represents a lower alkyl group, a lower cycloalkyl group, an aryl group, a heterocyclic group, a hydroxy group, a lower alkoxy group, a lower alkylcarbonyl group, a lower cycloalkylcarbonyl group, a lower alkylaminocarbonyl group, a lower cycloalkylaminocarbonyl group, a lower alkoxycarbonyl group, an amino group, a lower alkylamino group or a carboxyl group, and the lower alkyl group, the lower cycloalkyl group, the aryl group, the heterocyclic group, the lower alkoxy group, the lower alkylcarbonyl group, the lower cycloalkylcarbonyl group, the lower alkylaminocarbonyl group, the lower cycloalkylaminocarbonyl group, the lower alkoxycarbonyl group or the lower alkylamino group may be substituted by one or plural groups selected from the group consisting of a halogen atom, a lower alkyl group, a lower alkyl group substituted by a halogen atom, a lower cycloalkyl group, an aryl group, an aryl group substituted by a halogen atom, a hydroxy group, a lower alkoxy group and a lower alkoxy group substituted by a lower alkylamino group,
ring A represents a benzene ring or a 5-membered unsaturated heteromonocyclic ring; and
m represents 0 or 1.

4. The compound according to claim 1 or a salt thereof, wherein in the general formula (1),
R$^a$ and R$^b$ may be the same or different and each represent a hydrogen atom, a lower alkyl group or a phenyl group, and the lower alkyl group may be substituted by a phenyl group, a pyridyl group, a morphonyl group, an amino group or a dimethylamino group.

5. The compound according to claim 1 or a salt thereof, wherein in the general formula (1), $R^a$ and $R^b$ bind to each other to form a nitrogen-containing heterocyclic ring represented by the following formula (2a) or (3a);

(2a)

(3a)

in the above formula (2a),

X represents $CH_2$, $CH_2CHR^{c\beta}$, $CH=CR^{c\beta}$, $CH_2NR^{c\beta}$ or $CH_2CH_2NR^{c\beta}$;

$R^{c\alpha}$ represents a hydrogen atom, a halogen atom, a lower alkyl group or a phenyl group; and $R^{c\beta}$ represents a hydrogen atom, a lower alkyl group, a lower cycloalkyl group, an aryl group, a heteromonocyclic group, a heterobicyclic group, a lower alkoxycarbonyl group, a lower cycloalkylcarbonyl group or a lower alkylamino group, and the lower alkyl group, the lower cycloalkyl group, the aryl group, the heteromonocyclic group, the heterobicyclic group, the lower alkoxycarbonyl group or the lower cycloalkylcarbonyl group may be substituted by one or plural groups selected from the group consisting of a halogen atom, a lower alkyl group, a lower alkyl group substituted by a halogen atom, a lower cycloalkyl group, an aryl group, an aryl group substituted by a halogen atom, a hydroxy group, a lower alkoxy group and a lower alkoxy group substituted by a lower alkylamino group.

6. The compound according to claim 1 or a salt thereof, wherein in the general formula (1), $R^a$ and $R^b$ bind to each other to form a nitrogen-containing heterocyclic ring represented by the following formula (2a);

(2a)

in the above formula (2a), $R^{c\alpha}$ represents a hydrogen atom, a halogen atom, a lower alkyl group or a phenyl group;

X represents $CH_2CHR^{c\beta}$, $CH=CR^{c\beta}$ or $CH_2NR^{c\beta}$; and $R^{c\beta}$ represents a hydrogen atom, a lower alkyl group, a lower cycloalkyl group, an aryl group, a heteromonocyclic group, a heterobicyclic group, a lower alkoxycarbonyl group, a lower cycloalkylcarbonyl group or a lower alkylamino group, and the lower alkyl group, the lower cycloalkyl group, the aryl group, the heteromonocyclic group, the heterobicyclic group, the lower alkoxycarbonyl group or the lower cycloalkylcarbonyl group may be substituted by one or plural groups selected from the group consisting of a halogen atom, a lower alkyl group, a lower alkyl group substituted by a halogen atom, a lower cycloalkyl group, an aryl group, an aryl group substituted by a halogen atom, a hydroxy group, a lower alkoxy group and a lower alkoxy group substituted by a lower alkylamino group.

7. The compound according to claim 5 or a salt thereof, wherein in the above formula (2a), $R^{c\beta}$ represents a hydrogen atom, a halogen atom, a methyl group or a phenyl group; and $R^{c\beta}$ represents a hydrogen atom, a methyl group, a cyclohexyl group, a phenyl group, a pyridyl group, a piperidyl group, a thiazole group, a morphonyl group, an indolyl group, a furo[3,2-c]pyridin-4-yl group, a 1,3-benzodioxol-5-yl group, an ethoxycarbonyl group, a cyclopropylcarbonyl group or a dimethylamino group, and the methyl group, the cyclohexyl group, the phenyl group, the pyridyl group, the piperidyl group, the thiazole group, the morphonyl group, the indolyl group, the furo[3,2-c]pyridin-4-yl group or the 1,3-benzodioxol-5-yl group may be substituted by one or plural groups selected from the group consisting of a halogen atom, a lower alkyl group, a lower alkyl group substituted by a halogen atom, a lower cycloalkyl group, a phenyl group, a phenyl group substituted by a halogen atom, a hydroxy group, a lower alkoxy group and a lower alkoxy group substituted by a dimethylamino group.

8. The compound according to claim 7 or a salt thereof, wherein in the above formula (2a), $R^{c\beta}$ represents a hydrogen atom, X represents $CH_2NR^{c\beta}$, $R^{c\beta}$ represents a phenyl group, and the phenyl group may be substituted by one or plural groups selected from the group consisting of a halogen atom, a lower alkyl group, a hydroxy group and a lower alkoxy group.

9. The compound according to claim 1 or a salt thereof, wherein in the general formula (1), $R^1$ represents a halogen atom.

10. The compound according to claim 1 or a salt thereof, wherein in the general formula (1), $R^2$ and $R^3$ each represent a hydrogen atom.

11. The compound according to claim 1 or a salt thereof, wherein in the general formula (1), $R^4$ and $R^5$ each represent a hydrogen atom.

12. The compound according to claim 1 or a salt thereof, wherein in the general formula (1), ring A represents a benzene ring or an unsaturated heteromonocyclic ring represented by the following formula (4a)

(4a)

13. A compound selected from the group consisting of:
2-[4-(4-Fluorophenyl)piperazine-1-carbonyl]pyrrolo[1,2-a]quinazolin-5(4H)-one,
2-[4-(4-Chlorobenzyl)piperazine-1-carbonyl]pyrrolo[1,2-a]quinazolin-5(4H)-one,
2-[4-(Thiazol-2-yl)piperazine-1-carbonyl]pyrrolo[1,2-a]quinazolin-5(4H)-one, 2-(4-Phenylpiperazine-1-carbonyl)pyrrolo[1,2-a]quinazolin-5(4H)-one,
2-(4-Phenylpiperidine-1-carbonyl)pyrrolo[1,2-a]quinazolin-5(4H)-one,
2-(4-Phenyl-1,2,3,6-tetrahydropyridine-1-carbonyl)pyrrolo[1,2-a]quinazolin-5(4H)-one,
2-[4-(4-Chlorophenyl)-1,2,3,6-tetrahydropyridine-1-carbonyl]pyrrolo[1,2-a]quinazolin-5(4H)-one,
2-[4-(4-Fluorophenyl)-1,2,3,6-tetrahydropyridine-1-carbonyl]pyrrolo[1,2-a]quinazolin-5(4H)-one,
2-[4-(2-Fluorophenyl)piperazine-1-carbonyl]pyrrolo[1,2-a]quinazolin-5(4H)-one,
2-(4-Methylpiperazine-1-carbonyl)pyrrolo[1,2-a]quinazolin-5(4H)-one,
2-(4-Benzylpiperazine-1-carbonyl)pyrrolo[1,2-a]quinazolin-5(4H)-one,
2-[4-(4-Chlorophenyl)piperazine-1-carbonyl]pyrrolo[1,2-a]quinazolin-5(4H)-one,
2-[4-(4-Fluorobenzyl)piperazine-1-carbonyl]pyrrolo[1,2-a]quinazolin-5(4H)-one,
2-[4-(4-Fluorophenyl)piperidine-1-carbonyl]pyrrolo[1,2-a]quinazolin-5(4H)-one,
2-[4-(3-Fluorophenyl)piperazine-1-carbonyl]pyrrolo[1,2-a]quinazolin-5(4H)-one,
2-[4-(4-Methoxyphenyl)piperazine-1-carbonyl]pyrrolo[1,2-a]quinazolin-5(4H)-one,
2-[4-(Pyridin-2-yl)piperazine-1-carbonyl]pyrrolo[1,2-a]quinazolin-5(4H)-one,
2-[4-(Pyridin-3-yl)piperazine-1-carbonyl]pyrrolo[1,2-a]quinazolin-5(4H)-one,
2-[N-Methyl-N-(3-phenylpropyl)aminocarbonyl]pyrrolo[1,2-a]quinazolin-5(4H)-one,
2-[4-(4-Bromophenyl)piperazine-1-carbonyl]pyrrolo[1,2-a]quinazolin-5(4H)-one,
2-(3,4-Dihydroisoquinoline-2(1H)-carbonyl)pyrrolo[1,2-a]quinazolin-5(4H)-one,
2-(4-Dimethylaminopiperidine-1-carbonyl)pyrrolo[1,2-a]quinazolin-5(4H)-one,
2-[4-(Pyridin-4-yl)piperazine-1-carbonyl]pyrrolo[1,2-a]quinazolin-5(4H)-one,
2-[4-(4-Fluorophenyl)-2-methylpiperazine-1-carbonyl]pyrrolo[1,2-a]quinazolin-5(4H)-one,
2-[4-(2-Methoxyphenyl)piperazine-1-carbonyl]pyrrolo[1,2-a]quinazolin-5(4H)-one,
2-[4-(3-Methoxyphenyl)piperazine-1-carbonyl]pyrrolo[1,2-a]quinazolin-5(4H)-one,
2-(4-Cyclohexylpiperazine-1-carbonyl)pyrrolo[1,2-a]quinazolin-5(4H)-one,
2-[4-Cyclopropylmethylpiperazine-1-carbonyl)pyrrolo[1,2-a]quinazolin-5(4H)-one,
2-[4-(4-Trifluoromethylphenyl)piperazine-1-carbonyl]pyrrolo[1,2-a]quinazolin-5(4H)-one,
2-[4-(5-Chloropyridin-2-yl)piperazine-1-carbonyl]pyrrolo[1,2-a]quinazolin-5(4H)-one,
2-(3-Phenylpiperidine-1-carbonyl)pyrrolo[1,2-a]quinazolin-5(4H)-one,
2-[4-(3-Methylphenyl)piperazine-1-carbonyl]pyrrolo[1,2-a]quinazolin-5(4H)-one,
2-[4-(Piperidin-1-yl)piperidine-1-carbonyl]pyrrolo[1,2-a]quinazolin-5(4H)-one,
2-(Pyrrolidine-1-carbonyl)pyrrolo[1,2-a]quinazolin-5(4H)-one,
2-[4-(2,4-Difluorophenyl)piperazine-1-carbonyl]pyrrolo[1,2-a]quinazolin-5(4H)-one,
2-[4-(Furo[3,2-c]pyridin-4-yl)piperazine-1-carbonyl]pyrrolo[1,2-a]quinazolin-5(4H)-one,
2-[4-(1H-Indol-4-yl)piperazine-1-carbonyl]pyrrolo[1,2-a]quinazolin-5(4H)-one,
2-[4-(4-Isopropoxyphenyl)piperazine-1-carbonyl]pyrrolo[1,2-a]quinazolin-5(4H)-one,
2-[4-(4-Fluoro-2-methoxyphenyl)piperazine-1-carbonyl]pyrrolo[1,2-a]quinazolin-5(4H)-one,
2-[4-(1,3-Benzodioxol-5-yl)piperazine-1-carbonyl]pyrrolo[1,2-a]quinazolin-5(4H)-one,
7-[4-(4-Fluorophenyl)piperazine-1-carbonyl]pyrrolo[1,2-a]thieno[2,3-e]pyrimidin-4(5H)-one,
7-[4-(4-Chlorophenyl)piperazine-1-carbonyl]pyrrolo[1,2-a]thieno[2,3-e]pyrimidin-4(5H)-one,
7-(Pyrrolidine-1-carbonyl)pyrrolo[1,2-a]thieno[2,3-e]pyrimidin-4(5H)-one,
7-Fluoro-2-[4-(pyridin-2-yl)piperazine-1-carbonyl]pyrrolo[1,2-a]quinazolin-5(4H)-one,
7-Fluoro-2-[4-(4-fluorophenyl)piperazine-1-carbonyl]pyrrolo[1,2-a]quinazolin-5(4H)-one,
2-[4-(4-Fluorophenyl)homopiperazine-1-carbonyl]pyrrolo[1,2-a]quinazolin-5(4H)-one,
2-[4-(tert-Butoxycarbonyl)homopiperazine-1-carbonyl]pyrrolo[1,2-a]quinazolin-5(4H)-one,
2-[4-(tert-Butoxycarbonyl)piperazine-1-carbonyl]pyrrolo[1,2-a]quinazolin-5(4H)-one,
2-(Phenylaminocarbonyl)pyrrolo[1,2-a]quinazolin-5(4H)-one,
2-(4-Methylhomopiperazine-1-carbonyl)pyrrolo[1,2-a]quinazolin-5(4H)-one,
2-[(2-Dimethylaminoethyl)aminocarbonyl]pyrrolo[1,2-a]quinazolin-5(4H)-one,
2-[(Pyridin-4-ylmethyl)aminocarbonyl]pyrrolo[1,2-a]quinazolin-5(4H)-one,
2-[2-(Morpholin-4-ylethyl)aminocarbonyl]pyrrolo[1,2-a]quinazolin-5(4H)-one,
2-(Benzylaminocarbonyl)pyrrolo[1,2-a]quinazolin-5(4H)-one,
2-(2-Phenylethylaminocarbonyl)pyrrolo[1,2-a]quinazolin-5(4H)-one,
2-(3-Phenylpropylaminocarbonyl)pyrrolo[1,2-a]quinazolin-5(4H)-one,
2-[4-[2-(2-Dimethylaminoethoxy)-4-fluorophenyl]piperazine-1-carbonyl]pyrrolo[1,2-a]quinazolin-5(4H)-one,
2-[4-(Morpholin-4-yl)piperidine-1-carbonyl]pyrrolo[1,2-a]quinazolin-5(4H)-one,
2-[4-(4-Fluorophenyl)piperazin-1-ylmethyl]pyrrolo[1,2-a]quinazolin-5(4H)-one,
2-[4-(4-Chlorobenzyl)piperazin-1-ylmethyl]pyrrolo[1,2-a]quinazolin-5(4H)-one,
2-[4-(Thiazol-2-yl)piperazin-1-ylmethyl]pyrrolo[1,2-a]quinazolin-5 (4H)-one,
2-(4-Phenylpiperazin-1-ylmethyl)pyrrolo[1,2-a]quinazolin-5 (4H)-one,
2-(4-Phenylpiperidin-1-ylmethyl)pyrrolo[1,2-a]quinazolin-5(4H)-one,
2-(4-Phenyl-1,2,3,6-tetrahydropyridin-1-ylmethyl)pyrrolo[1,2-a]quinazolin-5(4H)-one,
2-[4-(4-Chlorophenyl)-1,2,3,6-tetrahydropyridin-1-ylmethyl]pyrrolo[1,2-a]quinazolin-5(4H)-one,
2-[4-(4-Fluorophenyl)-1,2,3,6-tetrahydropyridin-1-ylmethyl]pyrrolo[1,2-a]quinazolin-5(4H)-one,
2-[4-(2-Fluorophenyl)piperazin-1-ylmethyl]pyrrolo[1,2-a]quinazolin-5(4H)-one,
2-(4-Methylpiperazin-1-ylmethyl)pyrrolo[1,2-a]quinazolin-5(4H)-one,
2-(4-Benzylpiperazin-1-ylmethyl)pyrrolo[1,2-a]quinazolin-5(4H)-one, 2-[4-(4-Chlorophenyl)piperazin-1-ylmethyl]pyrrolo[1,2-a]quinazolin-5(4H)-one,
2-[4-(4-Fluorobenzyl)piperazin-1-ylmethyl]pyrrolo[1,2-a]quinazolin-5(4H)-one,
2-[4-(4-Fluorophenyl)piperidin-1-ylmethyl]pyrrolo[1,2-a]quinazolin-5(4H)-one,
2-[4-(3-Fluorophenyl)piperazin-1-ylmethyl]pyrrolo[1,2-a]quinazolin-5(4H)-one,
2-[4-(4-Methoxyphenyl)piperazin-1-ylmethyl]pyrrolo[1,2-a]quinazolin-5(4H)-one,
2-[4-(Pyridin-2-yl)piperazin-1-ylmethyl]pyrrolo[1,2-a]quinazolin-5(4H)-one,
2-[4-(Pyridin-3-yl)piperazin-1-ylmethyl]pyrrolo[1,2-a]quinazolin-5(4H)-one,
2-[N-Methyl-N-(3-phenylpropyl)aminomethyl]pyrrolo[1,2-a]quinazolin-5(4H)-one,
2-[4-(4-Bromophenyl)piperazin-1-ylmethyl]pyrrolo[1,2-a]quinazolin-5(4H)-one,
2-(1,2,3,4-Tetrahydroisoquinolin-2(1H)-ylmethyl)pyrrolo[1,2-a]quinazolin-5(4H)-one,
2-(4-Dimethylaminopiperidin-1-ylmethyl)pyrrolo[1,2-a]quinazolin-5(4H)-one,
2-[4-(Pyridin-4-yl)piperazin-1-ylmethyl]pyrrolo[1,2-a]quinazolin-5(4H)-one,
2-[4-(4-Fluorophenyl)-2-methylpiperazin-1-ylmethyl]pyrrolo[1,2-a]quinazolin-5(4H)-one,
2-[4-(2-Methoxyphenyl)piperazin-1-ylmethyl]pyrrolo[1,2-a]quinazolin-5(4H)-one,
2-[4-(3-Methoxyphenyl)piperazin-1-ylmethyl]pyrrolo[1,2-a]quinazolin-5(4H)-one,
2-(4-Cyclohexylpiperazin-1-ylmethyl)pyrrolo[1,2-a]quinazolin-5(4H)-one,
2-(4-Cyclopropylmethylpiperazin-1-ylmethyl)pyrrolo[1,2-a]quinazolin-5(4H)-one,
2-[4-(4-Trifluoromethylphenyl)piperazin-1-ylmethyl]pyrrolo[1,2-a]quinazolin-5(4H)-one,
2-[4-(5-Chloropyridin-2-yl)piperazin-1-ylmethyl]pyrrolo[1,2-a]quinazolin-5(4H)-one,
2-(3-Phenylpiperidin-1-ylmethyl)pyrrolo[1,2-a]quinazolin-5(4H)-one,
2-[4-(3-Methylphenyl)piperazin-1-ylmethyl]pyrrolo[1,2-a]quinazolin-5(4H)-one,
2-[4-(Piperidin-1-yl)piperidin-1-ylmethyl]pyrrolo[1,2-a]quinazolin-5(4H)-one,
2-(Pyrrolidin-1-ylmethyl)pyrrolo[1,2-a]quinazolin-5(4H)-one,
2-[4-(2,4-Difluorophenyl)piperazin-1-ylmethyl]pyrrolo[1,2-a]quinazolin-5(4H)-one,
2-[4-(Furo[3,2-c]pyridin-4-yl)piperazin-1-ylmethyl]pyrrolo[1,2-a]quinazolin-5(4H)-one,
2-[4-(1H-Indol-4-yl)piperazin-1-ylmethyl]pyrrolo[1,2-a]quinazolin-5(4H)-one,
2-[4-(4-Isopropoxyphenyl)piperazin-1-ylmethyl]pyrrolo[1,2-a]quinazolin-5(4H)-one,
2-[4-(4-Fluoro-2-methoxyphenyl)piperazin-1-ylmethyl]pyrrolo[1,2-a]quinazolin-5(4H)-one,
2-[4-(1,3-Benzodioxol-5-yl)piperazin-1-ylmethyl]pyrrolo[1,2-a]quinazolin-5(4H)-one,
7-[4-(4-Fluorophenyl)piperazin-1-ylmethyl]pyrrolo[1,2-a]thieno[2,3-e]pyrimidin-4(5H)-one,
7-[4-(4-Chlorophenyl)piperazin-1-ylmethyl]pyrrolo[1,2-a]thieno[2,3-e]pyrimidin-4(5H)-one,
7-(Pyrrolidin-1-ylmethyl)pyrrolo[1,2-a]thieno[2,3-e]pyrimidin-4(5H)-one,
7-Fluoro-2-[4-(pyridin-2-yl)piperazin-1-ylmethyl]pyrrolo[1,2-a]quinazolin-5(4H)-one,
7-Fluoro-2-[4-(4-fluorophenyl)piperazin-1-ylmethyl]pyrrolo[1,2-a]quinazolin-5(4H)-one,
2-[4-[2-(2-Dimethylaminoethoxy)-4-fluorophenyl]piperazin-1-ylmethyl]pyrrolo[1,2-a]quinazolin-5(4H)-one,
2-[4-(Morpholin-4-yl)piperidin-1-ylmethyl]pyrrolo[1,2-a]quinazolin-5(4H)-one,
2-[4-(4-Hydroxyphenyl)piperazin-1-ylmethyl]pyrrolo[1,2-a]quinazolin-5(4H)-one,
2-[1-[4-(4-Fluorophenyl)piperazin-1-yl]-1,1-dideuteriomethyl]pyrrolo[1,2-a]quinazolin-5(4H)-one,
2-(Homopiperazine-1-carbonyl)pyrrolo[1,2-a]quinazolin-5(4H)-one hydrochloride,
2-(piperazine-1-carbonyl)pyrrolo[1,2-a]quinazolin-5(4H)-one, and
2-[4-Cyclopropylcarbonylhomopiperazine-1-carbonyl]pyrrolo[1,2-a]quinazolin-5(4H)-one, or a salt thereof.

14. A pharmaceutical composition comprising at least one of the compound according to claim 1, or a salt thereof, as an active ingredient.

15. A method for inhibiting PARP activity comprising the step of bringing at least one of the compound according to claim 1, or a salt thereof into contact with PARP in vitro or in vivo.

16. A method for therapy of posterior ocular disease comprising the step of administering a pharmaceutically effective amount of at least one of the compounds according to claim 1, or a salt thereof to a patient.

17. The compound according to any claim 1, or a salt thereof for use in inhibition of PARP activity.

18. The compound according to claim 1, or a salt thereof for use in prophylaxis or therapy of posterior ocular disease.

* * * * *